:::

United States Patent
Makino et al.

(10) Patent No.: US 11,253,208 B2
(45) Date of Patent: Feb. 22, 2022

(54) TOMOSYNTHESIS IMAGING CONTROL DEVICE, METHOD FOR OPERATING TOMOSYNTHESIS IMAGING CONTROL DEVICE, AND PROGRAM FOR OPERATING TOMOSYNTHESIS IMAGING CONTROL DEVICE

(71) Applicant: FUJIFILM Corporation, Tokyo (JP)

(72) Inventors: Kazuhiro Makino, Kanagawa (JP); Takeyasu Kobayashi, Kanagawa (JP); Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/919,399

(22) Filed: Jul. 2, 2020

(65) Prior Publication Data

US 2021/0022689 A1   Jan. 28, 2021

(30) Foreign Application Priority Data

Jul. 26, 2019 (JP) .............................. JP2019-137742

(51) Int. Cl.
*A61B 6/02* (2006.01)
*A61B 6/00* (2006.01)

(52) U.S. Cl.
CPC .............. *A61B 6/025* (2013.01); *A61B 6/502* (2013.01)

(58) Field of Classification Search
CPC ................................ A61B 6/025; A61B 6/502
See application file for complete search history.

(56) References Cited

U.S. PATENT DOCUMENTS

| | | | |
|---|---|---|---|
| 2004/0228434 A1* | 11/2004 | Tsujii | A61B 6/542 378/4 |
| 2010/0246759 A1* | 9/2010 | Ogura | A61B 6/502 378/21 |
| 2014/0185738 A1* | 7/2014 | Lee | A61B 6/022 378/4 |
| 2015/0189194 A1* | 7/2015 | Tajima | A61B 6/488 378/62 |
| 2015/0297157 A1* | 10/2015 | Mukumoto | A61B 6/5205 378/15 |
| 2016/0015333 A1* | 1/2016 | Morita | A61B 6/502 378/22 |
| 2016/0183896 A1* | 6/2016 | Muller | A61B 6/461 600/424 |
| 2016/0206268 A1* | 7/2016 | Fukuda | A61B 6/502 |

(Continued)

FOREIGN PATENT DOCUMENTS

EP   2326248 B1   11/2017
JP   2016135319 A   7/2016

*Primary Examiner* — Blake C Riddick
(74) *Attorney, Agent, or Firm* — Studebaker & Brackett PC

(57) ABSTRACT

A control device includes a control unit and a determination unit. The control unit controls an operation of radiation tubes such that radiation is emitted at irradiation positions whose number is smaller than the total number of irradiatable positions preset so as to correspond to irradiation angles. The determination unit determines whether or not the radiation needs to be additionally emitted at the irradiatable positions different from the irradiation positions in order to obtain the tomographic image with an image quality level required for diagnosis, on the basis of a determination image obtained by the emission of the radiation at the irradiation positions.

21 Claims, 44 Drawing Sheets

(56) References Cited

U.S. PATENT DOCUMENTS

| | | | |
|---|---|---|---|
| 2016/0249868 A1* | 9/2016 | Nakayama | A61B 6/502 378/4 |
| 2017/0020478 A1* | 1/2017 | Tanaka | A61B 6/032 |
| 2017/0231593 A1* | 8/2017 | Fukuda | A61B 6/5241 382/132 |
| 2017/0236276 A1* | 8/2017 | Fukuda | A61B 6/025 382/131 |
| 2017/0325765 A1* | 11/2017 | Kido | A61B 6/06 |
| 2019/0175133 A1* | 6/2019 | Lin | A61B 6/583 |

* cited by examiner

FIG. 13

| IMAGING SET | PROJECTION IMAGES USED TO GENERATE DETERMINATION TOMOGRAPHIC IMAGE |
|---|---|
| FIRST | PROJECTION IMAGES OBTAINED BY EMISSION OF RADIATION AT SP1 AND SP15 |
| SECOND | PROJECTION IMAGES OBTAINED BY EMISSION OF RADIATION AT SP1, SP2, SP14, AND SP15 |
| THIRD | PROJECTION IMAGES OBTAINED BY EMISSION OF RADIATION AT SP1 TO SP3 AND SP13 TO SP15 |
| FOURTH | PROJECTION IMAGES OBTAINED BY EMISSION OF RADIATION AT SP1 TO SP4 AND SP12 TO SP15 |
| FIFTH | PROJECTION IMAGES OBTAINED BY EMISSION OF RADIATION AT SP1 TO SP5 AND SP11 TO SP15 |
| SIXTH | PROJECTION IMAGES OBTAINED BY EMISSION OF RADIATION AT SP1 TO SP6 AND SP10 TO SP15 |
| SEVENTH | PROJECTION IMAGES OBTAINED BY EMISSION OF RADIATION AT SP1 TO SP7 AND SP9 TO SP15 |
| EIGHTH | PROJECTION IMAGES OBTAINED BY EMISSION OF RADIATION AT SP1 TO SP15 |

DETERMINATION CONDITIONS

GRANULARITY EVALUATION VALUE OF DETERMINATION TOMOGRAPHIC IMAGE IS LESS THAN GRANULARITY EVALUATION THRESHOLD VALUE
DEPTH RESOLUTION EVALUATION VALUE OF DETERMINATION TOMOGRAPHIC IMAGE IS LESS THAN DEPTH RESOLUTION EVALUATION THRESHOLD VALUE

RADIATION NEEDS TO BE ADDITIONALLY EMITTED

GRANULARITY EVALUATION VALUE OF DETERMINATION TOMOGRAPHIC IMAGE IS EQUAL TO OR GREATER THAN GRANULARITY EVALUATION THRESHOLD VALUE
DEPTH RESOLUTION EVALUATION VALUE OF DETERMINATION TOMOGRAPHIC IMAGE IS EQUAL TO OR GREATER THAN DEPTH RESOLUTION EVALUATION THRESHOLD VALUE

RADIATION DOES NOT NEED TO BE ADDITIONALLY EMITTED

| SETTING CONDITIONS ||
|---|---|
| IMAGING SET | RADIATION TUBE ID (IRRADIATION POSITION) |
| FIRST | RT04, RT12 (SP4, SP12) |

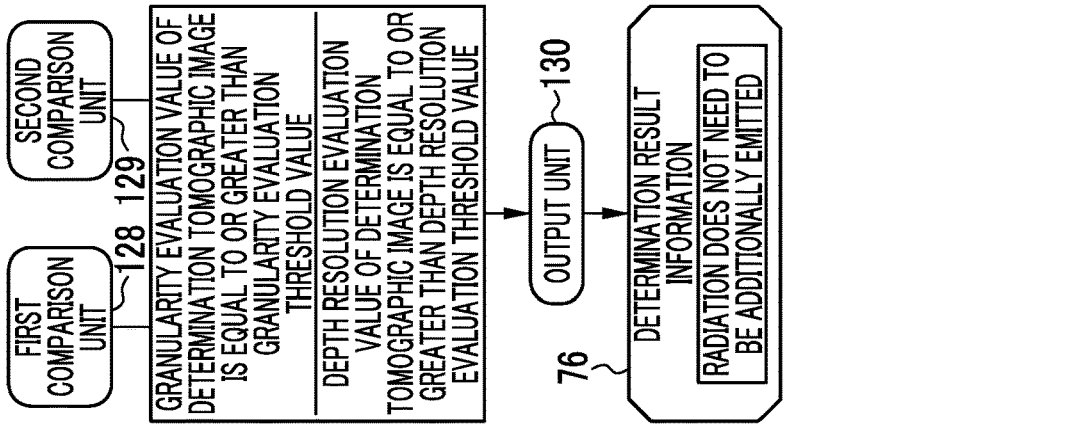
FIG. 30A / FIG. 30B / FIG. 30C / FIG. 30D

| DETERMINATION CONDITIONS ||
| IMAGING SET | RADIATION TUBE ID (IRRADIATION POSITION) |
| --- | --- |
| FIRST | RT01, RT08, RT15 (SP1, SP8, SP15) |

TOMOSYNTHESIS IMAGING CONTROL DEVICE, METHOD FOR OPERATING TOMOSYNTHESIS IMAGING CONTROL DEVICE, AND PROGRAM FOR OPERATING TOMOSYNTHESIS IMAGING CONTROL DEVICE

CROSS-REFERENCE TO RELATED APPLICATIONS

The present application claims priority under 35 U.S.C. § 119 to Japanese Patent Application No. 2019-137742 filed on Jul. 26, 2019. The above application is hereby expressly incorporated by reference, in its entirety, into the present application.

BACKGROUND

1. Technical Field

The technology of the present disclosure relates to a tomosynthesis imaging control device, a method for operating a tomosynthesis imaging control device, and a program for operating a tomosynthesis imaging control device.

2. Description of the Related Art

Tomosynthesis imaging is performed which irradiates an object with radiation at a plurality of different irradiation angles in order to generate a tomographic image in any tomographic plane of the object. JP2016-135319A discloses a technique that performs tomosynthesis imaging while moving a radiation source including one radiation tube to a plurality of irradiatable positions corresponding to a plurality of irradiation angles.

SUMMARY

The quality of the tomographic image is improved by increasing the number of irradiation positions where radiation is emitted among the irradiatable positions or by reducing the interval between the irradiation positions where radiation is emitted. However, even in a case in which the number of irradiation positions is not so large or even in a case in which the interval between the irradiation positions is not so small, a tomographic image with an image quality level required for diagnosis may be obtained depending on the state of the object, such as thickness or a tissue distribution. Therefore, even in a case in which the quality of the tomographic image is improved by increasing the number of irradiation positions or by reducing the interval between the irradiation positions, the image quality may be over-specified depending on the state of the object. In a case in which the quality of the tomographic image is over-specified, it takes a lot of time to emit radiation, which is originally unnecessary. In addition, unnecessary radiation is emitted to the object.

However, inversely, in a case in which the number of irradiation positions is reduced or the interval between the irradiation positions is reduced in order to prevent the quality of the tomographic image from being over-specified, a tomographic image with an image quality level required for diagnosis may not be obtained. In a case in which a tomographic image with an image quality level required for diagnosis is not obtained, it is necessary to increase the number of irradiation positions or to reduce the interval between the irradiation positions and then to perform re-imaging. As described above, the technique disclosed in JP2016-135319A has the configuration in the radiation source including one radiation tube is moved. Therefore, in a case in which it is necessary to perform re-imaging, the imaging time increases.

An object of the technology of the present disclosure is to provide a tomosynthesis imaging control device, a method for operating a tomosynthesis imaging control device, and a program for operating a tomosynthesis imaging control device that can obtain a tomographic image with an image quality level required for diagnosis while preventing unnecessary exposure and an increase in imaging time.

In order to achieve the above object, according to the present disclosure, there is provided a tomosynthesis imaging control device comprising: a control unit that, in a case in which tomosynthesis imaging that irradiates an object with radiation at a plurality of different irradiation angles to generate a tomographic image in any tomographic plane of the object is performed using a plurality of radiation tubes, controls an operation of the radiation tubes such that the radiation is emitted at irradiation positions whose number is smaller than a total number of irradiatable positions preset so as to correspond to the irradiation angles; and a determination unit that determines whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

Preferably, the tomographic image is generated from all of the projection images obtained by the emission of the radiation at the irradiation positions.

Preferably, in a case in which the determination unit determines that the radiation needs to be additionally emitted at the irradiatable positions different from the irradiation positions, the control unit performs control to additionally emit the radiation at an additional irradiation position among the different irradiatable positions. Preferably, in a case in which the determination unit determines that the radiation does not need to be additionally emitted at the irradiatable positions different from the irradiation positions, the control unit ends the tomosynthesis imaging.

Preferably, the determination unit performs the determination, using a determination tomographic image generated from at least two projection images obtained by the emission of the radiation at at least two irradiation positions as the determination image.

Preferably, the determination unit performs the determination by comparing an image quality evaluation value of the determination tomographic image with a preset image quality evaluation threshold value. In this case, preferably, the image quality evaluation value is a value of a lesion of the object.

Preferably, the determination unit performs the determination using a first machine learning model to which the determination tomographic image is input as the determination image and which outputs data indicating whether or not a quality of the input determination tomographic image is at the level required for diagnosis.

Preferably, the determination unit performs the determination using a second machine learning model to which a cut-out image obtained by cutting out a region of a lesion of the object from the determination tomographic image is input as the determination image and which outputs data indicating whether or not a quality of the input cut-out image is at a level required for diagnosis.

Preferably, the tomosynthesis imaging control device further comprises: a display control unit that performs control to display the determination tomographic image; and a receiving unit that receives a command to select whether or not a quality of the determination tomographic image is at the level required for diagnosis. Preferably, the determination unit performs the determination on the basis of the selection command received by the receiving unit.

Preferably, the image quality includes granularity and depth resolution. Preferably, the determination unit individually determines whether or not the granularity of the determination tomographic image is at a level required for diagnosis and whether or not the depth resolution of the determination tomographic image is at a level required for diagnosis. Preferably, the additional irradiation position is changed in a case in which the depth resolution is at the level required for diagnosis and the granularity is not at the level required for diagnosis, in a case in which the granularity is at the level required for diagnosis and the depth resolution is not at the level required for diagnosis, and in a case in which the granularity and the depth resolution are not at the levels required for diagnosis.

Preferably, the tomosynthesis imaging control device further comprises a storage control unit that performs control to store an irradiation position related information table in which information related to the irradiation position where the radiation has been emitted by the control unit is registered for each subject. Preferably, an initial irradiation position is set on the basis of the irradiation position related information table.

Preferably, the determination unit performs the determination using a third machine learning model to which a determination tomographic image generated from at least two projection images obtained by the emission of the radiation at at least two initial irradiation positions is input as the determination image and which outputs the irradiation position where the emission of the radiation is essential to generate the tomographic image with the image quality level required for diagnosis.

Preferably, the determination unit performs the determination using a fourth machine learning model to which a projection image obtained by the emission of the radiation at an initial irradiation position is input as the determination image and which outputs the irradiation position where the emission of the radiation is essential to generate the tomographic image with the image quality level required for diagnosis.

Preferably, the determination image is an image in which pixels have been thinned out as compared to an image output from a radiation detector.

Preferably, the irradiatable positions that are symmetric with respect to a line and/or the irradiatable positions that are arranged at equal intervals are set as the irradiation positions at a time.

Preferably, the irradiatable positions corresponding to a maximum irradiation angle are set as the initial irradiation positions.

Preferably, the irradiatable positions having a smaller irradiation angle than previous irradiation positions are set as the additional irradiation positions.

Preferably, the radiation tube is fixed at the irradiatable position.

Preferably, the radiation tube is moved between at least two irradiatable positions.

According to the present disclosure, there is provided a method for operating a tomosynthesis imaging control device. The method comprises: a control step of, in a case in which tomosynthesis imaging that irradiates an object with radiation at a plurality of different irradiation angles to generate a tomographic image in any tomographic plane of the object is performed using a plurality of radiation tubes, controlling an operation of the radiation tubes such that the radiation is emitted at irradiation positions whose number is smaller than a total number of irradiatable positions preset so as to correspond to the irradiation angles; and a determination step of determining whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

According to the present disclosure, there is provided a program for operating a tomosynthesis imaging control device. The program causes a computer to function as: a control unit that, in a case in which tomosynthesis imaging that irradiates an object with radiation at a plurality of different irradiation angles to generate a tomographic image in any tomographic plane of the object is performed using a plurality of radiation tubes, controls an operation of the radiation tubes such that the radiation is emitted at irradiation positions whose number is smaller than a total number of irradiatable positions preset so as to correspond to the irradiation angles; and a determination unit that determines whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

According to the technology of the present disclosure, it is possible to provide a tomosynthesis imaging control device, a method for operating a tomosynthesis imaging control device, and a program for operating a tomosynthesis imaging control device that can obtain a tomographic image with an image quality level required for diagnosis while preventing unnecessary exposure and an increase in imaging time.

BRIEF DESCRIPTION OF THE DRAWINGS

Exemplary embodiments according to the technique of the present disclosure will be described in detail based on the following figures, wherein:

FIG. 13 is a table illustrating projection images used to generate a determination tomographic image in each imaging set;

FIG. 28 is a diagram illustrating determination conditions according to the third embodiment;

FIG. 29 is a diagram illustrating setting conditions according to the third embodiment;

FIGS. 30A to 30D are diagrams illustrating variations in a first imaging set in the third embodiment; FIG. 30A illustrates a case in which the depth resolution of the determination tomographic image is at a level required for diagnosis, but the granularity thereof is not a level required for diagnosis; FIG. 30B illustrates a case in which the granularity of the determination tomographic image is at the level required for diagnosis, but the depth resolution thereof is not at the level required for the diagnosis; FIG. 30C illustrates a case in which the granularity and the depth resolution of the determination tomographic image are not at the levels required for the diagnosis; FIG. 30D illustrates a case in which the granularity and the depth resolution of the determination tomographic image are at the levels required for diagnosis;

FIG. 33A illustrates a case in which the quality of the determination tomographic image is not at the level required for diagnosis and FIG. 33B illustrates a case in which the quality of the determination tomographic image is at the level required for diagnosis;

FIG. 44 is a diagram illustrating setting conditions according to the eighth embodiment;

FIG. 45A illustrates a case in which output data includes irradiation essential positions that are not included in the irradiation positions corresponding to the radiation tubes in the first imaging set and FIG. 45B illustrates a case in which the output data does not include the irradiation essential positions that are not included in the irradiation positions corresponding to the radiation tubes in the first imaging set;

DETAILED DESCRIPTION

First Embodiment

Figure 1:
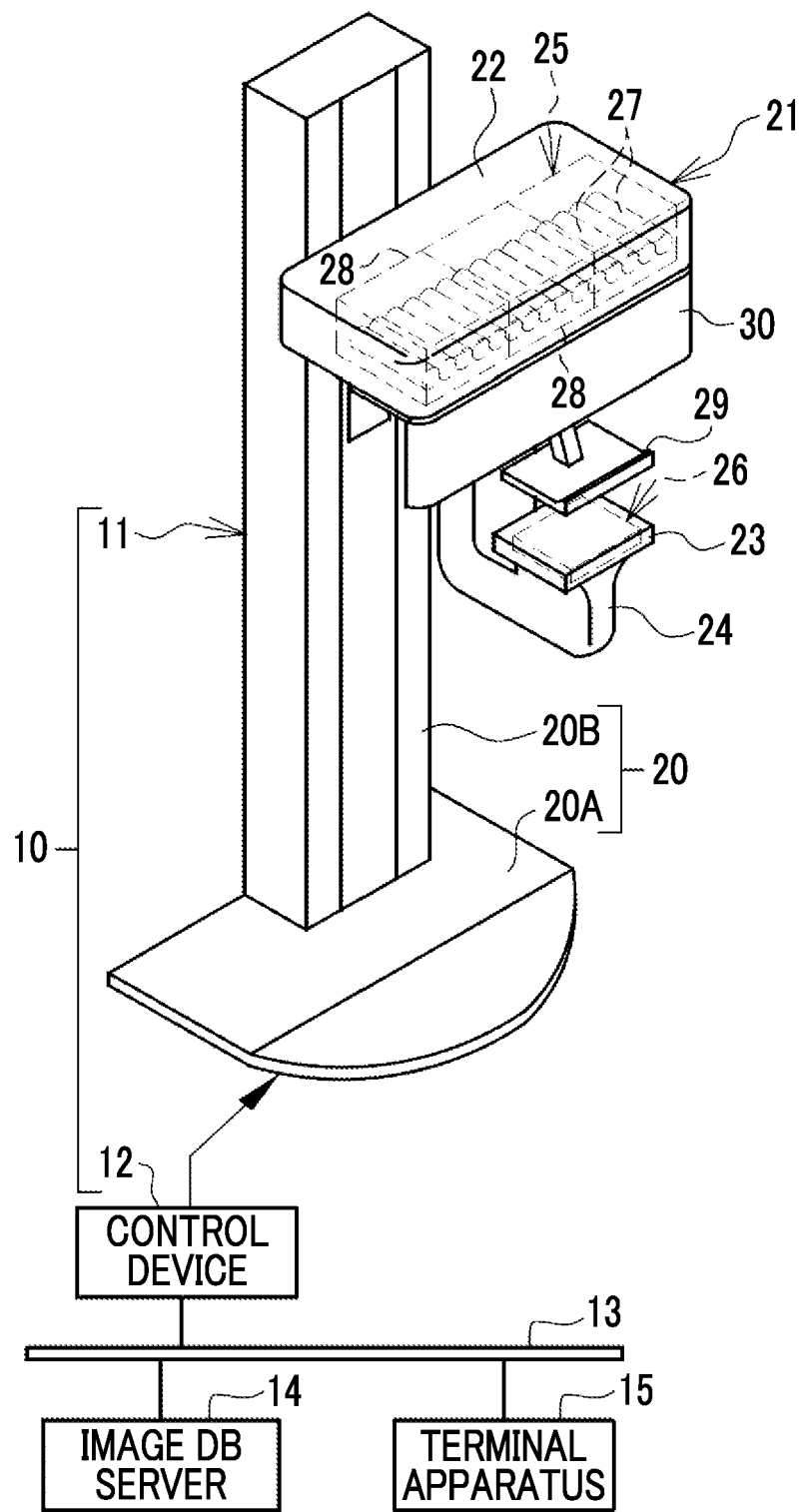
FIG. 1 is a diagram illustrating, for example, a mammography apparatus.
Figure 2:
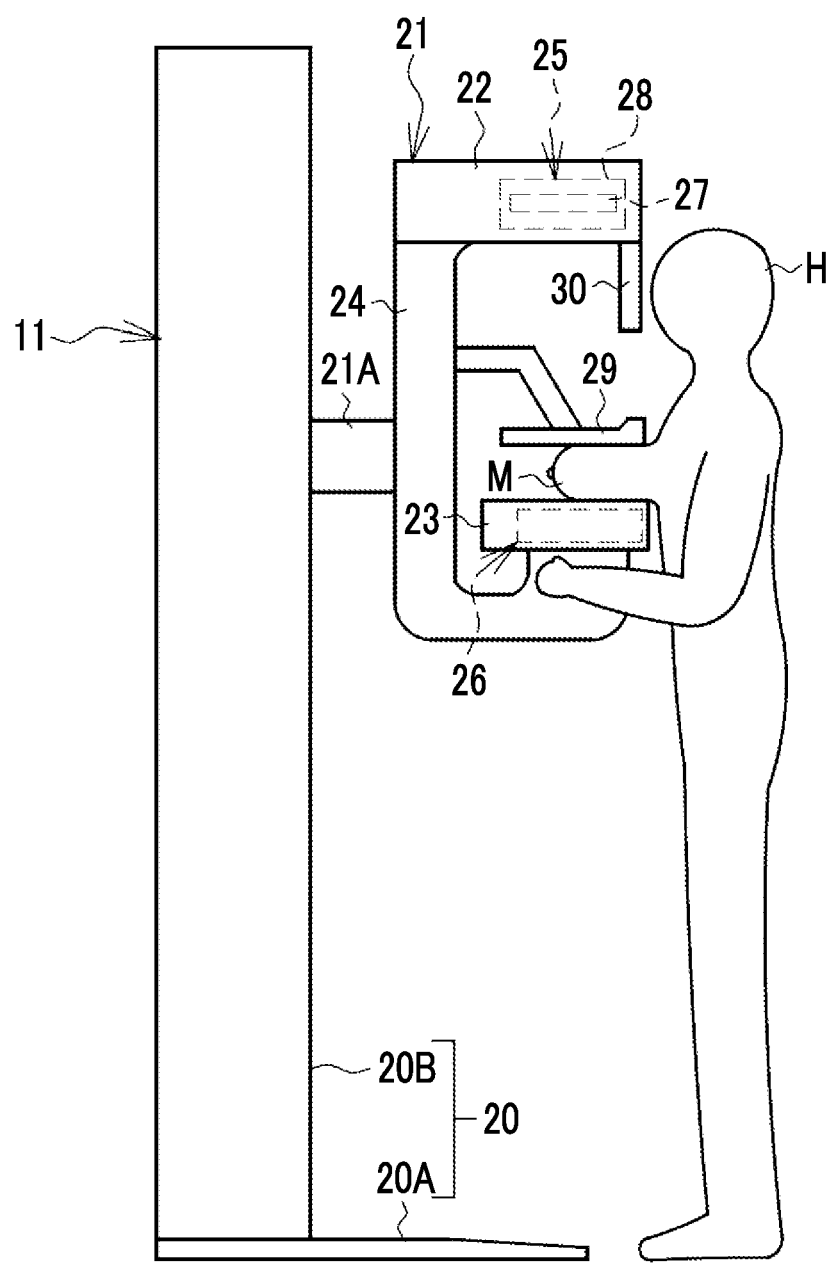
FIG. 2 is a diagram illustrating an apparatus main body of the mammography apparatus.

In FIGS. 1 and 2, a mammography apparatus 10 uses a breast M of a subject H as an object. The mammography apparatus 10 irradiates the breast M with radiation 37 (see, for example, FIG. 3), such as X-rays or γ-rays, to capture a radiographic image of the breast M.

The mammography apparatus 10 includes an apparatus main body 11 and a control device 12 which is an example of a "tomosynthesis imaging control device" according to the technology of the present disclosure. The apparatus main body 11 is installed, for example, in a radiography room of a medical facility. The control device 12 is installed, for example, in a control room next to the radiography room. The control device 12 is, for example, a desktop personal computer. The control device 12 is connected to an image database (hereinafter, referred to as a DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, stores the radiographic image, and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of radiation tubes 27, for example, 15 radiation tubes 27 and three housing 28 each of which accommodates five radiation tubes 27. The radiation tubes 27 are used for tomosynthesis imaging which captures a plurality of projection images P (see FIG. 7) of the breast M at different irradiation angles as radiographic images. The radiation detector 26 detects the radiation 37 transmitted through the breast M and outputs a radiographic image. The number of radiation tubes 27 is not limited to 15 in the above example.

A compression plate 29 is attached between the radiation source accommodation portion 22 and the detector accommodation portion 23 in the main body portion 24. The compression plate 29 is made of a material that transmits the radiation 37. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
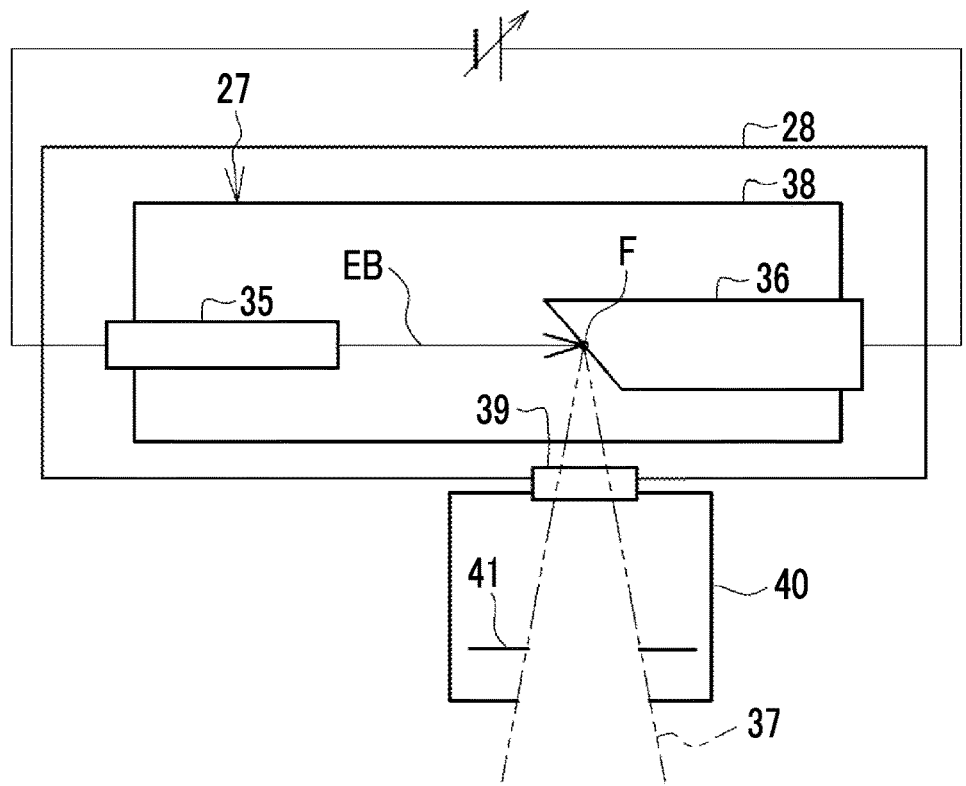
FIG. 3 is a diagram illustrating a radiation tube.

In FIG. 3, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38. The cathode 35 is a cold cathode. Specifically, the cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

The housing 28 is provided with a radiation transmission window 39 that transmits the radiation 37. The radiation 37 emitted from the anode 36 is emitted to the outside of the housing 28 through the radiation transmission window 39. In addition, the housing 28 is filled with insulating oil.

An irradiation field limiter 40 (not illustrated in FIGS. 1 and 2) is provided below the radiation transmission window 39 in the height direction. The irradiation field limiter 40 is also called a collimator and sets the irradiation field of the radiation 37 in an imaging surface 45 (see FIG. 4) of the radiation detector 26. Specifically, the irradiation field limiter 40 includes a plurality of shielding plates 41 which are made of, for example, lead and shield the radiation 37 transmitted through the radiation transmission window 39. The shielding plates 41 are moved to change the size of, for example, a rectangular irradiation opening defined by the shielding plates 41, thereby setting the irradiation field of the radiation 37.

Figure 4:
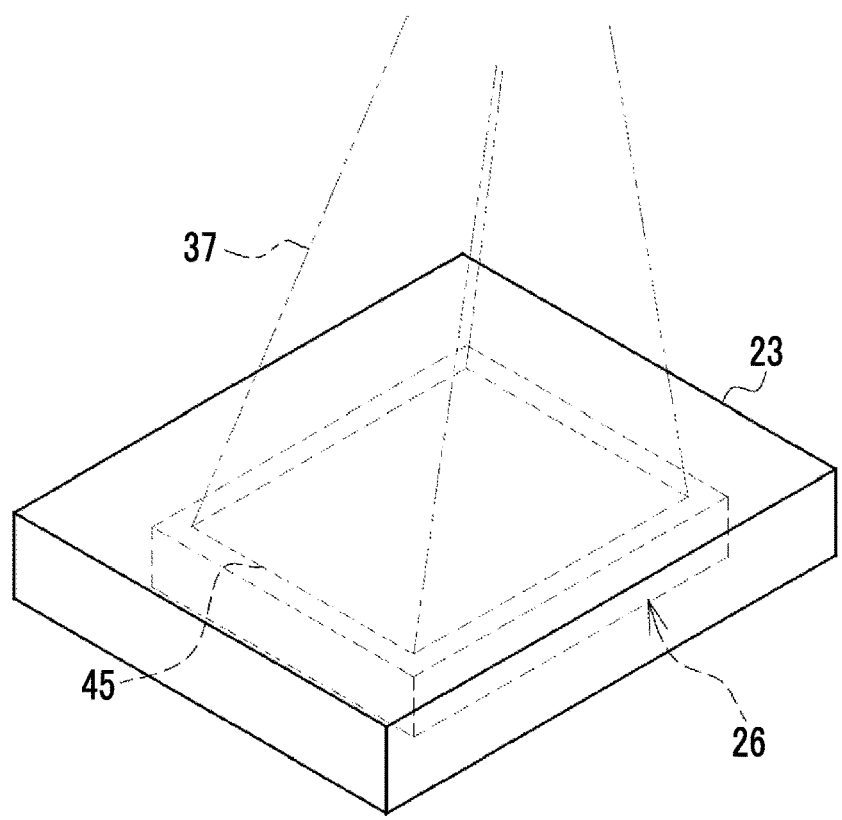
FIG. 4 is a diagram illustrating a detector accommodation portion.

In FIG. 4 illustrating the detector accommodation portion 23, the radiation detector 26 has the imaging surface 45. The imaging surface 45 detects the radiation 37 transmitted through the breast M and captures a projection image of the breast M. Specifically, the imaging surface 45 is a two-dimensional plane in which pixels converting the radiation 37 into an electric signal are two-dimensionally arranged. The radiation detector 26 is called a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 5:
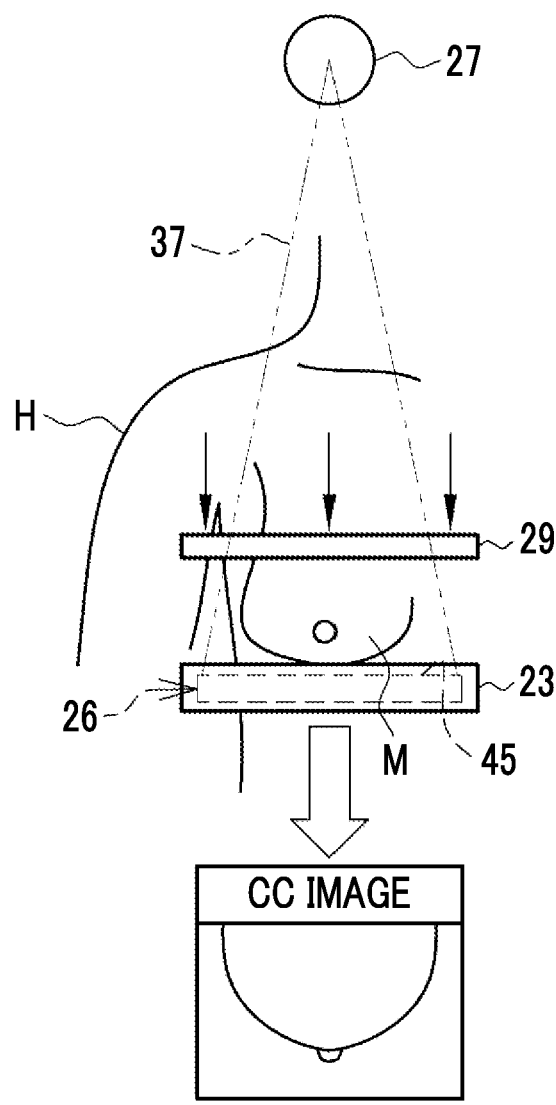
FIG. 5 is a diagram illustrating an aspect of CC imaging.
Figure 6:
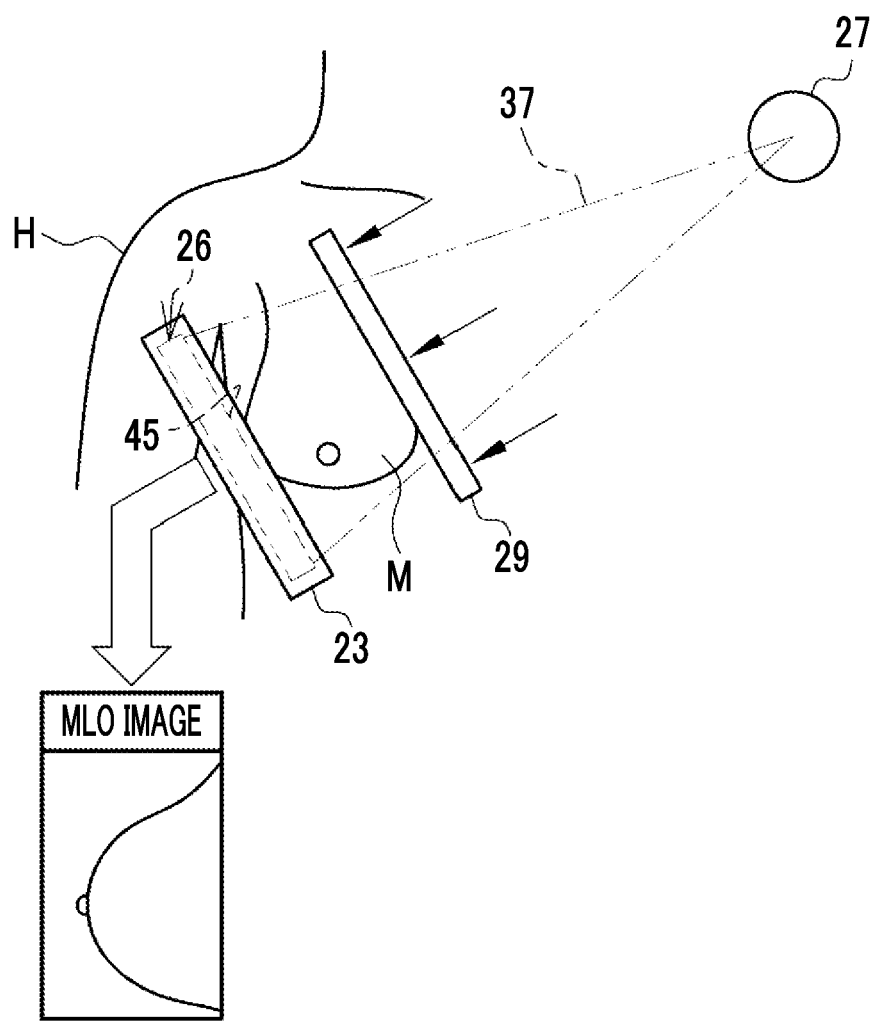
FIG. 6 is a diagram illustrating an aspect of MLO imaging.

FIGS. 5 and 6 illustrate a method for imaging an image of the breast M in the mammography apparatus 10. FIG. 5 illustrates craniocaudal view (CC) imaging and FIG. 6 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image. In addition, FIGS. 5 and 6 illustrate only one radiation tube 27 for simplicity of illustration. Further, FIGS. 5 and 6 illustrate the right breast M. However, an image of the left breast M may be captured.

Figure 7:
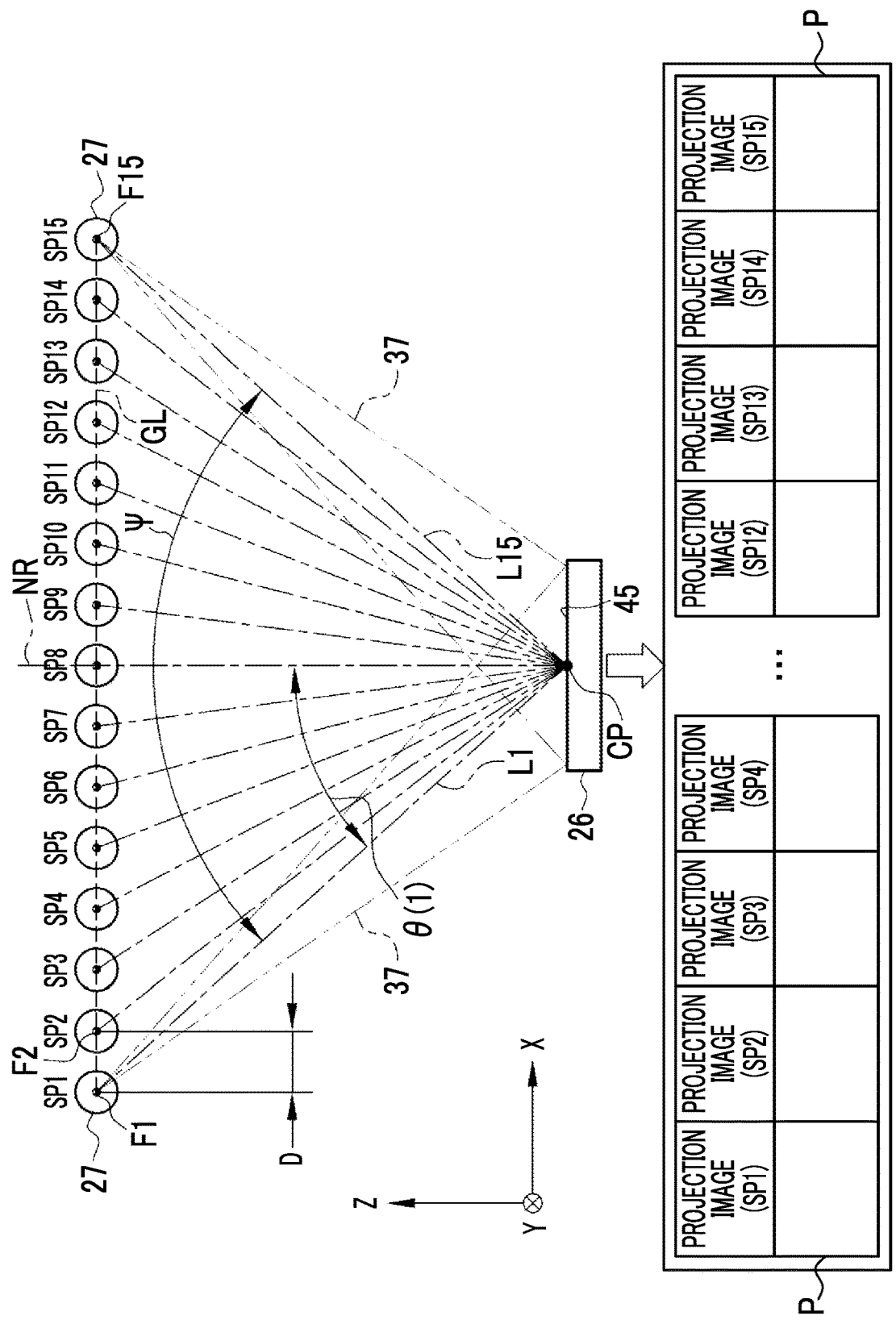
FIG. 7 is a diagram illustrating an aspect of tomosynthesis imaging.

In FIG. 7 which is a plan view illustrating the radiation source 25 and the radiation detector 26 as viewed from the support 20B, it is assumed that the direction of a normal line to the imaging surface 45 is the Z direction, a direction along a side of the imaging surface 45 is the X direction, and a depth direction of the imaging surface 45 which is perpendicular to the Z direction and the X direction is the Y direction. The radiation tubes 27 are provided at a total of 15 irradiatable positions SP1, SP2, . . . , SP14, and SP15 where the radiation 37 is emitted to the imaging surface 45 at different irradiation angles. Focuses F1 to F15 of the radiation 37 in the radiation tubes 27 at the irradiatable positions SP1 to SP15 are arranged in a straight line at equal intervals D.

The irradiatable position SP8 is disposed on a normal line NR to the imaging surface 45 which extends from a center point CP of a side of the imaging surface 45 in the X direction. Irradiatable positions other than the irradiatable position SP8 are set so as to be bilaterally symmetric with respect to the normal line NR. For example, the irradiatable positions SP1 to SP7 are disposed on the left side of the normal line NR and the irradiatable positions SP9 to SP15 are disposed on the right side of the normal line NR. That is, the radiation tubes 27 at the irradiatable positions SP1 to SP7 and the radiation tubes 27 at the irradiatable positions SP9 to SP15 are disposed at positions that are symmetric with respect to a line.

Here, a straight line GL on which the irradiatable positions SP1 to SP15 are set is parallel to the side of the imaging surface 45 along the X direction in a plan view of the radiation source 25 and the radiation detector 26 from the Z direction. The straight line GL is offset to the front side (a side opposite to the support 20B) in the Y direction. The present disclosure is not limited to a case in which the intervals D between the focuses F1 to F15 are exactly equal to each other. For example, an error of ±5% is allowed in the interval D.

The irradiation angle of the radiation 37 is an angle formed between the normal line NR and a line connecting the center point CP and each of the focuses F1 to F15 of the radiation 37 in the radiation tubes 27 at the irradiatable positions SP1 to SP15. Therefore, the irradiation angle at the irradiatable position SP8 aligned with the normal line NR is 0°. For example, FIG. 7 illustrates a line L1 connecting the focus F1 at the irradiatable position SP1 and the center point CP and an irradiation angle θ(1) formed between the normal line NR and the line L1.

An angle represented by a symbol Ψ is the maximum scanning angle of tomosynthesis imaging. The maximum scanning angle Ψ is defined by the irradiatable positions SP1 and SP15 at both ends among the irradiatable positions SP1 to SP15. Specifically, the maximum scanning angle Ψ is an angle formed between the line L1 connecting the focus F1 at the irradiatable position SP1 and the center point CP and a line L15 connecting the focus F15 at the irradiatable position SP15 and the center point CP.

In one normal tomosynthesis imaging operation, each of the radiation tubes 27 at the irradiatable positions SP1 to SP15 is operated and emits the radiation 37 toward the breast M from each of the irradiatable positions SP1 to SP15. The radiation detector 26 detects the radiation 37 emitted at each of the irradiatable positions SP1 to SP15 whenever the radiation 37 is emitted and outputs projection images P at the irradiatable positions SP1 to SP15. The tomosynthesis imaging can be performed by both the CC imaging method illustrated in FIG. 5 and the MLO imaging method illustrated in FIG. 6. In the case of simple imaging in which the CC imaging illustrated in FIG. 5 and the MLO imaging illustrated in FIG. 6 are independently performed, only the radiation tube 27 at the irradiatable position SP8 where the irradiation angle is 0° is operated.

Figure 8:
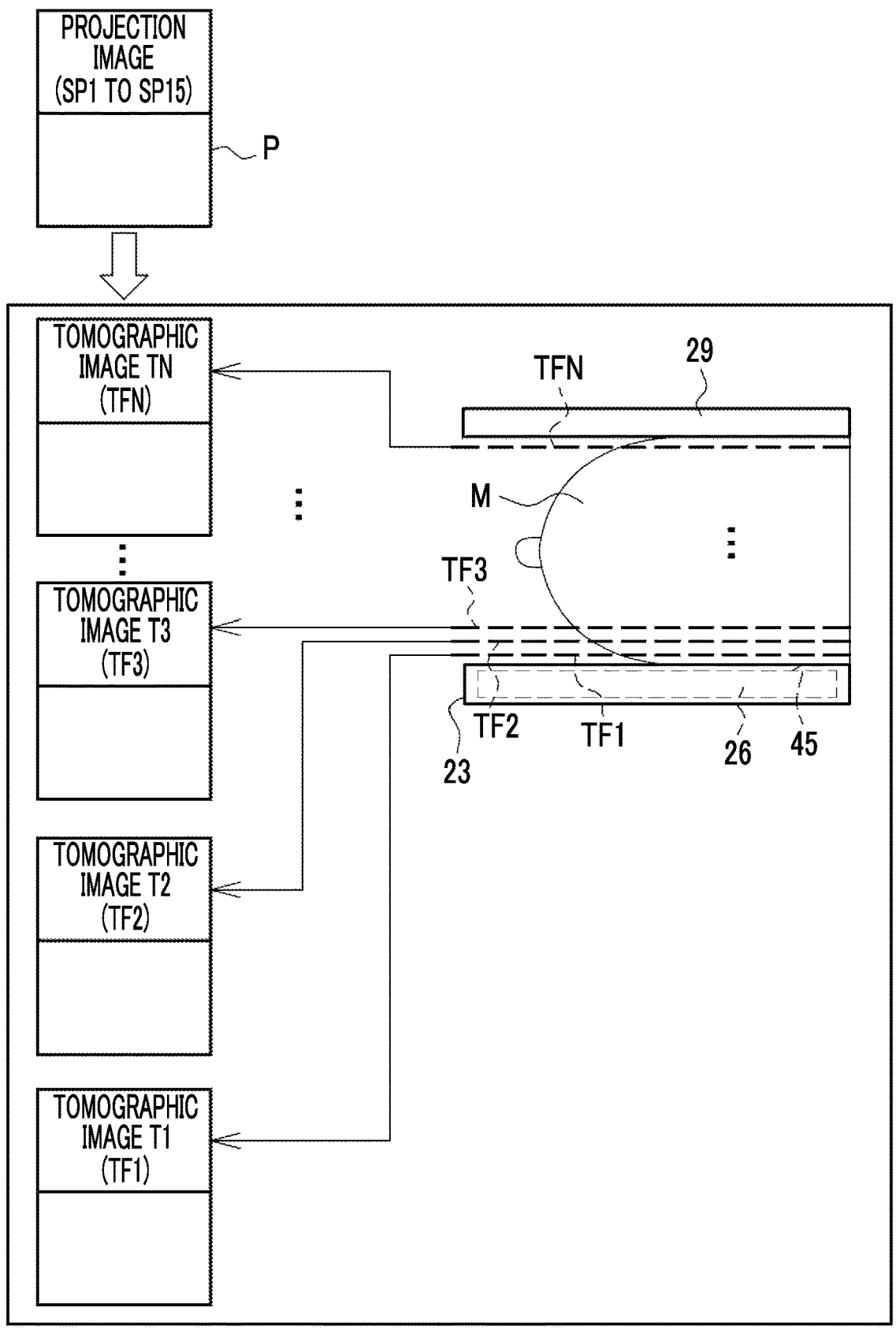
FIG. 8 is a diagram illustrating an aspect in which tomographic images are generated from a plurality of projection images obtained by the tomosynthesis imaging.

As illustrated in FIG. 8, in general, the mammography apparatus 10 generates tomographic images T1 to TN corresponding to any tomographic planes TF1 to TFN of the breast M from a plurality of projection images P at the plurality of irradiatable positions SP1 to SP15 obtained by the tomosynthesis imaging illustrated in FIG. 7. The mammography apparatus 10 generates the tomographic images T1 to TN using a known method such as a filtered back projection method. The tomographic images T1 to TN are images in which structures in the tomographic planes TF1 to TFN have been highlighted.

Figure 9:
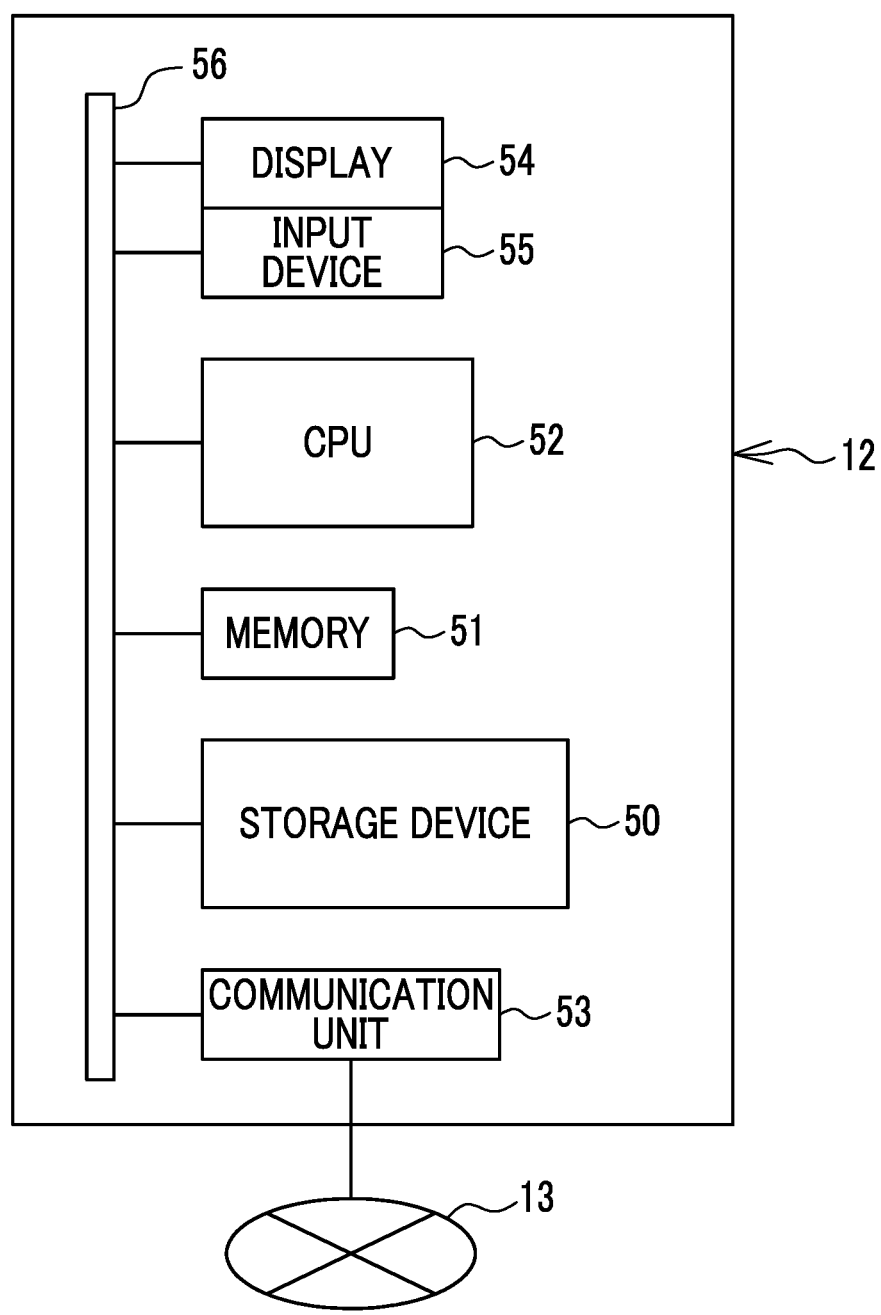
FIG. 9 is a block diagram illustrating a computer forming a control device.

In FIG. 9, a computer forming the control device 12 comprises a storage device 50, a memory 51, a central processing unit (CPU) 52, a communication unit 53, a display 54, and an input device 55. These units are connected to each other through a bus line 56.

The storage device 50 is a hard disk drive that is provided in the computer forming the control device 12 or is connected to the computer through a cable or a network. Alternatively, the storage device 50 is a disk array in which a plurality of hard disk drives are connected. The storage device 50 stores a control program, such as an operating system, various application programs, and various kinds of data associated with these programs. In addition, a solid state drive may be used instead of the hard disk drive.

The memory 51 is a work memory used by the CPU 52 to perform processes. The CPU 52 loads the program stored in the storage device 50 to the memory 51 and performs a process corresponding to the program to control the overall operation of each unit of the computer.

The communication unit 53 is a network interface that controls the transmission of various kinds of information through the network 13. The display 54 displays various screens. The various screens have operation functions by a graphical user interface (GUI). The computer forming the control device 12 receives the input of operation commands from the input device 55 through various screens. The input device 55 is, for example, a keyboard, a mouse, or a touch panel.

Figure 10:
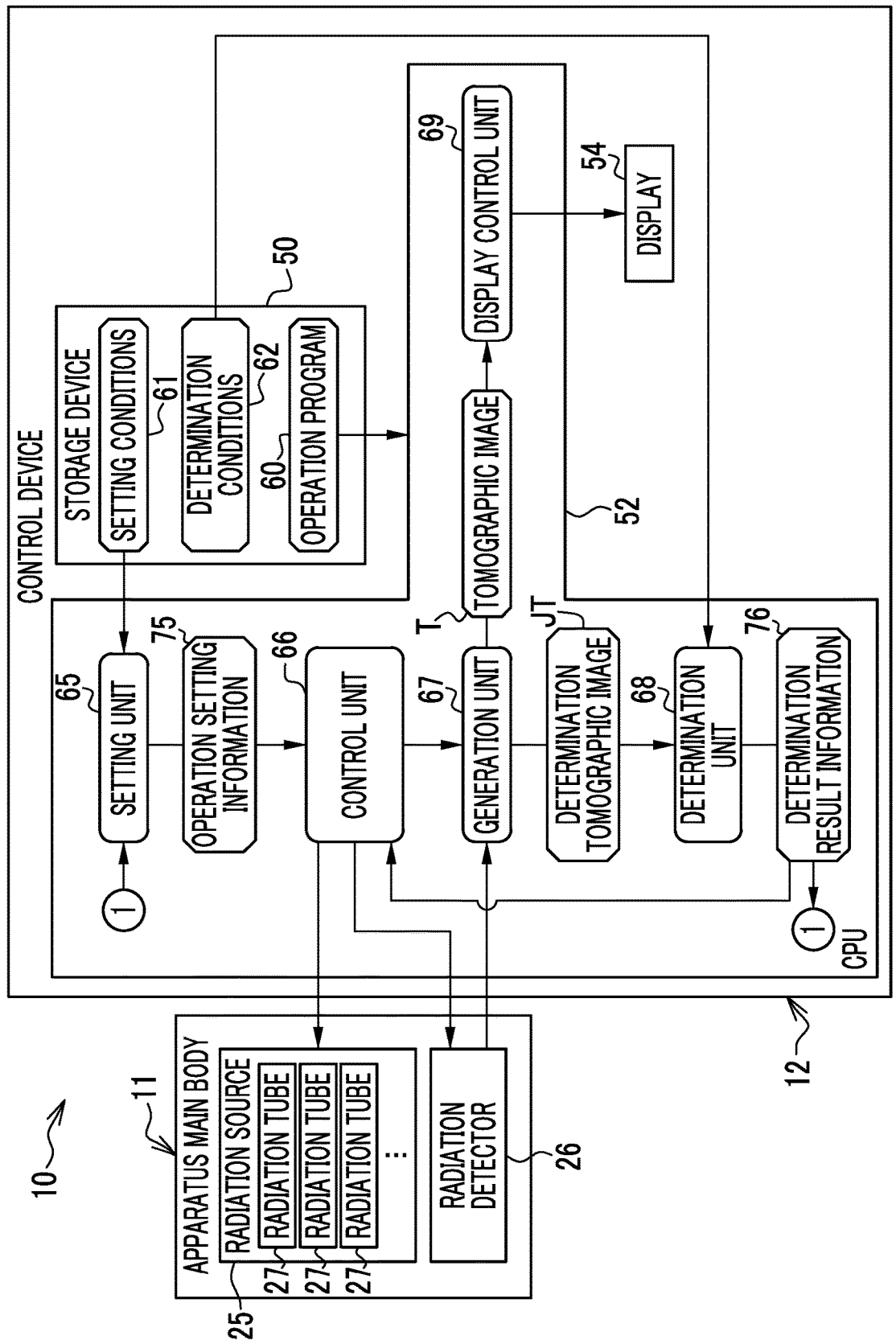
FIG. 10 is a block diagram mainly illustrating a processing unit of a CPU of the control device.

In FIG. 10, an operation program 60 is stored in the storage device 50 of the control device 12. The operation program 60 is an application program for causing the computer to function as the control device 12. That is, the operation program 60 is an example of a "program for operating a tomosynthesis imaging control device" according to the technology of the present disclosure. The storage device 50 stores setting conditions 61 and determination conditions 62 in addition to the operation program 60.

In a case in which the operation program 60 is started, the CPU 52 of the control device 12 functions as a setting unit 65, a control unit 66, a generation unit 67, a determination unit 68, and a display control unit 69 in cooperation with, for example, the memory 51.

The setting unit 65 sets the radiation tube 27 to be operated in the tomosynthesis imaging on the basis of the setting conditions 61. Specifically, the setting unit 65 sets a radiation tube 27 for emitting the radiation 37 among the radiation tubes 27 disposed at the irradiatable positions SP1 to SP15. The setting unit 65 sets a smaller number of radiation tubes 27 than the 15 radiation tubes 27. In this example, each radiation tube 27 is fixed at each of the irradiatable positions SP1 to SP15. Therefore, the "setting of the radiation tubes 27 for emitting the radiation 37 whose number is smaller than the total number of radiation tubes 27 among the radiation tubes 27" means the "setting of the irradiation positions whose number is smaller than the total number of irradiatable positions SP1 to SP15 among the irradiatable positions SP1 to SP15".

The mammography apparatus 10 performs a plurality of sets of tomosynthesis imaging operations. The setting unit 65 sets the radiation tube 27 for emitting the radiation 37 in each imaging set. The setting unit 65 outputs, to the control unit 66, information for uniquely identifying the set radiation tube 27, for example, operation setting information 75 in which radiation tube Identification data (ID) of the radiation tube 27 has been registered. In the radiation tube ID, numbers are linked to each of the irradiatable positions SP1 to SP15. For example, the radiation tube 27 disposed at the irradiatable position SP1 is represented by RT01, the radiation tube 27 disposed at the irradiatable position SP2 is represented by RT02, . . . , the radiation tube 27 disposed at the irradiatable position SP14 is represented by RT14, and the radiation tube 27 arranged at the irradiatable position SP15 is represented by RT15 (see FIG. 11).

The control unit 66 controls the operation of the radiation source 25 and the radiation detector 26. The control unit 66 receives the operation setting information 75 from the setting unit 65. The control unit 66 operates the radiation tube 27 with the radiation tube ID registered in the operation setting information 75 to emit the radiation 37. As described above, the radiation tube IDs of the radiation tubes 27 corresponding to the irradiation positions, whose number is smaller than the total number of irradiatable positions SP1 to SP15 and which have been set from the irradiatable positions SP1 to SP15, are registered in the operation setting information 75. Therefore, the "emission of the radiation 37 from the radiation tubes 27 with the radiation tube IDs registered in the operation setting information 75" means the "emission of the radiation 37 at the irradiation positions whose number is smaller than the total number of irradiatable positions". The control unit 66 outputs the projection image P detected by the radiation detector 26 by the emission of the radiation 37 at the irradiation position from the radiation detector 26 to the generation unit 67.

The generation unit 67 generates a determination tomographic image JT on the basis of the plurality of projection images P from the radiation detector 26 in each imaging set under the control of the control unit 66. The generation unit 67 outputs the determination tomographic image JT to the determination unit 68.

The determination unit 68 receives the determination tomographic image JT from the generation unit 67. The determination unit 68 determines whether or not the radiation 37 needs to be additionally emitted at the irradiatable positions different from the irradiation positions corresponding to the radiation tubes 27 set by the setting unit 65 in order to obtain a tomographic image T having an image quality level required for diagnosis, on the basis of the determination tomographic image JT and the determination conditions 62. The determination unit 68 uses one determination tomographic image JT in a representative tomographic plane, for example, an intermediate tomographic plane among the tomographic planes TF1 to TFN for determination. The determination unit 68 outputs, to the setting unit 65 and the control unit 66, determination result information 76 indicating the result of the determination of whether or not the radiation 37 needs to be additionally emitted at the irradiatable positions different from the irradiation positions.

In a case in which the determination unit 68 determines that the radiation 37 needs to be additionally emitted at the irradiatable positions different from the irradiation positions, the setting unit 65 sets an additional irradiation position among the different irradiatable positions. Specifically, the setting unit 65 sets a radiation tube 27 that additionally emits radiation among the radiation tubes 27 corresponding to the different irradiatable positions. The setting unit 65 outputs, to the control unit 66, operation setting information 75 in which the radiation tube ID of the radiation tube 27 that additionally emits radiation has been registered.

In a case in which the determination unit 68 determines that the radiation 37 needs to be additionally emitted at the irradiatable positions different from the irradiation positions, the control unit 66 operates the radiation tubes 27 that have been set to additionally emit radiation by the setting unit 65. Then, the control unit 66 directs the radiation tube to emit the radiation 37 at the additional irradiation position among the different irradiatable positions.

On the other hand, in a case in which the determination unit 68 determines that the radiation 37 does not need to be emitted at the irradiatable positions different from the irradiation positions, the control unit 66 ends the tomosynthesis imaging. In this case, the generation unit 67 outputs the determination tomographic image JT, on the basis of which the determination unit 68 determines that the radiation 37 does not need to be additionally emitted at the irradiatable positions different from the irradiation positions, as the tomographic image T to be provided for diagnosis to the display control unit 69.

The display control unit 69 receives the tomographic image T from the generation unit 67. The display control unit 69 performs control to generate an image display screen 90 (see FIG. 20) for displaying the received tomographic image T and to display the generated image display screen 90 on the display 54. The display control unit 69 performs control to display various screens on the display 54 in addition to the image display screen 90.

Figure 11:
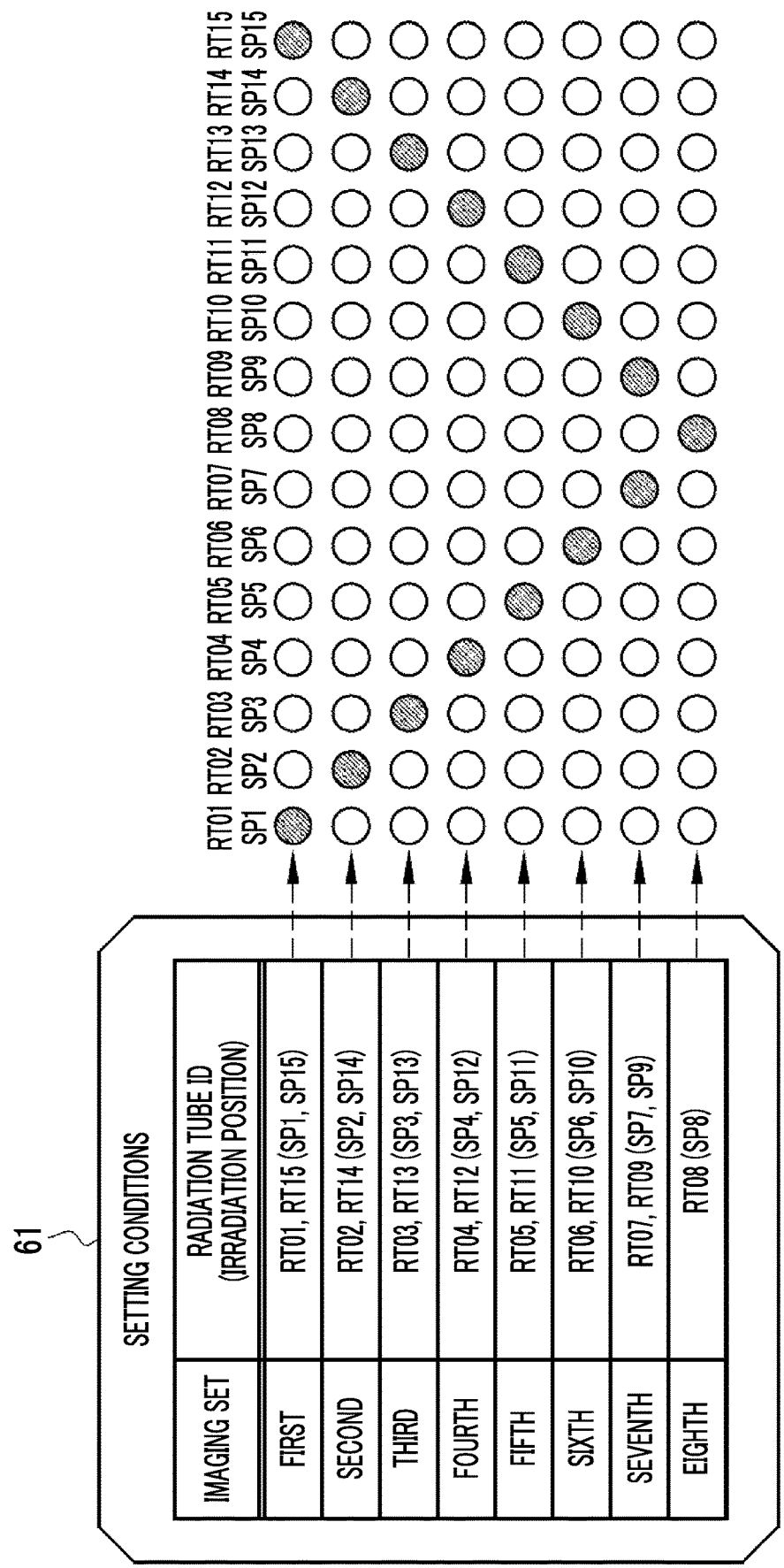
FIG. 11 is a diagram illustrating setting conditions.

In FIG. 11, the radiation tube IDs in each imaging set are registered in the setting conditions 61. In this example, the first to eighth imaging sets are provided. RT01 and RT15 are registered in the first imaging set, RT02 and RT14 are registered in the second imaging set, RT03 and RT13 are registered in the third imaging set, and RT04 and RT12 are registered in the fourth imaging set. Further, RT05 and RT11 are registered in the fifth imaging set, RT06 and RT10 are registered in the sixth imaging set, RT07 and RT09 are registered in the seventh imaging set, and RT08 is registered in the eighth imaging set. The irradiation positions corresponding to the radiation tubes 27 with the radiation tube IDs in the first imaging set are an example of "initial irradiation positions" according to the technology of the present disclosure. The irradiation positions corresponding to the radiation tubes 27 with the radiation tube IDs in the second to eighth imaging sets are examples of "additional irradiation positions" according to the technology of the present disclosure. In FIG. 11, for ease of understanding, the irradiation positions SP1 to SP15 are also illustrated and the radiation tube 27 that emits the radiation 37 in each imaging set is hatched in an illustration on the right side of a dashed arrow.

The irradiatable positions SP1 and SP15, the irradiatable positions SP2 and SP14, the irradiatable positions SP3 and SP13, the irradiatable positions SP4 and SP12, the irradiatable positions SP5 and SP11, the irradiatable positions SP6 and SP10, and the irradiatable positions SP7 and SP9 which are the irradiation positions corresponding to the radiation tubes 27 with the radiation tube IDs in each imaging set except the eighth imaging set are symmetric with respect to a line. That is, the irradiatable positions that are symmetric with respect to a line are set as the irradiation positions at a time.

The irradiatable positions SP1 and SP15 which are the irradiation positions in the first imaging set corresponding to the first irradiation positions are positions corresponding to the maximum irradiation angle. That is, positions corresponding to the maximum irradiation angle are set as the first irradiation positions.

Further, in the second to seventh imaging sets, the irradiation angle corresponding to the irradiation positions becomes smaller than that in the previous imaging set as the number of the imaging set becomes larger. That is, the irradiatable positions having a smaller irradiation angle than the irradiatable positions set in the previous imaging set are set as the additional irradiation positions.

Figure 12:
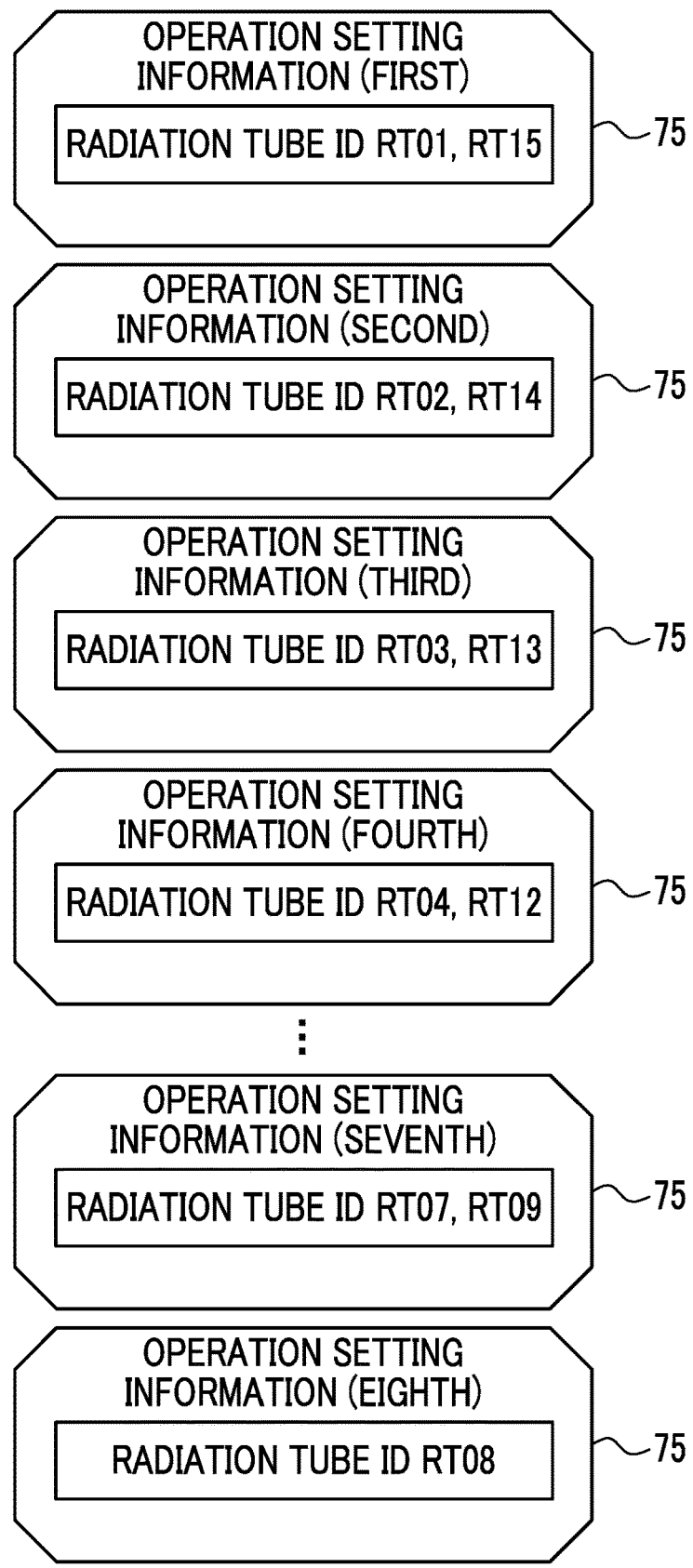
FIG. 12 is a diagram illustrating operation setting information.

FIG. 12 illustrates the operation setting information 75 in each imaging set in the case of the setting conditions 61 illustrated in FIG. 11. For example, in the operation setting information 75 in the third imaging set, RT03 and RT13 are registered as the radiation tube IDs. In this case, the control unit 66 operates the radiation tubes 27 with the radiation tube IDs RT03 and RT13 which are disposed at the irradiatable positions SP3 and SP13 to emit the radiation 37. In the operation setting information 75 in the seventh imaging set, RT07 and RT09 are registered as the radiation tube IDs. In this case, the control unit 66 operates the radiation tubes 27 with the radiation tube IDs RT07 and RT09 which are disposed at the irradiatable positions SP7 and SP9 to emit the radiation 37.

In FIG. 13, a table 80 illustrates the projection images P used by the generation unit 67 to generate the determination tomographic image JT in each imaging set. In the first imaging set, the generation unit 67 generates the determination tomographic image JT, using two projection images P obtained by the emission of the radiation 37 from the radiation tubes 27 with the radiation tube IDs RT01 and RT15 at the irradiatable positions SP1 and SP15. In the second imaging set, the generation unit 67 generates the determination tomographic image JT, using four projection images P obtained by the emission of the radiation 37 from the radiation tubes 27 with the radiation tube IDs RT02 and RT14 at the irradiatable positions SP2 and SP14 in addition to the irradiatable positions SP1 and SP15 in the first imaging set. Thereafter, the generation unit 67 generates the determination tomographic image JT, using the projection images P obtained by the emission of the radiation 37 at the previous irradiation positions and the current irradiation positions. Then, in the eighth imaging set, the generation unit 67 generates the determination tomographic image JT, using 15 projection images P obtained by the emission of the radiation 37 from all of the radiation tubes 27 with the radiation tube IDs RT01 to RT15 at all of the irradiatable positions SP1 to SP15.

Figure 14:
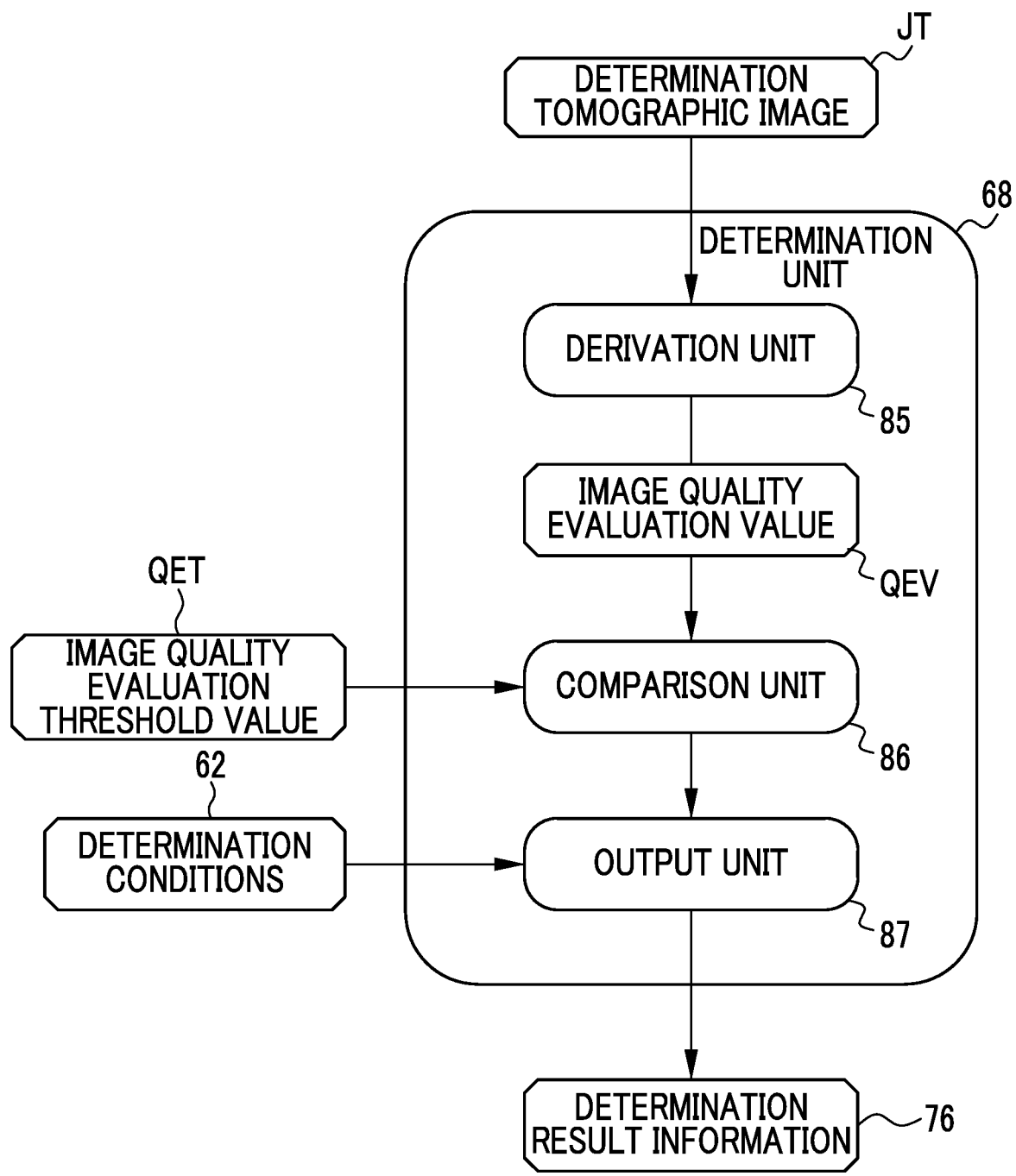
FIG. 14 is a diagram illustrating details of a determination unit.

In FIG. 14, the determination unit 68 includes a derivation unit 85, a comparison unit 86, and an output unit 87.

The derivation unit 85 derives an image quality evaluation value QEV indicating the quality of the determination tomographic image JT. The image quality evaluation value QEV is a signal-noise (SN) ratio which is one of an index indicating the granularity (which may be rephrased as the degree of roughness) and a half width of a point spread function (PSF) in a depth direction which is an index indicating the depth resolution of the determination tomographic image JT. For example, the derivation unit 85 divides the determination tomographic image JT into a plurality of regions, derives the image quality evaluation value QEV of each region, and calculates a representative value, such as an average value of the derived image quality evaluation values QEV of each region, as the image quality evaluation value QEV to be finally output. The derivation unit 85 outputs the derived image quality evaluation value QEV to the comparison unit 86.

The comparison unit 86 receives the image quality evaluation value QEV from the derivation unit 85. Further, the comparison unit 86 receives an image quality evaluation threshold value QET. The image quality evaluation threshold value QET is stored in the storage device 50 in advance, is read from the storage device 50, and is output to the comparison unit 86. The comparison unit 86 compares the image quality evaluation value QEV and the image quality evaluation threshold value QET and outputs the comparison result to the output unit 87.

The output unit 87 receives the comparison result from the comparison unit 86. The output unit 87 outputs determination result information 76 on the basis of the comparison result and the determination conditions 62.

Figure 15:
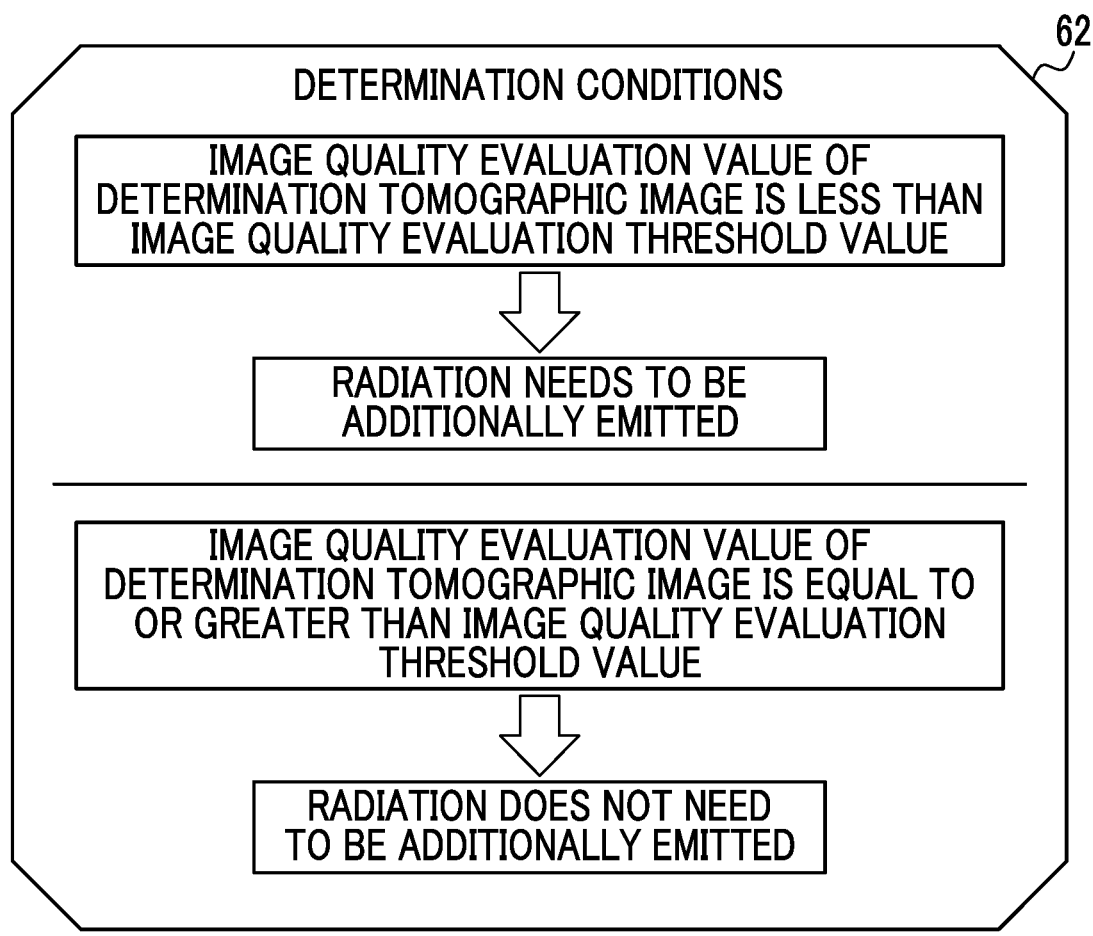
FIG. 15 is a diagram illustrating determination conditions.

In FIG. 15, the content of the determination conditions 62 is that, in a case in which the image quality evaluation value QEV of the determination tomographic image JT is less than the image quality evaluation threshold value QET, it is determined that the radiation 37 needs to be emitted at the irradiatable positions different from the irradiation positions. In this case, the output unit 87 outputs the determination result information 76 indicating that the radiation 37 needs to be emitted at the irradiatable positions different from the irradiation positions. In addition, the content of the determination conditions 62 is that, in a case in which the image quality evaluation value QEV of the determination tomographic image JT is equal to or greater than the image quality evaluation threshold value QET, it is determined that the radiation 37 does not need to be emitted at the irradiatable positions different from the irradiation positions. In this case, the output unit 87 outputs the determination result information 76 indicating that the radiation 37 does not need to be emitted at the irradiatable positions different from the irradiation positions.

The determination conditions 62 illustrated in FIG. 15 are an example in which, as the quality of the determination tomographic image JT becomes higher, the image quality evaluation value QEV becomes larger. In a case in which, as the quality of the determination tomographic image JT becomes higher, the image quality evaluation value QEV becomes smaller, the determination conditions 62 illustrated in FIG. 15 are reversed. That is, the content of the determination conditions 62 is that, in a case in which the image quality evaluation value QEV of the determination tomographic image JT is equal to or greater than the image quality evaluation threshold value QET, the radiation 37 needs to be emitted at the irradiatable positions different from the irradiation positions. In addition, the content of the determination conditions 62 is that, in a case in which the image quality evaluation value QEV of the determination tomographic image JT is less than the image quality evaluation threshold value QET, the radiation 37 does not need to be emitted at the irradiatable positions different from the irradiation positions.

Figure 16:
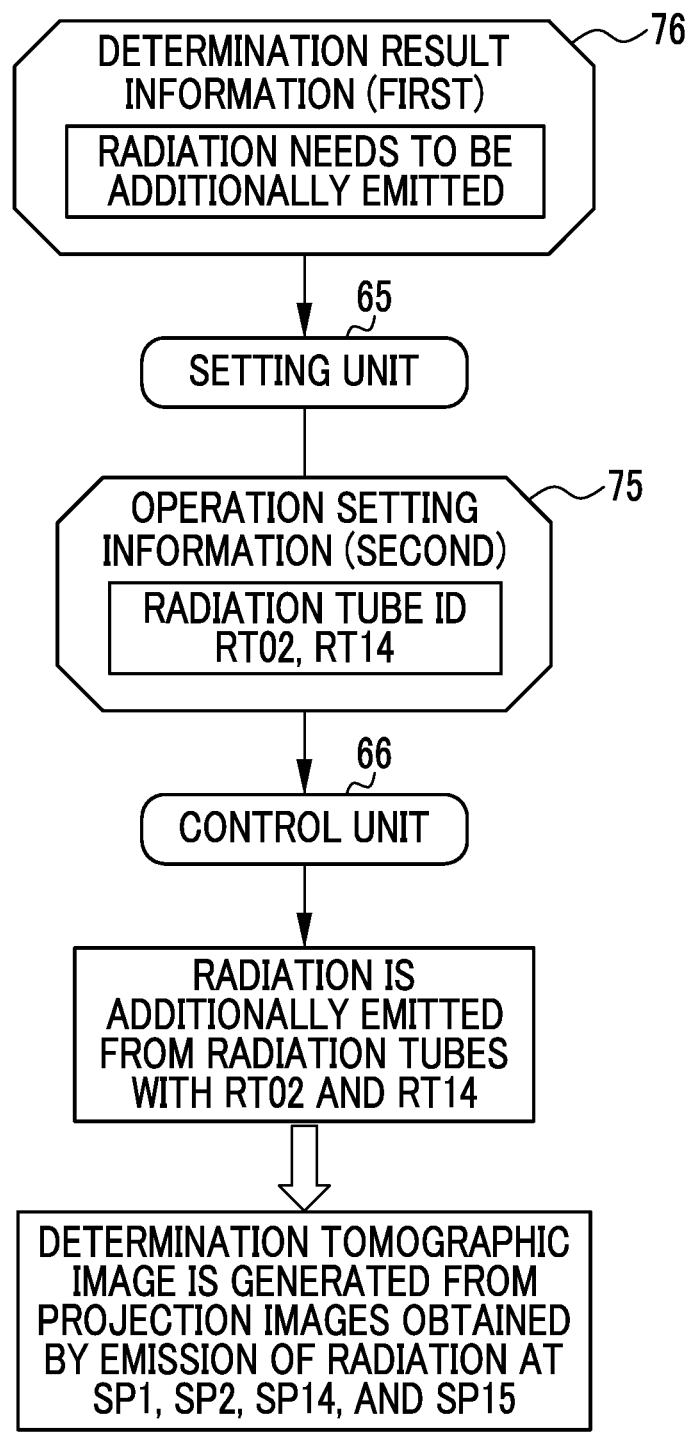
FIG. 16 is a diagram illustrating an example of determination result information and operation setting information.
Figure 17:
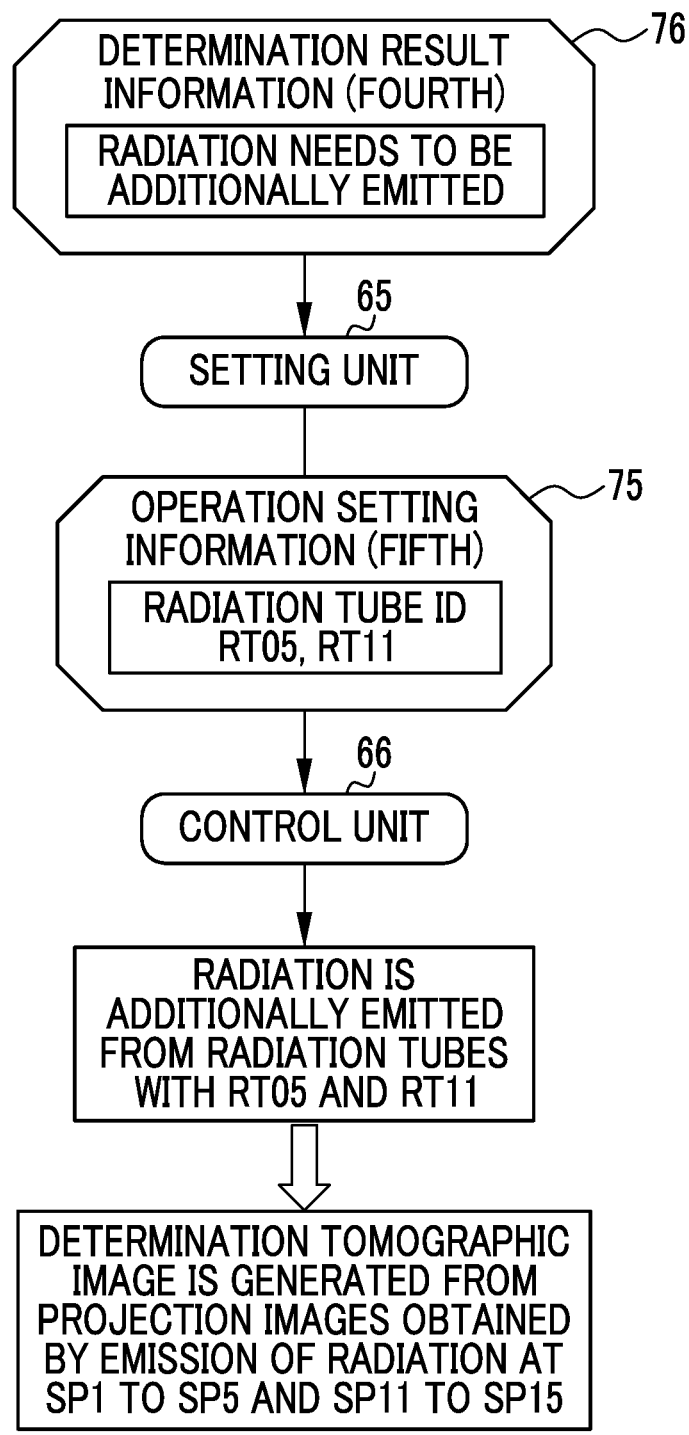
FIG. 17 is a diagram illustrating an example of determination result information and operation setting information.
Figure 18:
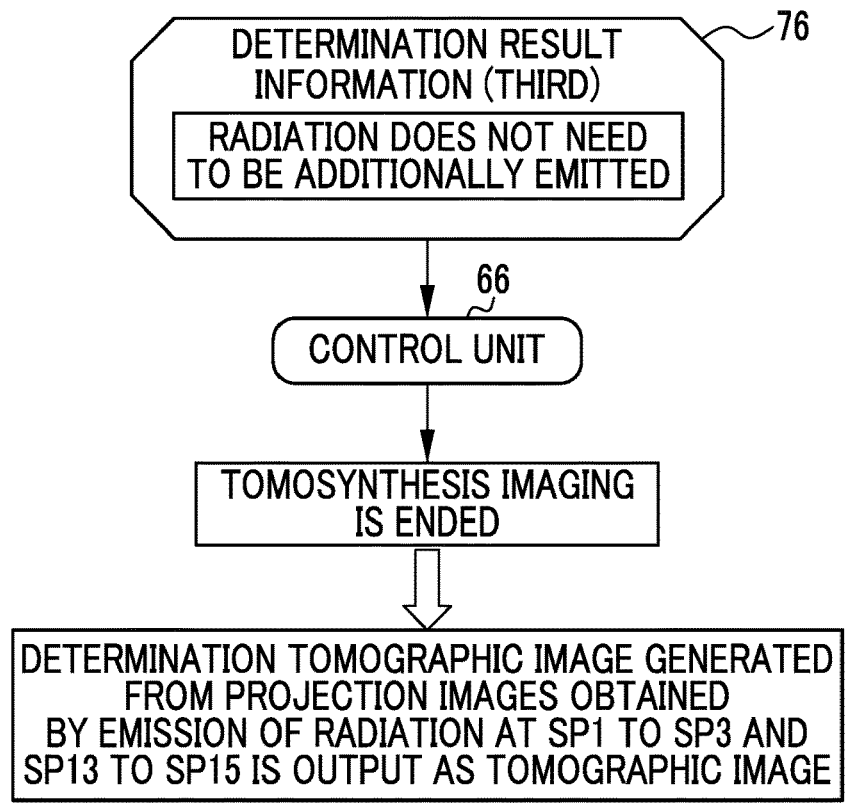
FIG. 18 is a diagram illustrating an example of determination result information.
Figure 19:
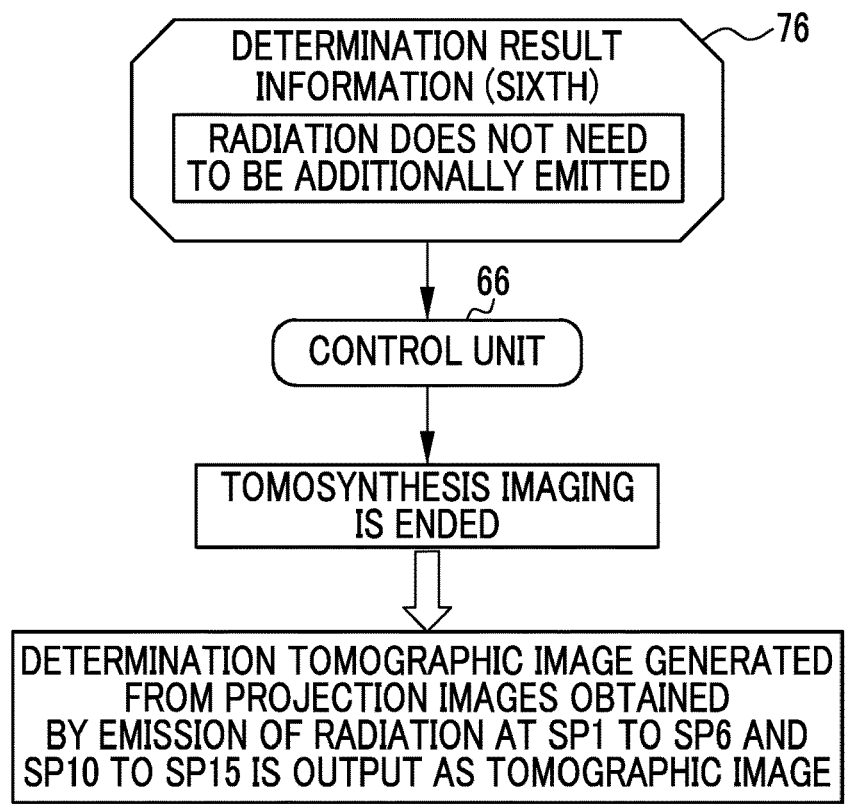
FIG. 19 is a diagram illustrating an example of determination result information.
Figure 20:
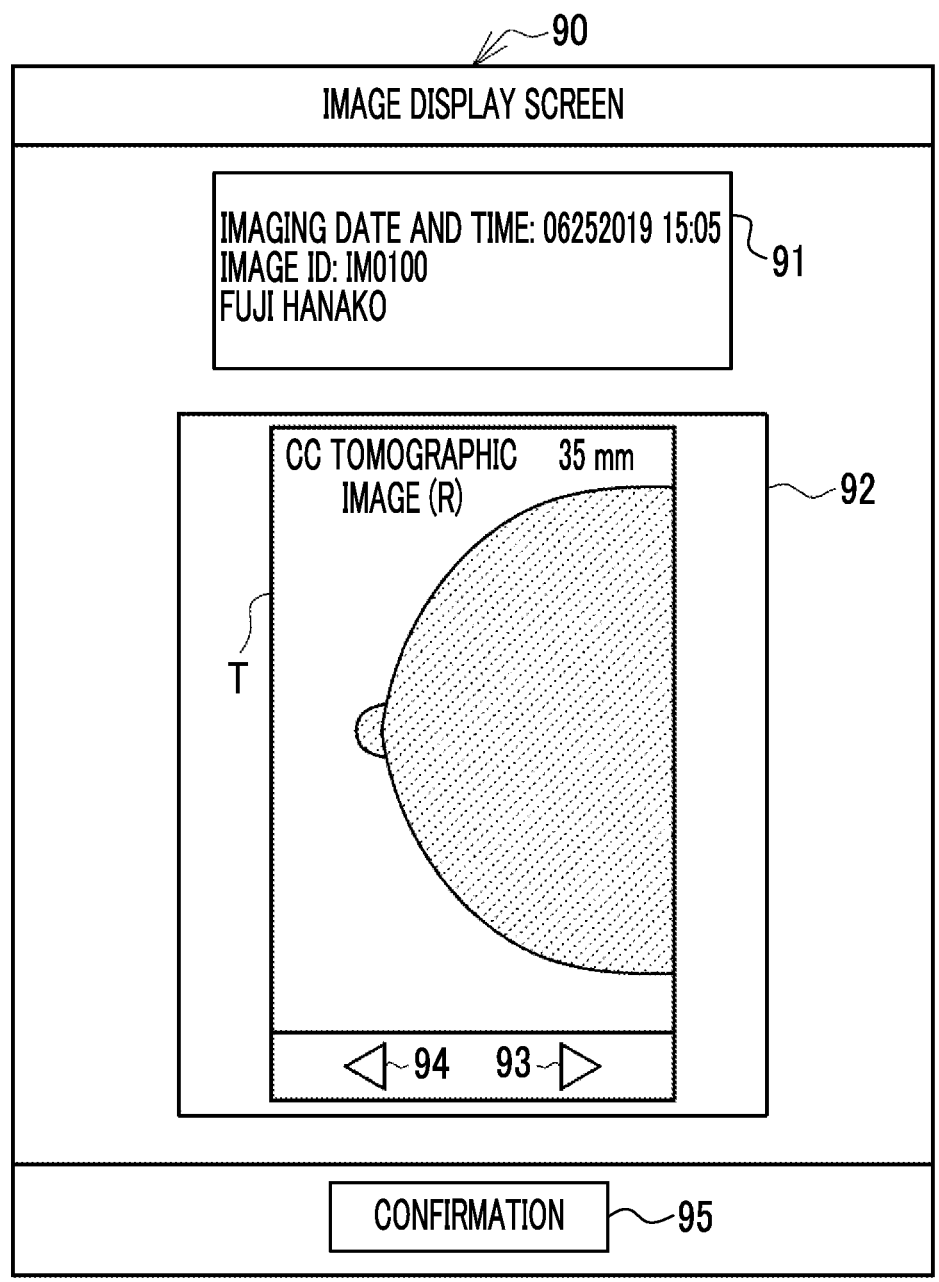
FIG. 20 is a diagram illustrating an image display screen.

FIGS. 16 to 19 illustrate various variations of the determination result information 76. FIGS. 16 and 17 illustrate a case in which the determination result information 76 indicating that the radiation 37 needs to be emitted at the irradiatable positions different from the irradiation positions. FIGS. 19 and 20 illustrate a case in which the determination result information 76 indicating that the radiation 37 does not need to be emitted at the irradiatable positions different from the irradiation positions.

FIG. 16 illustrates a case in which the determination result information 76 in the first imaging set indicates that the radiation 37 needs to be emitted at the irradiatable positions different from the irradiation positions. In this case, the setting unit 65 outputs the operation setting information 75 in the second imaging set in which RT02 and RT14 are set as the radiation tube IDs to the control unit 66. The control unit 66 operates the radiation tubes 27 with the radiation tube IDs RT02 and RT14 which are disposed at the irradiatable positions SP2 and SP14 to emit the radiation 37. The generation unit 67 generates the determination tomographic image JT from the projection images P obtained by the emission of the radiation 37 at the irradiatable positions SP1, SP2, SP14, and SP15.

FIG. 17 illustrates a case in which the determination result information 76 in the fourth imaging set indicates that the radiation 37 needs to be emitted at the irradiatable positions different from the irradiation positions. In this case, the setting unit 65 outputs, to the control unit 66, the operation setting information 75 in the fifth imaging set in which RT05 and RT11 are set as the radiation tube IDs. The control unit 66 operates the radiation tubes 27 with the radiation tube IDs RT05 and RT11 which are disposed at the irradiatable positions SP5 and SP11 to emit the radiation 37. The generation unit 67 generates the determination tomographic image JT from the projection images P obtained by the emission of the radiation 37 at the irradiatable positions SP1 to SP5 and SP11 to SP15.

FIG. 18 illustrates a case in which the determination result information 76 in the third imaging set indicating that the radiation 37 does not need to be emitted at the irradiatable positions different from the irradiation positions. In this case, the control unit 66 ends the tomosynthesis imaging. The generation unit 67 outputs the determination tomographic image JT generated from the projection images P obtained by the emission of the radiation 37 at the irradiatable positions SP1 to SP3 and SP13 to SP15 as the tomographic image T to the display control unit 69.

FIG. 19 illustrates a case in which the determination result information 76 in the sixth imaging set indicates that the radiation 37 does not need to be emitted at the irradiatable positions different from the irradiation positions. In this case, similarly to the case illustrated in FIG. 18, the control unit 66 ends the tomosynthesis imaging. The generation unit 67 outputs the determination tomographic image JT generated from the projection images P obtained by the emission of the radiation 37 at the irradiatable positions SP1 to SP6 and SP10 to SP15 as the tomographic image T to the display control unit 69.

In FIG. 20, the image display screen 90 displayed on the display 54 by the display control unit 69 is provided with an imaging information display region 91 and a tomographic image display region 92. Imaging information including an imaging date and time, an image ID for identifying the tomographic image T, and the name of the subject H is displayed in the imaging information display region 91. The tomographic image T is displayed in the tomographic image display region 92. FIG. 20 illustrates the tomographic image T obtained by the CC imaging. In the tomographic image T displayed in the tomographic image display region 92, a forward button 93 and a back button 94 provided in a lower part can be operated to switch the tomographic planes TF. The image display screen 90 is removed by the selection of a confirmation button 95.

Figure 21:
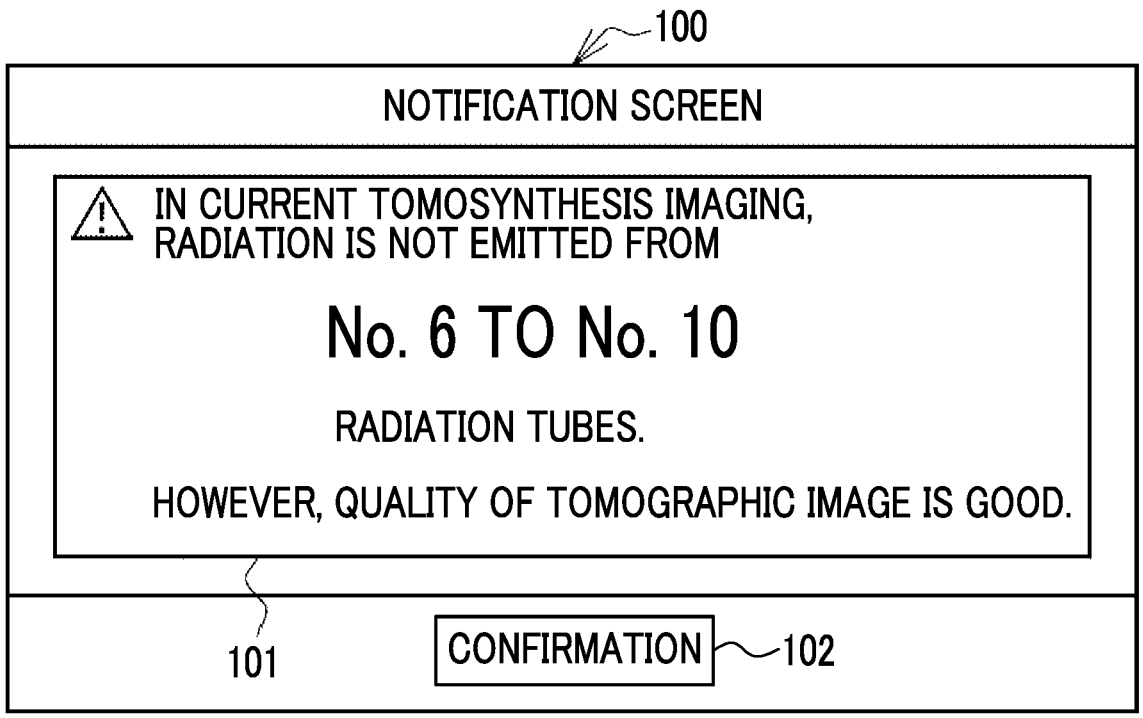
FIG. 21 is a diagram illustrating a notification screen for notifying that there is a radiation tube which has not emitted radiation.

A notification screen 100 illustrated in FIG. 21 is displayed on the display 54 by the display control unit 69 in a case in which there is a radiation tube 27 that has not emitted the radiation 37. In a case in which there is a radiation tube 27 that has not emitted the radiation 37, the determination unit 68 determines that the radiation 37 does not need to be emitted at the irradiatable positions different from the irradiation positions and the control unit 66 suspends the tomosynthesis imaging. The notification screen 100 is displayed so as to pop up on the image display screen 90. A message 101 indicating that there is a radiation tube 27 that has not emitted the radiation 37, but the quality of the tomographic image T is good is displayed on the notification screen 100. The notification screen 100 is removed by the selection of a confirmation button 102. FIG. 21 illustrates a case in which the tomosynthesis imaging is ended in the fifth imaging set and the radiation 37 is not emitted from the radiation tubes 27 with the radiation tube IDs RT06 to RT10 (represented by No. 6 to No. 10 in FIG. 21) in the sixth and subsequent imaging sets.

Figure 22:
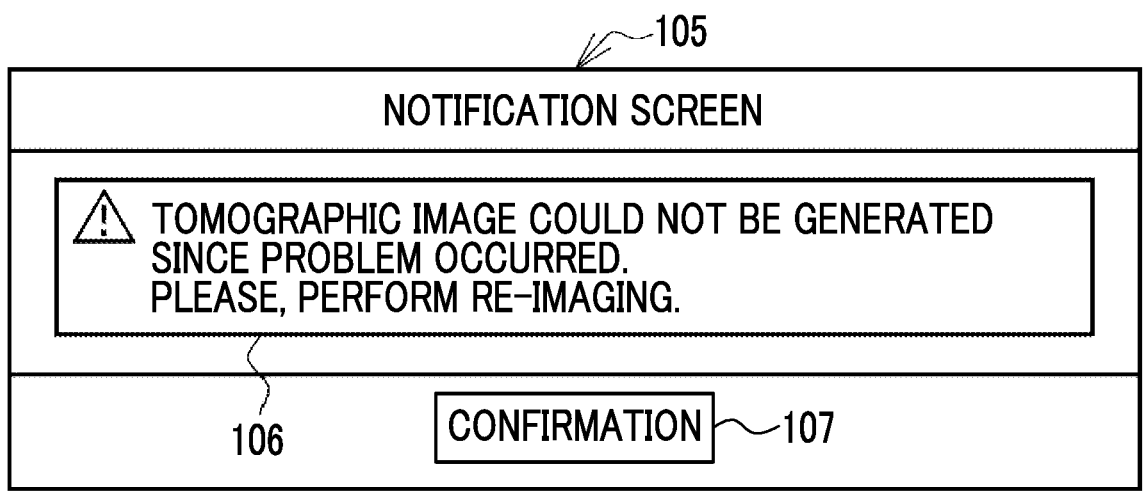
FIG. 22 is a diagram illustrating a notification screen for notifying that it is difficult to generate a tomographic image with an image quality level required for diagnosis.

A notification screen 105 illustrated in FIG. 22 is displayed on the display 54 by the display control unit 69 in a case in which the determination unit 68 determines that the radiation 37 needs to be emitted at the irradiatable positions different from the irradiation positions in the eighth imaging set. The notification screen 105 is displayed instead of the image display screen 90. A message 106 indicating that it is difficult to generate the tomographic image T having an image quality level required for diagnosis and a message for prompting re-imaging are displayed on the notification screen 105. The notification screen 105 is removed by the selection of a confirmation button 107.

The following is considered as a situation in which, in the eighth imaging set, the determination unit 68 determines that the radiation 37 needs to be emitted at the irradiatable positions different from the irradiation positions. For example, there is a case in which the quality of the projection image P and the determination tomographic image JT significantly deteriorates, for example, due to the movement of the breast M caused by the body movement of the subject H.

Figure 23:
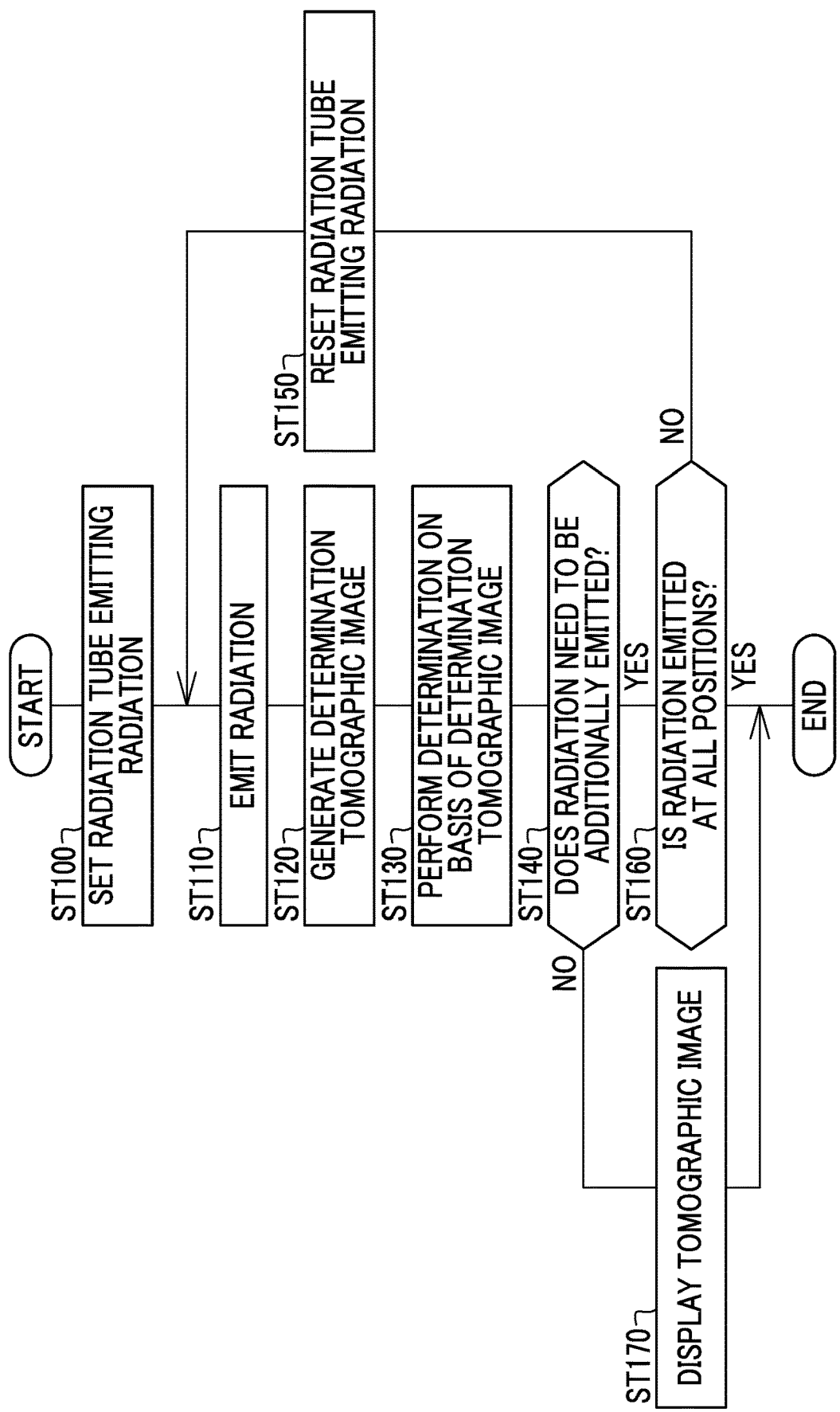
FIG. 23 is a flowchart illustrating a process procedure of the control device.

Next, the operation of the above-mentioned configuration will be described with reference to a flowchart illustrated in FIG. 23. In a case in which the operation program 60 is started, as illustrated in FIGS. 10 and 14, the CPU 52 of the control device 12 functions as the setting unit 65, the control unit 66, the generation unit 67, the determination unit 68 (the derivation unit 85, the comparison unit 86, and the output unit 87), and the display control unit 69.

First, as illustrated in Step ST100, the setting unit 65 sets the radiation tube 27 that emits the radiation 37 in the first imaging set on the basis of the setting conditions 61 illustrated in FIG. 11. Specifically, the setting unit 65 generates the operation setting information 75 of the first imaging set illustrated in FIG. 12. Then, the setting unit 65 outputs the generated operation setting information 75 to the control unit 66.

The control unit 66 operates the radiation tubes 27 with the radiation tube IDs RT01 and RT15 registered in the operation setting information 75 of the first imaging set to emit the radiation 37 (Step ST110). Then, the projection images P obtained by the emission of the radiation 37 at the irradiation positions are output from the radiation detector 26 to the generation unit 67. Step ST110 is an example of a "control step" according to the technology of the present disclosure.

As illustrated in the table 80 of FIG. 13, the generation unit 67 generates the determination tomographic image JT on the basis of the projection images P from the radiation detector 26 (Step ST120). The determination tomographic image JT is output from the generation unit 67 to the determination unit 68.

The determination unit 68 determines whether the radiation 37 needs to be additionally emitted at the irradiatable positions different from the irradiation positions, on the basis of the determination tomographic image JT and the determination conditions 62 illustrated in FIG. 15 (Step ST130). Specifically, as illustrated in FIG. 14, the derivation unit 85 derives the image quality evaluation value QEV of the determination tomographic image JT. Then, the comparison unit 86 compares the image quality evaluation value QEV with the image quality evaluation threshold value QET. Then, the output unit 87 generates the determination result information 76 corresponding to the result of the comparison between the image quality evaluation value QEV and the image quality evaluation threshold value QET. The determination result information 76 is output from the output unit 87 to the setting unit 65 and the control unit 66. Step ST130 is an example of a "determination step" according to the technology of the present disclosure.

In a case in which the determination unit 68 determines that the radiation 37 needs to be additionally emitted at the irradiatable positions different from the irradiation positions (YES in Step ST140), the setting unit 65 resets the radiation tubes 27 that additionally emit the radiation. (Step ST150). Specifically, as illustrated in FIG. 16, the operation setting information 75 of the second imaging set is generated by the setting unit 65 and is output to the control unit 66. Then, the process in Steps ST110 to ST130 is repeated.

The resetting of the radiation tubes 27 that additionally emit the radiation in Step ST150 and the repetition of the process in Steps ST110 to ST130 are continuously performed until the determination unit 68 determines that the radiation 37 does not need to be additionally emitted at the irradiatable positions different from the irradiation positions (NO in Step ST140) or until the radiation 37 is emitted at all of the irradiatable positions SP1 to SP15, that is, the eighth imaging set ends (YES in Step ST160) as illustrated in FIGS. 18 and 19.

In a case in which the determination unit 68 determines that the radiation 37 does not need to be additionally emitted at the irradiatable positions different from the irradiation positions (NO in Step ST140), the control unit 66 ends the tomosynthesis imaging. Then, the determination tomographic image JT on the basis of which the determination unit 68 determines that the radiation 37 does not need to be additionally emitted at the irradiatable positions different from the irradiation positions is output as the tomographic image T from the generation unit 67 to the display control unit 69.

The display control unit 69 displays the image display screen 90 illustrated in FIG. 20 on the display 54 and the tomographic image T is provided to the operator for browsing (Step ST170). In a case in which the control unit 66 suspends the tomosynthesis imaging and there is a radiation tube 27 that has not emitted the radiation 37, the notification screen 100 illustrated in FIG. 21 is displayed so as to pop up by the display control unit 69. Therefore, the operator is notified that there is a radiation tube 27 that has not emitted the radiation 37.

The display control unit 69 displays the notification screen 105 illustrated in FIG. 22 on the display 54 in a case in which the determination unit 68 determines that the radiation 37 needs to be additionally emitted at the irradiatable positions different from the irradiation positions (YES in Step ST140) and the radiation 37 has been emitted at all of the irradiatable positions SP1 to SP15, that is, the eighth imaging set has ended (YES in Step ST160). As a result, the operator is notified that it is difficult to generate the tomographic image T having an image quality level required for diagnosis and re-imaging is required.

As described above, the control device 12 comprises the control unit 66 and the determination unit 68. The control unit 66 controls the operation of the radiation tubes 27 such that the radiation 37 is emitted at the irradiation positions whose number is smaller than the total number of irradiatable positions. The determination unit 68 determines whether or not the radiation 37 needs to be additionally emitted at the irradiatable positions different from the irradiation positions in order to obtain the tomographic image T having an image quality level required for diagnosis, on the basis of the determination tomographic image JT obtained by the emission of the radiation 37 at the irradiation positions.

As described above, the control device 12 performs control such that the radiation 37 is not emitted from all of the irradiatable positions SP1 to SP15 at a time, but is emitted from the irradiation positions whose number is smaller than the total number of irradiatable positions SP1 to SP15 and verifies whether or not the tomographic image T having an image quality level required for diagnosis has been obtained. Then, the radiation 37 is additionally emitted until the tomographic image T having an image quality level required for diagnosis is obtained. Therefore, it is possible to prevent the quality of the tomographic image T from being over-specified or the quality of the tomographic image T from being lower than the level required for diagnosis. Further, since a plurality of radiation tubes 27 are used, the emission of the radiation 37 at the irradiation positions can be completed in a shorter time than that in the configuration according to the related art in which a radiation source includes one radiation tube is moved. Therefore, it is possible to obtain the tomographic image T having an image quality level required for diagnosis while preventing unnecessary exposure and an increase in imaging time.

For example, in a case in which so-called pre-imaging that emits the radiation 37 in order to recognize the state of the breast M is performed to determine the irradiation conditions of the main imaging, the radiographic image based on the radiation 37 emitted in the pre-imaging is not an image that is finally provided for diagnosis. Therefore, the radiation 37 emitted in the pre-imaging is wasted. In contrast, according to the technology of the present disclosure, the tomographic image T is generated from all of the projection images P obtained by the emission of the radiation 37 at the irradiation positions. Therefore, the emission of the radiation 37 at each irradiation position is not wasted.

In a case in which the determination unit 68 determines that the radiation 37 needs to be additionally emitted at the irradiatable positions different from the irradiation positions, the control unit 66 additionally emits the radiation at an additional irradiation position among the different irradiatable positions. Therefore, it is possible to additionally emit the radiation 37 at the additional irradiation position without bothering the operator. On the other hand, in a case in which the determination unit 68 determines that the radiation 37 does not need to be additionally emitted at the irradiatable positions different from the irradiation positions, the control unit 66 ends the tomosynthesis imaging. Therefore, it is possible to reliably prevent unnecessary exposure and to complete imaging in a short time.

The determination unit 68 performs determination, using the determination tomographic image JT generated from at least two projection images P obtained by the emission of the radiation 37 at least two irradiation positions as the determination image. Therefore, it is possible to ensure the validity of the determination result of the determination unit 68 determining whether or not the radiation 37 needs to be additionally emitted at the irradiatable positions different from the irradiation positions in order to obtain the tomographic image T having an image quality level required for diagnosis.

The determination unit 68 performs determination by comparing the image quality evaluation value QEV of the determination tomographic image JT with the preset image quality evaluation threshold value QET. Therefore, a determination logic is clear, and there is no room for doubt in the determination result.

The irradiatable positions that are symmetric with respect to a line are set as the irradiation positions at a time. Therefore, the obtained projection images P are also symmetric with respect to a line. Therefore, the process related to the generation of the determination tomographic image JT based on the projection images P can be simpler than that in a case in which the projection images P are not symmetric with respect to a line.

In addition, the irradiatable positions corresponding to the maximum irradiation angle are set as the first irradiation positions. The irradiatable positions corresponding to the maximum irradiation angle are positions related to the depth resolution of the tomographic image T. The depth resolution is the most important item in the quality of the tomographic image T. Therefore, in a case in which the irradiatable positions corresponding to the maximum irradiation angle are set as the first irradiation positions, first, it is possible to verify whether or not the depth resolution is at a level required for diagnosis.

Further, the irradiatable positions corresponding to a smaller irradiation angle than the previously set irradiation positions are set as the additional irradiation positions. The irradiatable positions corresponding to a small irradiation angle are positions related to the granularity of the tomographic image T. The granularity is an important item next to the depth resolution in the quality of the tomographic image T. Therefore, in a case in which the irradiatable positions corresponding to a smaller irradiation angle than the previously set irradiation positions are set as the additional irradiation positions, it is possible to gradually shift the verification of whether or not the image quality is at a level required for diagnosis from the depth resolution to the granularity.

The radiation tubes 27 are fixed at each of the irradiatable positions SP1 to SP15. Therefore, it takes no time to move the radiation tubes 27 and it is possible to further reduce the time required for imaging.

The determination tomographic image JT may be a plurality of tomographic images in a plurality of tomographic planes among all of the tomographic planes TF1 to TFN. In this case, the determination unit 68 performs the determination for each of a plurality of determination tomographic images JT, for example, 50 determination tomographic images JT. Then, the control unit 66 ends the tomosynthesis imaging in a case in which the determination result information 76 on a predetermined number of determination tomographic images JT or more, for example, 40 or more determination tomographic images JT among 50 determination tomographic images JT indicates that the radiation 37 does not need to be additionally emitted at the irradiatable positions different from the irradiation positions. Alternatively, the control unit 66 may end the tomosynthesis imaging in a case in which all of the determination result information 76 on a plurality of determination tomographic images JT indicates that the radiation 37 does not need to be additionally emitted at the irradiatable positions different from the irradiation positions.

The setting conditions are not limited to the setting conditions 61 illustrated in FIG. 11. For example, setting conditions 110 illustrated in FIG. 24 may be used.

Figure 24:
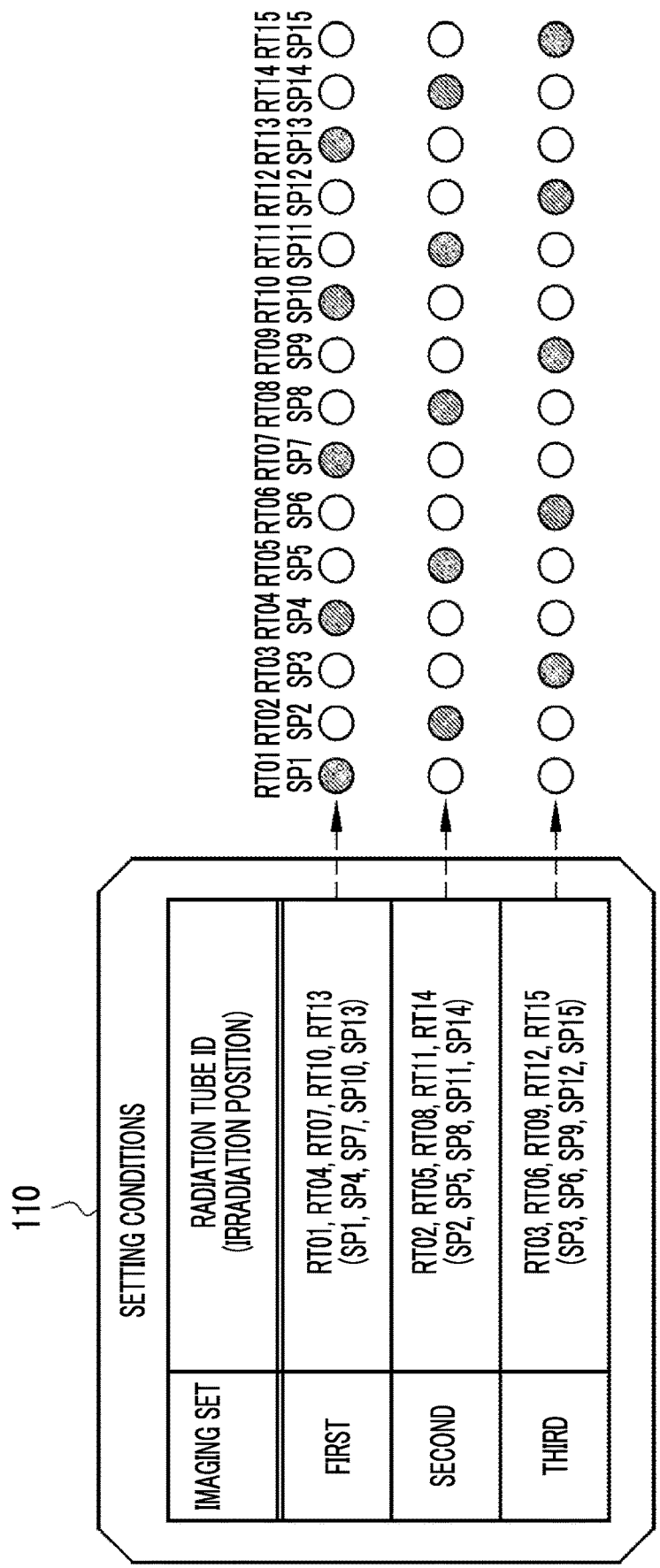
FIG. 24 is a diagram illustrating another example of the setting conditions.

In FIG. 24, the setting conditions 110 include first to third imaging sets. In the first imaging set, RT01, RT04, RT07, RT10, and RT13 are registered as the radiation tube IDs. In the second imaging set, RT02, RT05, RT08, RT11, and RT14 are registered. In the third imaging set, RT03, RT06, RT09, RT12, and RT15 are registered. In each of the imaging sets, every three positions that are arranged at equal intervals are the irradiation positions. That is, in the case of the setting conditions 110, the irradiation positions arranged at equal intervals are set at a time. In this case, as in the case in which the positions that are symmetric with respect to a line are set as the irradiation positions at a time, the irradiation positions have regularity. Therefore, it is possible to simplify the process related to the generation of the determination tomographic image JT based on the projection images P.

Second Embodiment

Attention is paid to a lesion, such as a calcified part or a tumor, in diagnosis using the tomographic image T. Therefore, in a second embodiment illustrated in FIGS. 25 and 26, the image quality evaluation value QEV is used as the value of a lesion.

Figure 25:
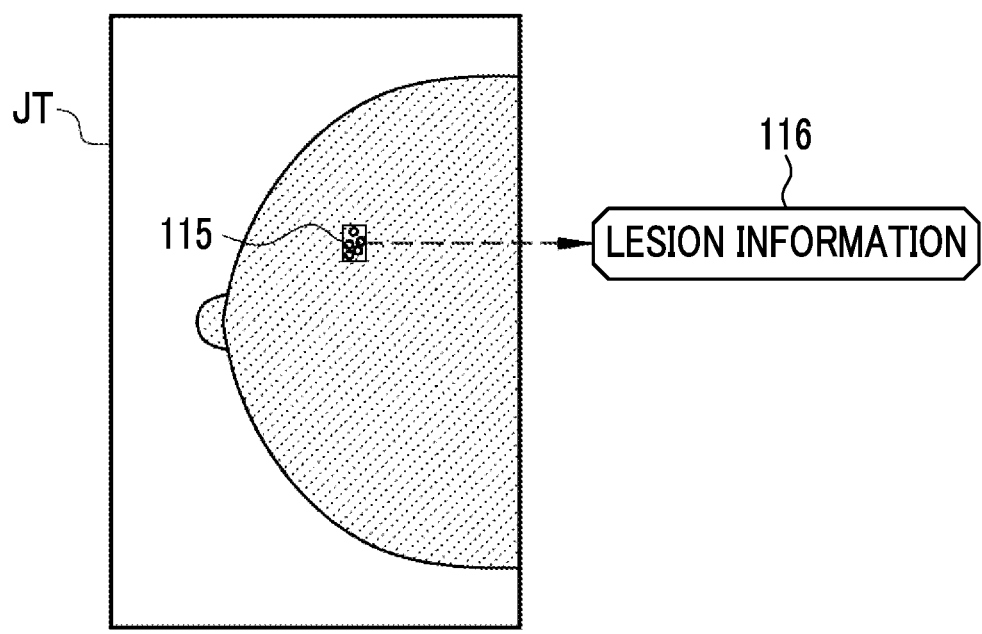
FIG. 25 is a conceptual diagram illustrating an aspect in which a lesion in a determination tomographic image is recognized and lesion information is output.

FIG. 25 is a conceptual diagram illustrating an aspect in which a lesion 115 in the determination tomographic image JT is recognized and lesion information 116 which is information related to the recognized lesion 115 is output. The lesion information 116 indicates the position coordinates of the lesion 115 in the determination tomographic image JT. In a case in which the lesion 115 is recognized as a rectangular region as illustrated in FIG. 25, the lesion information 116 is the position coordinates of each of four corners of the rectangle. The lesion 115 may be recognized by a well-known image recognition technology or diagnosis support technology or may be recognized by displaying the determination tomographic image JT on the display 54 and prompting the operator to designate the lesion 115. The lesion information 116 of the lesion 115 recognized in a case in which the tomosynthesis imaging is performed for the breast M of the same subject H may be used.

Figure 26:
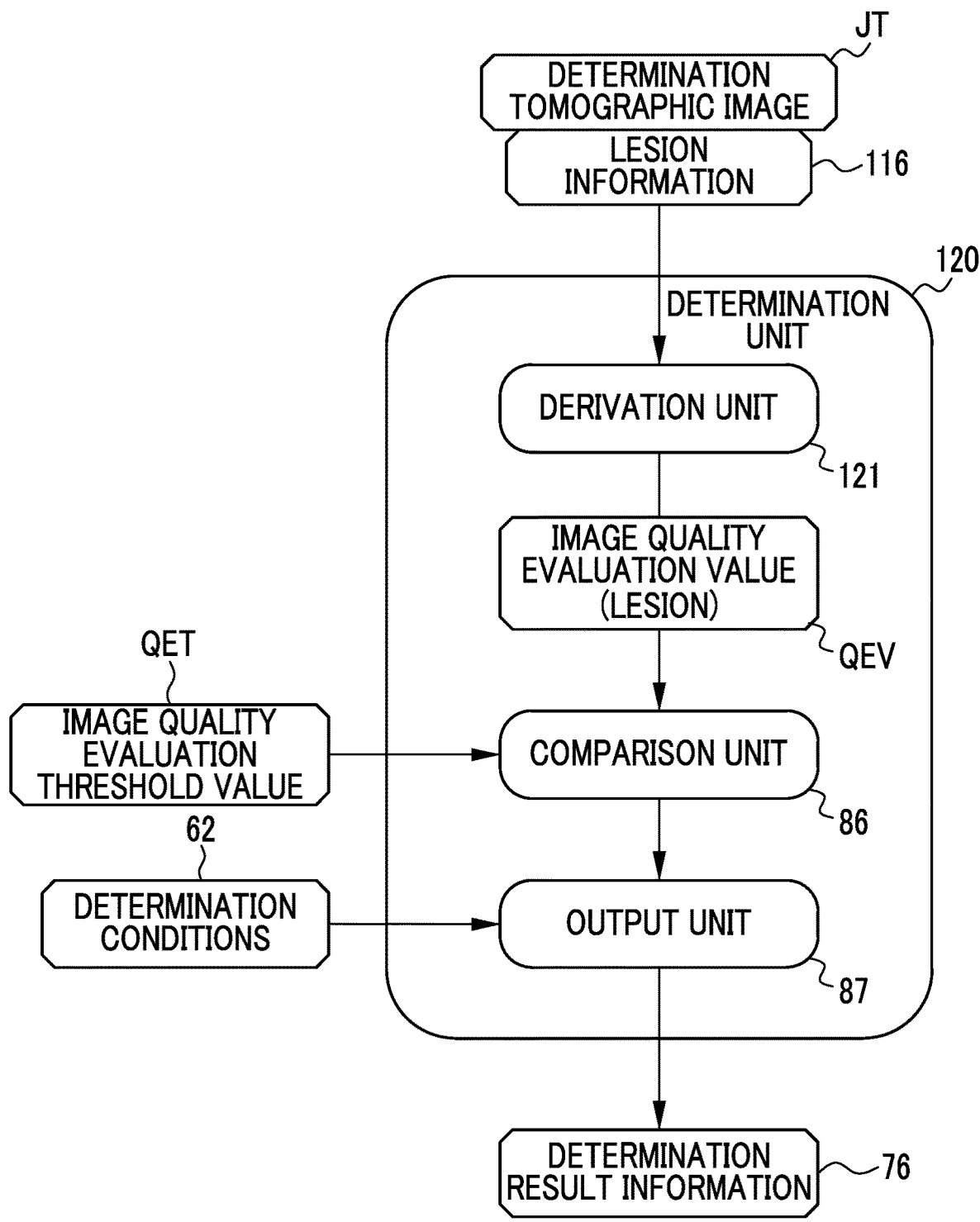
FIG. 26 is a diagram illustrating details of a determination unit according to a second embodiment.

In FIG. 26, a determination unit 120 according to the second embodiment has the same basic configuration as the determination unit 68 according to the first embodiment except the function of a derivation unit 121. Specifically, in addition to the determination tomographic image JT, the lesion information 116 is input to the derivation unit 121. The derivation unit 121 derives the image quality evaluation value QEV of the region of the lesion 115 registered in the lesion information 116. The subsequent processes are the same as those in the first embodiment and the description thereof will not be repeated.

As described above, in the second embodiment, the image quality evaluation value QEV is used as the value of the lesion 115. Therefore, the image quality of the lesion 115 to which attention is paid in diagnosis using the tomographic image T can be reliably set to a level required for the diagnosis. Further, the load of the process of deriving the image quality evaluation value QEV can be less than that in the first embodiment in which the entire determination tomographic image JT is a processing target.

In a case in which there are a plurality of lesions 115, the apparatus is configured such that the operator selects one of the plurality of lesions 115. Alternatively, it may be determined whether or not the radiation 37 needs to be additionally emitted at the irradiatable positions different from the irradiation positions for each of the plurality of lesions 115. In this configuration, the tomosynthesis imaging is continued in a case in which it is determined that the radiation 37 needs to be additionally emitted at the irradiatable positions different from the irradiation positions for any one of the plurality of lesions 115.

Third Embodiment

As described above, the quality of the tomographic image T mainly includes the granularity and the depth resolution. However, in each of the above-described embodiments, these items are simply collectively evaluated as "image quality" without discrimination. Therefore, in the third embodiment illustrated in FIGS. 27 to 30, whether or not the granularity of the determination tomographic image JT is at a level required for diagnosis and whether or not the depth resolution of the determination tomographic image JT is at a level required for diagnosis are individually determined.

Figure 27:
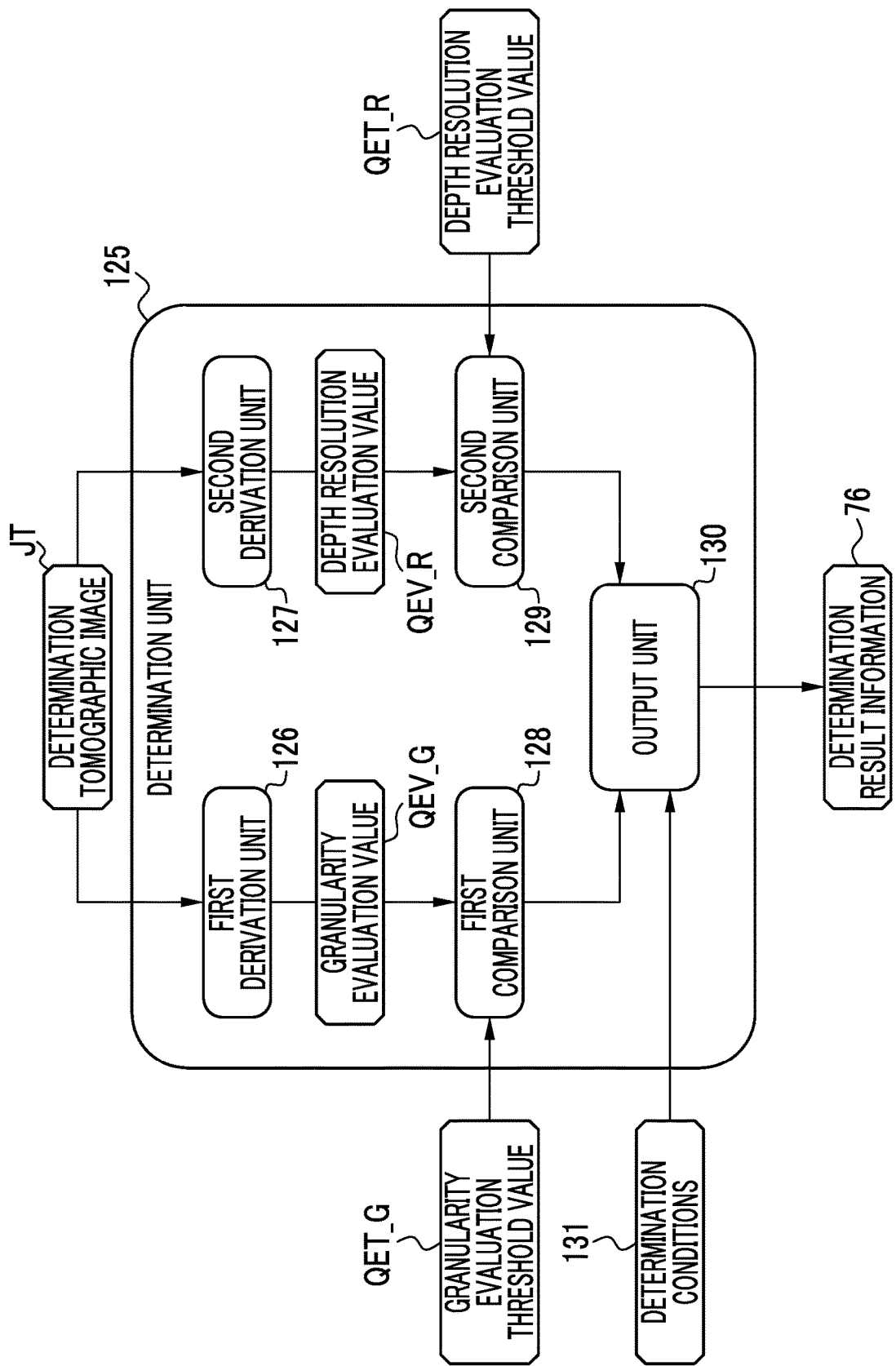
FIG. 27 is a diagram illustrating details of a determination unit according to a third embodiment.

In FIG. 27, a determination unit 125 according to the third embodiment includes a first derivation unit 126, a second derivation unit 127, a first comparison unit 128, a second comparison unit 129, and an output unit 130.

The first derivation unit 126 derives a granularity evaluation value QEV_G indicating the granularity of the determination tomographic image JT. The granularity evaluation value QEV_G is, for example, an SN ratio. The second derivation unit 127 derives a resolution evaluation value QEV_R indicating the depth resolution of the determination tomographic image JT. The depth resolution evaluation value QEV_R is, for example, a half width of a point spread function in the depth direction. For example, the first derivation unit 126 and the second derivation unit 127 divide the determination tomographic image JT into a plurality of equal regions and derive the granularity evaluation value QEV_G and the depth resolution evaluation value QEV_R for each region, similarly to the derivation unit 85 according to the first embodiment. Then, representative values, such as the average values of the derived granularity evaluation values QEV_G and the derived depth resolution evaluation values QEV_R of each region, are used as the granularity evaluation value QEV_G and the depth resolution evaluation value QEV_R that are finally output. The first derivation unit 126 outputs the derived granularity evaluation value QEV_G to the first comparison unit 128. The second derivation unit 127 outputs the derived depth resolution evaluation value QEV_R to the second comparison unit 129.

The first comparison unit 128 receives the granularity evaluation value QEV_G from the first derivation unit 126. Further, the first comparison unit 128 receives a granularity evaluation threshold value QET_G. The granularity evaluation threshold value QET_G is stored in the storage device 50 in advance, is read from the storage device 50, and is output to the first comparison unit 128. The first comparison unit 128 compares the granularity evaluation value QEV_G with the granularity evaluation threshold value QET_G and outputs the comparison result to the output unit 130.

The second comparison unit 129 receives the depth resolution evaluation value QEV_R from the second derivation unit 127. Further, the second comparison unit 129 receives a depth resolution evaluation threshold value QET_R. Similarity to the granularity evaluation threshold value QET_G, the depth resolution evaluation threshold value QET_R is stored in the storage device 50 in advance, is read from the storage device 50, and is output to the second comparison unit 129. The second comparison unit 129 compares the depth resolution evaluation value QEV_R with the depth resolution evaluation threshold value QET_R and outputs the comparison result to the output unit 130.

The output unit 130 receives the comparison results from the first comparison unit 128 and the second comparison unit 129. The output unit 130 outputs determination result information 76 on the basis of the comparison results of the first comparison unit 128 and the second comparison unit 129 and determination conditions 131.

In FIG. 28, the content of the determination conditions 131 is that, in a case in which the granularity evaluation value QEV_G of the determination tomographic image JT is less than the granularity evaluation threshold value QET_G or in a case in which the depth resolution evaluation value QEV_R of the determination tomographic image JT is less than the depth resolution evaluation threshold value QET_R, it is determined that the radiation 37 needs to be emitted at the irradiatable positions different from the irradiation positions. In this case, the output unit 130 outputs the determination result information 76 indicating that the radiation 37 needs to be emitted at the irradiatable positions different from the irradiation positions (see FIGS. 30A to 30C). In addition, the content of the determination conditions 131 is that, in a case in which the granularity evaluation value QEV_G of the determination tomographic image JT is equal to or greater than the granularity evaluation threshold value QET_G and in a case in which the depth resolution evaluation value QEV_R of the determination tomographic image JT is equal to or greater than the depth resolution evaluation threshold value QET_R, it is determined that the radiation 37 does not need to be emitted at the irradiatable positions different from the irradiation positions. In this case, the output unit 130 outputs the determination result information 76 indicating that the radiation 37 does not need to be emitted at the irradiatable positions different from the irradiation positions (see FIG. 30D). That is, both the granularity and the depth resolution of the determination tomographic image JT need to reach the level required for diagnosis in order to determine that the radiation 37 does not need to be emitted.

In FIG. 29, only the first imaging set is registered in setting conditions 133 according to the third embodiment. That is, RT04 and RT12 are registered as the radiation tube IDs.

FIGS. 30A to 30D illustrate variations in the first imaging set according to the third embodiment. FIGS. 30A to 30C illustrate the case of the determination result information 76 indicating that the radiation 37 needs to be emitted at the irradiatable positions different from the irradiation positions. In contrast, FIG. 30D illustrates the case of the determination result information 76 indicating that the radiation 37 does not need to be emitted at the irradiatable positions different from the irradiation positions.

FIG. 30A illustrates a case in which the granularity evaluation value QEV_G of the determination tomographic image JT is less than the granularity evaluation threshold value QET_G and the depth resolution evaluation value QEV_R of the determination tomographic image JT is equal to or greater than the depth resolution evaluation threshold value QET_R. In other words, the depth resolution of the determination tomographic image JT is at the level required for diagnosis and the granularity thereof is not at the level required for diagnosis. In this case, the setting unit 135 according to the third embodiment outputs, to the control unit 66, the operation setting information 75 of the second imaging set in which RT06 and RT10 are set as the radiation tube IDs.

FIG. 30B illustrates a case in which the granularity evaluation value QEV_G of the determination tomographic image JT is equal to or greater than the granularity evaluation threshold value QET_G and the depth resolution evaluation value QEV_R of the determination tomographic image JT is less than the depth resolution evaluation threshold value QET_R. In other words, the granularity of the determination tomographic image JT is at the level required for diagnosis and the depth resolution is not at the level required for diagnosis. In this case, the setting unit 135 outputs, to the control unit 66, the operation setting information 75 of the second imaging set in which RT01 and RT15 are set as the radiation tube IDs.

FIG. 30C illustrates a case in which the granularity evaluation value QEV_G of the determination tomographic image JT is less than the granularity evaluation threshold value QET_G and the depth resolution evaluation value QEV_R of the determination tomographic image JT is less than the depth resolution evaluation threshold value QET_R. In other words, the granularity and the depth resolution of the determination tomographic image JT are not at the levels required for diagnosis. In this case, the setting unit 135 outputs, to the control unit 66, the operation setting information 75 of the second imaging set in which RT01, RT06, RT10, and RT15 are set as the radiation tube IDs.

FIG. 30D illustrates a case in which the granularity evaluation value QEV_G of the determination tomographic image JT is equal to or greater than the granularity evaluation threshold value QET_G and the depth resolution evaluation value QEV_R of the determination tomographic image JT is equal to or greater than the depth resolution evaluation threshold value QET_R. In this case, since the control unit 66 ends the tomosynthesis imaging, the setting unit 135 does not output the operation setting information 75.

The irradiatable positions SP6 and SP10 corresponding to the radiation tubes 27 with the radiation tube IDs RT06 and RT10 have a smaller irradiation angle than the irradiatable positions SP1 and SP15 corresponding to the radiation tubes 27 with the radiation tube IDs RT01 and RT15 and are related to the granularity of the tomographic image T. Therefore, in the case of FIGS. 30A and 30C in which the granularity is not at the level required for diagnosis, the setting unit 135 sets RT06 and RT10 which are the radiation tube IDs of the radiation tubes 27 corresponding to the irradiatable positions SP6 and SP10. In contrast, the irradiatable positions SP1 and SP15 are irradiatable positions corresponding to the maximum irradiation angle as described above and are related to the depth resolution of the tomographic image T. Therefore, in the case of FIGS. 30B and 30C in which the depth resolution is not at the level required for diagnosis, the setting unit 65 sets RT01 and RT15 which are the radiation tube IDs of the radiation tubes 27 corresponding to the irradiatable positions SP1 and SP15.

As described above, in the third embodiment, the determination unit 125 individually determines whether or not the granularity of the determination tomographic image JT is at the level required for diagnosis and whether or not the depth resolution of the determination tomographic image JT is at the level required for diagnosis. Then, the additional irradiation position is changed according to the determination result of the determination unit 125. Specifically, in a case in which the depth resolution is at the level required for diagnosis, but the granularity is not at the level required for diagnosis, the irradiatable positions having a relatively small irradiation angle are set as the additional irradiation positions. In a case in which the granularity is at the level required for diagnosis, but the depth resolution is not at the level required for diagnosis, the irradiatable positions having a relatively large irradiation angle, for example, the irradiatable positions corresponding to the maximum irradiation angle are set as the additional irradiation positions. In a case in which the granularity and the depth resolution are not at the levels required for diagnosis, both the irradiatable positions having a relatively small irradiation angle and the irradiatable positions having a relatively large irradiation angle are set as the additional irradiation positions. Therefore, in the next imaging set, there is a high possibility that it will be determined that the radiation 37 does not need to be additionally emitted at the irradiatable positions different from the irradiation positions. Therefore, this configuration can contribute to shortening the imaging time and reducing unnecessary exposure.

In addition, the second embodiment may be applied to derive the granularity evaluation value QEV_G and the depth resolution evaluation value QEV_R of the lesion 115.

Fourth Embodiment

In the above-described embodiments, the determination is performed on the basis of the image quality evaluation value QEV (including the granularity evaluation value QEV_G and the depth resolution evaluation value QEV_R). However, in a fourth embodiment illustrated in FIGS. 31 to 34, the determination is performed using a first machine learning model 143.

Figure 31:
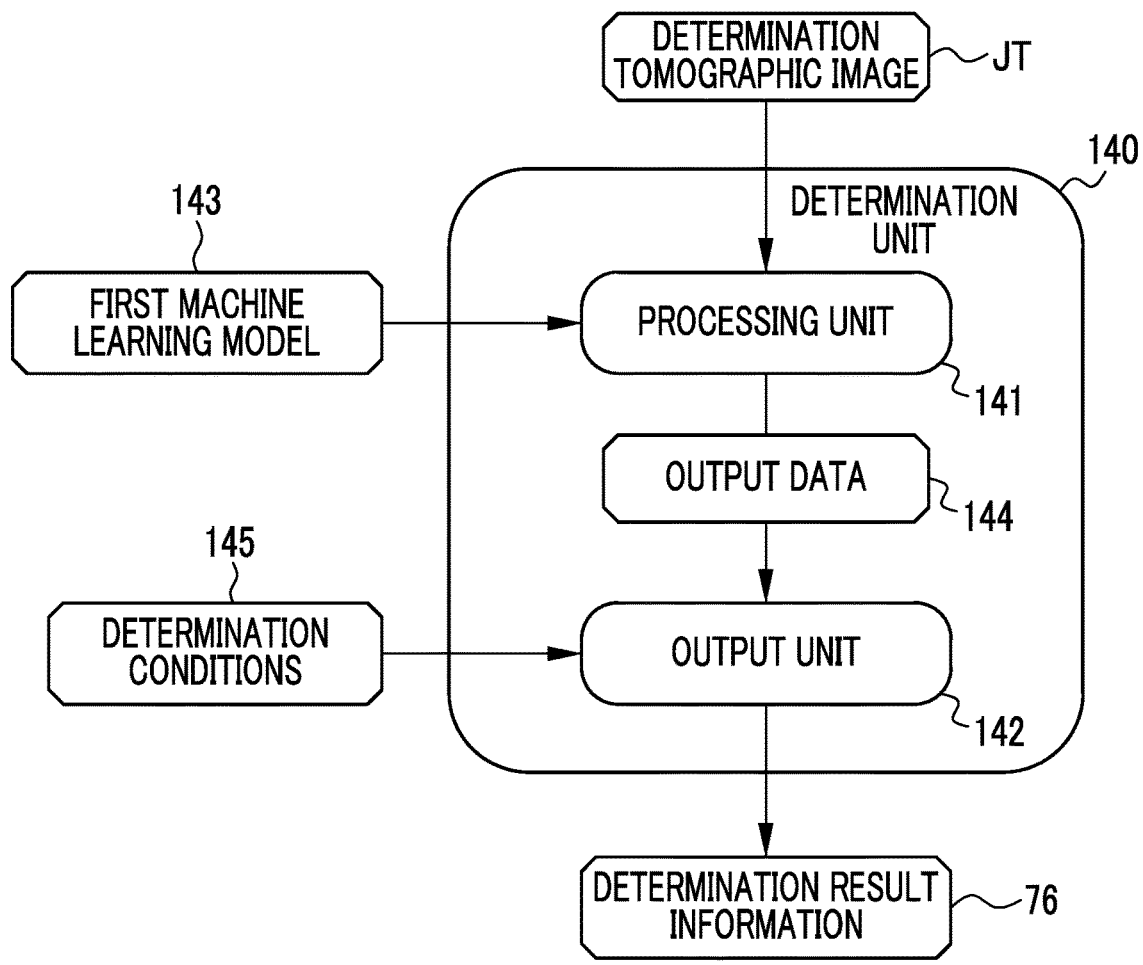
FIG. 31 is a diagram illustrating details of a determination unit according to a fourth embodiment.

In FIG. 31, a determination unit 140 according to the fourth embodiment includes a processing unit 141 and an output unit 142. The processing unit 141 inputs the determination tomographic image JT to the first machine learning model 143 and directs the first machine learning model 143 to output output data 144. The processing unit 141 outputs the output data 144 to the output unit 142. The output data 144 indicates whether or not the quality of the determination tomographic image JT is at a level required for diagnosis (see FIG. 33). The output unit 142 outputs determination result information 76 on the basis of the output data 144 and determination conditions 145.

Figure 32:
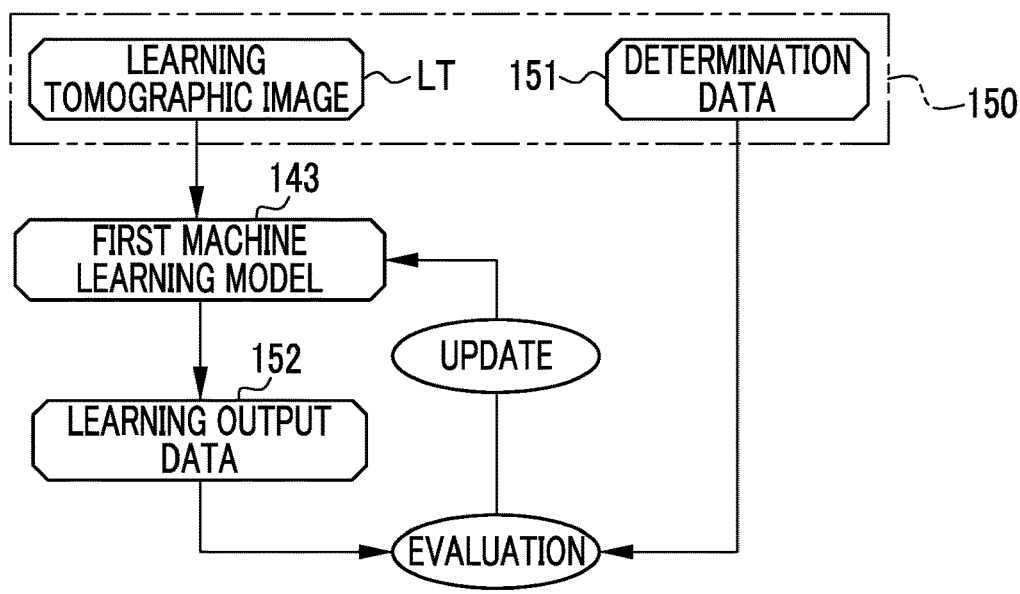
FIG. 32 is a diagram illustrating a process in a learning phase of a first machine learning model.

FIG. 32 illustrates a process in the learning phase of the first machine learning model 143. The first machine learning model 143 is trained using learning data 150. The learning data 150 includes a set of a learning tomographic image LT and determination data 151. The learning tomographic image LT is literally a tomographic image for training the first machine learning model 143. There is a learning tomographic image LT including a lesion 115. In addition, there is a learning tomographic image LT without including the lesion 115. The determination data 151 is data used by, for example, the operator to determine whether or not the quality of the learning tomographic image LT is at a level required for diagnosis.

In the learning phase, the learning tomographic image LT is input to the first machine learning model 143. As a result, learning output data 152 is output from the first machine learning model 143. Similarly to the output data 144, the learning output data 152 indicates whether or not the quality of the learning tomographic image LT is at a level required for diagnosis.

The determination data 151 is data for matching with the learning output data 152. In the learning phase, the determination data 151 and the learning output data 152 are used to evaluate the prediction accuracy of the first machine learning model 143.

In a case in which the content of the determination data 151 is matched with the content of the learning output data 152, it is evaluated that the prediction of the first machine learning model 143 is correct. In this case, parameters of the first machine learning model 143 are not updated. The content of the determination data 151 is not matched with the content of the learning output data 152 in the following two cases. That is, both the determination data 151 and the learning output data 152 indicate that the quality of the learning tomographic image LT are at the levels required for diagnosis and both the determination data 151 and the learning output data 152 indicate that the quality of the learning tomographic image LT are not at the levels required for diagnosis.

In contrast, in a case in which the content of the determination data 151 is not matched with the content of the learning output data 152, it is evaluated that the prediction of the first machine learning model 143 is wrong. In this case, the parameters of the first machine learning model 143 are updated to increase the prediction accuracy.

In the learning phase, the input of the learning tomographic image LT to the first machine learning model 143, the output of the learning output data 152 from the first machine learning model 143, the evaluation of the prediction accuracy of the first machine learning model 143 using the determination data 151 and the learning output data 152, and the update of the parameters of the first machine learning model 143 are repeated while the learning data 150 is changed. Therefore, in the learning phase, the prediction accuracy of the first machine learning model 143 is increased. Then, the first machine learning model 143 whose prediction accuracy has reached a preset level or higher is provided to the processing unit 141. The number of learning tomographic images LT including the lesion 115 may be larger than the number of learning tomographic images LT without including the lesion 115 such that the learning tomographic image LT including the lesion 115 is mainly learned.

Figure 33A:
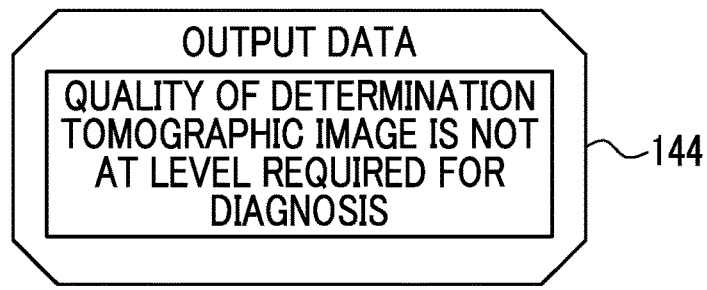
FIGS. 33A and 33B are diagrams illustrating output data from the first machine learning model.
Figure 33B:
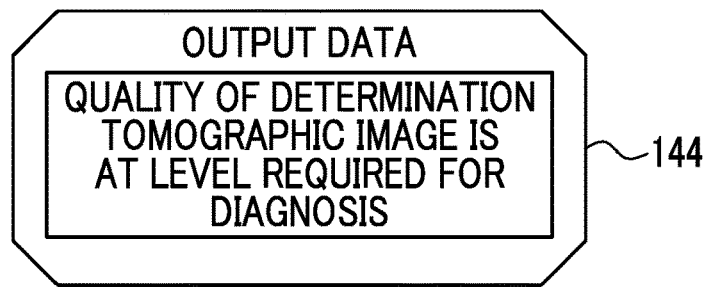

FIG. 33A illustrates the output data 144 in a case in which the quality of the determination tomographic image JT is not at a level required for diagnosis. In contrast, FIG. 33B illustrates the output data 144 in a case in which the quality of the determination tomographic image JT is at the level required for diagnosis.

Figure 34:
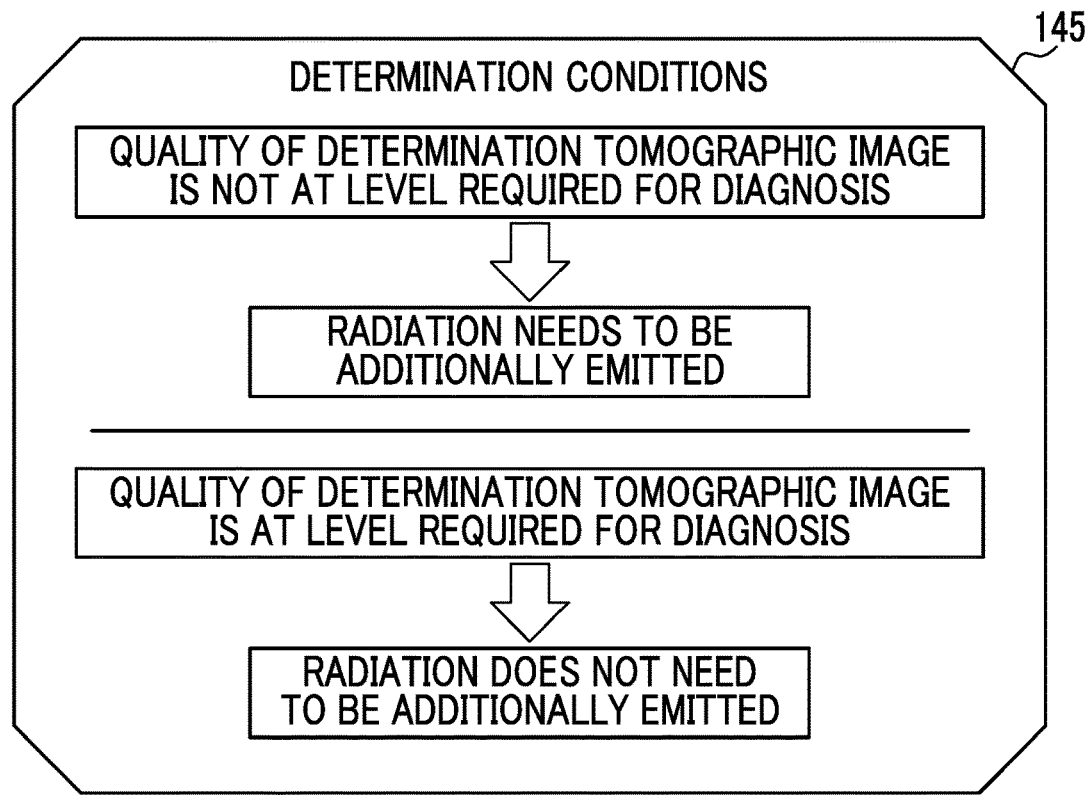
FIG. 34 is a diagram illustrating determination conditions according to a fourth embodiment.

In FIG. 34, the content of the determination conditions 145 is that, in a case in which the output data 144 indicates that the quality of the determination tomographic image JT is not at the level required for diagnosis, it is determined that the radiation 37 needs to be emitted at the irradiatable positions different from the irradiation positions. In this case, the output unit 142 outputs the determination result information 76 indicating that the radiation 37 needs to be emitted at the irradiatable positions different from the irradiation positions. In addition, the content of the determination conditions 145 is that, in a case in which the output data 144 indicates that the quality of the determination tomographic image JT is at the level required for diagnosis, it is determined that the radiation 37 does not need to be emitted at the irradiatable positions different from the irradiation positions. In this case, the output unit 142 outputs the determination result information 76 indicating that the radiation 37 does not need to be emitted at the irradiatable positions different from the irradiation positions.

As described above, in the fourth embodiment, the determination unit 140 performs the determination using the first machine learning model 143. The determination tomographic image JT is input as the determination image to the first machine learning model 143 and the first machine learning model 143 outputs information indicating whether or not the quality of the input determination tomographic image JT is at the level required for diagnosis. Therefore, it is possible to directly determine whether or not the quality of the determination tomographic image JT is at the level required for diagnosis and to reduce the time and effort required to derive the image quality evaluation value QEV or to compare the image quality evaluation value QEV with the image quality evaluation threshold value QET, as in each of the above-described embodiments.

The third embodiment may be applied to direct the first machine learning model 143 to individually determine whether or not the granularity of the determination tomographic image JT is at the level required for diagnosis and whether or not the depth resolution of the determination tomographic image JT is at the level required for diagnosis.

Fifth Embodiment

Figure 35:
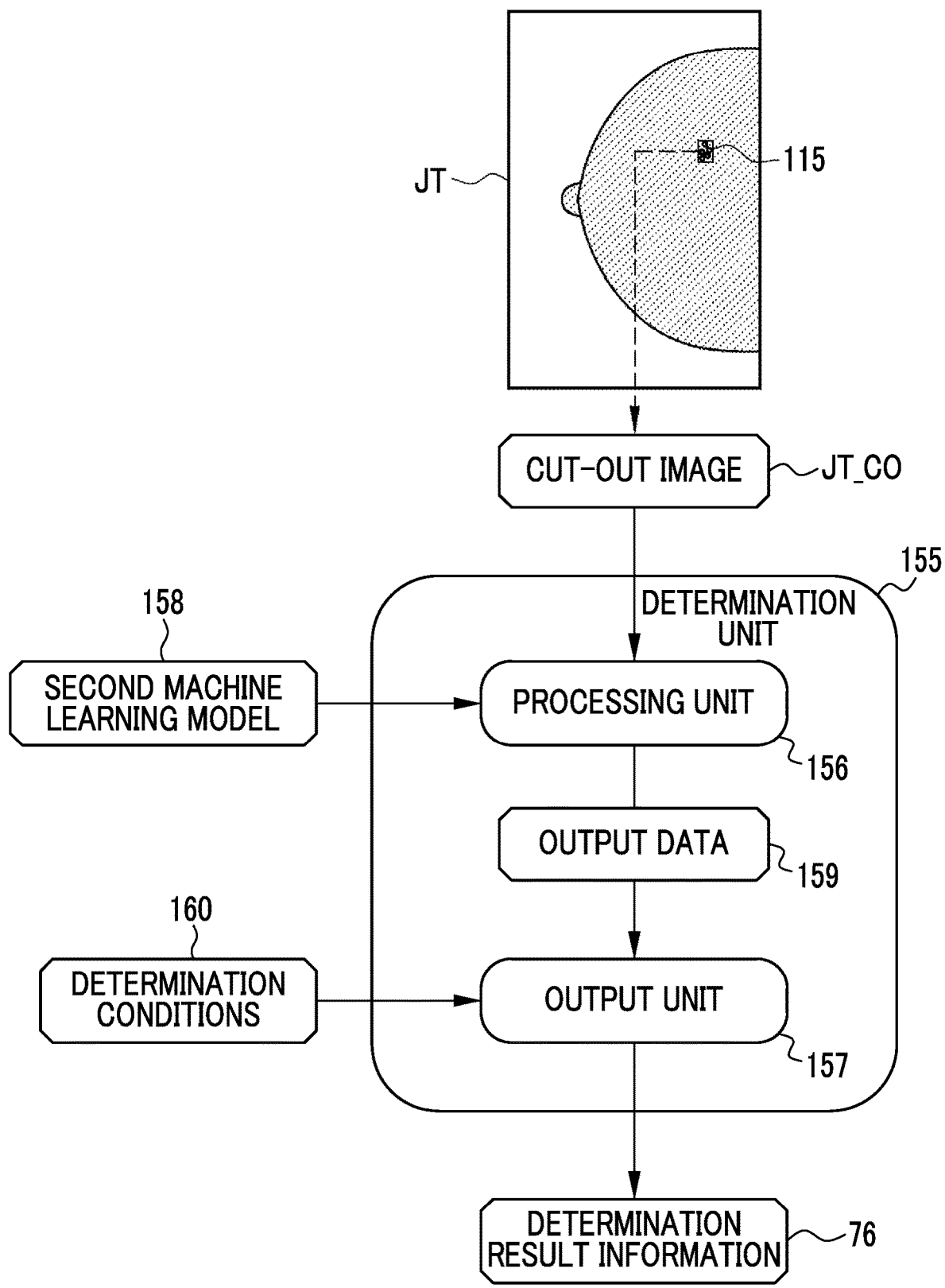
FIG. 35 is a diagram illustrating details of a determination unit according to a fifth embodiment.

In a fifth embodiment illustrated in FIG. 35, the determination is performed using a cut-out image JT_CO obtained by cutting out the region of the lesion 115 from the determination tomographic image JT and a second machine learning model 158.

In FIG. 35, a determination unit 155 according to the fifth embodiment includes a processing unit 156 and an output unit 157. The processing unit 156 inputs the cut-out image JT_CO obtained by cutting out the region of the lesion 115 from the determination tomographic image JT to the second machine learning model 158 and directs the second machine learning model 158 to output output data 159. The processing unit 156 outputs the output data 159 to the output unit 157. The output data 159 indicates whether or not the quality of the cut-out image JT_CO is at a level required for diagnosis. The output unit 157 outputs determination result information 76 on the basis of the output data 159 and determination conditions 160. The learning phase of the second machine learning model 158 is the same as that in the fourth embodiment except that the learning tomographic image LT is changed to a learning cut-out image. Therefore, the illustration and description thereof will be omitted. For example, the output data 159 and the determination conditions 160 are the same as those in the fourth embodiment except that the determination tomographic image JT is changed to the cut-out image JT_CO. Therefore, the illustration and description thereof will be omitted.

As such, in the fifth embodiment, the determination unit 155 performs the determination using the second machine learning model 158. The cut-out image JT_CO obtained by cutting out the region of the lesion 115 from the determination tomographic image JT is input as the determination image to the second machine learning model 158 and the second machine learning model 158 outputs information indicating whether or not the quality of the input cut-out image JT_CO is at the level required for diagnosis. Therefore, the following effects are obtained in addition to the same effects as those in the fourth embodiment. That is, as in the second embodiment, the image quality of the lesion 115, to which attention is paid in diagnosis using the tomographic image T, can be reliably set to the level required for diagnosis. Further, it is possible to reduce the load of the process of outputting the output data 159, as compared to the first machine learning model 143 according the fourth embodiment in which the entire determination tomographic image JT is a processing target.

The third embodiment may be applied to direct the second machine learning model 158 to individually determine whether or not the granularity of the cut-out image JT_CO is at the level required for diagnosis and whether or not the depth resolution of the cut-out image JT_CO is at the level required for diagnosis.

Sixth Embodiment

Figure 36:
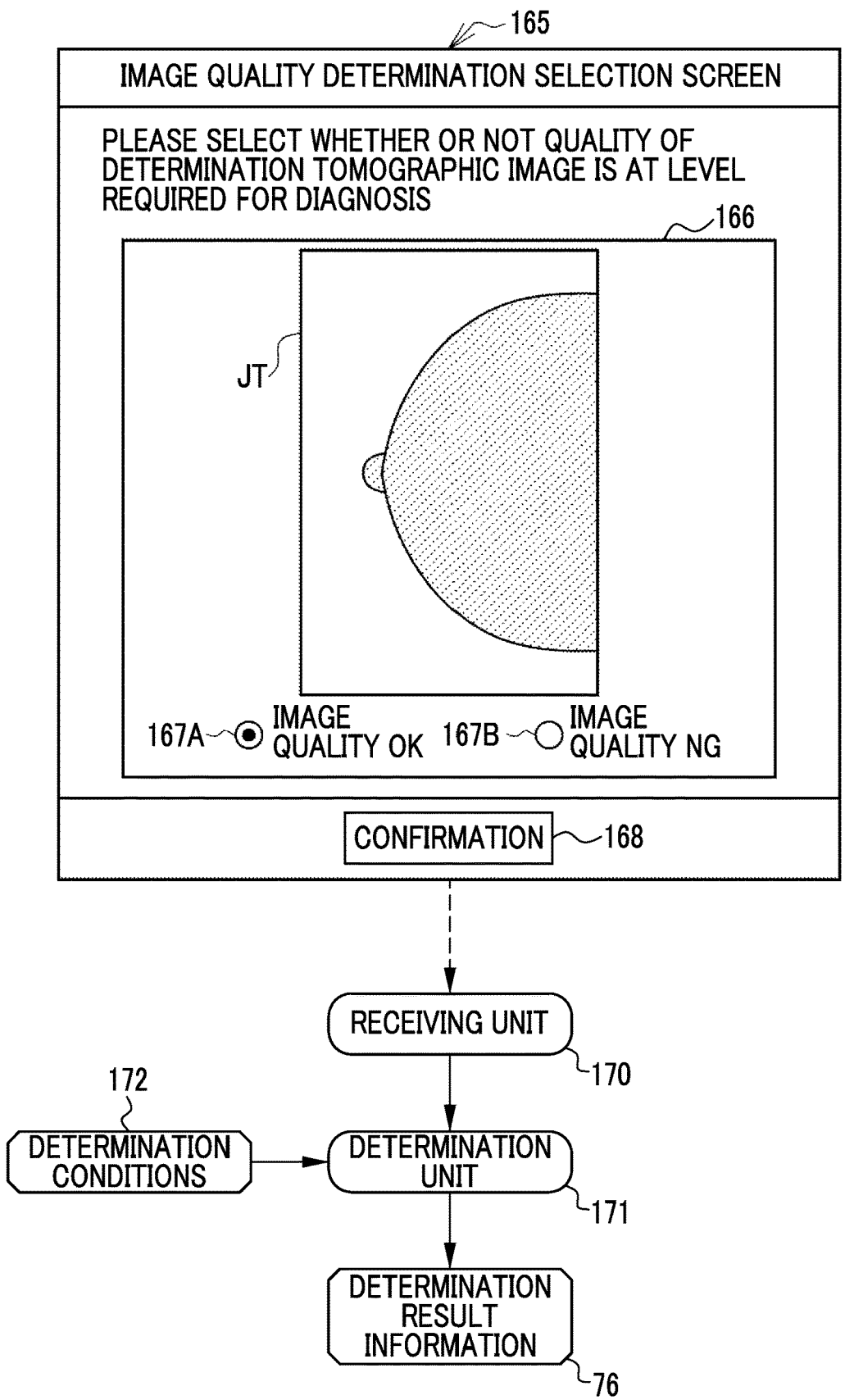
FIG. 36 is a diagram illustrating an image quality determination selection screen and a processing unit of a CPU of a control device according to a sixth embodiment.
Figure 37:
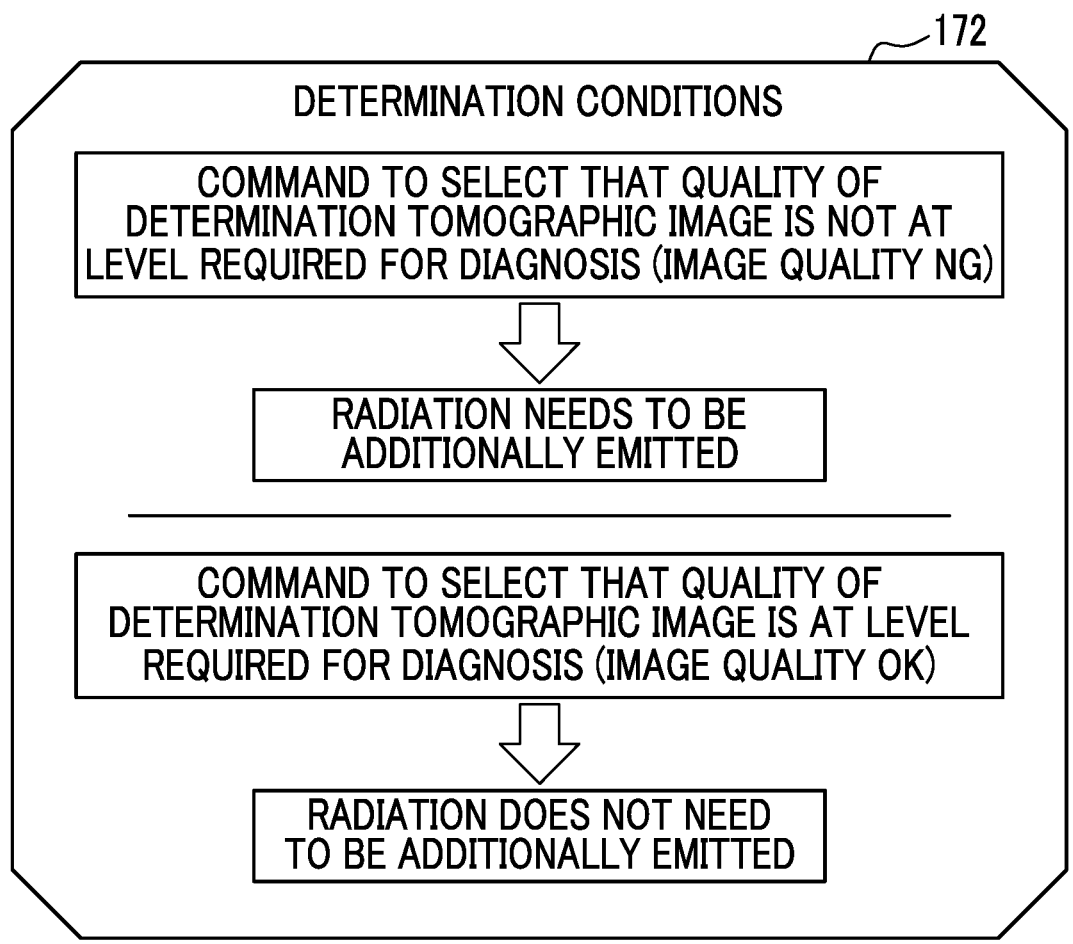
FIG. 37 is a diagram illustrating determination conditions according to the sixth embodiment.

In a sixth embodiment illustrated in FIGS. 36 and 37, the determination tomographic image JT is displayed, a command to select whether or not the quality of the determination tomographic image JT is at a level required for diagnosis is received, and the determination is performed on the basis of the selection command.

In FIG. 36, the display control unit 69 displays an image quality determination selection screen 165 on the display 54 in a case in which the generation unit 67 has generated the determination tomographic image JT. The image quality determination selection screen 165 includes a determination tomographic image display region 166. The determination tomographic image JT is displayed in the determination tomographic image display region 166. The determination tomographic image JT displayed in the determination tomographic image display region 166 is one determination tomographic image JT in one representative tomographic plane, for example, an intermediate tomographic plane among the tomographic planes TF1 to TFN.

Radio buttons 167A and 167B for allowing the operator to select whether or not the quality of the determination tomographic image JT is at the level required for diagnosis are provided below the determination tomographic image JT. The radio buttons 167A and 167B are alternative buttons. The radio button 167A is selected in a case in which the quality of the determination tomographic image JT is at the level required for diagnosis (represented by Image Quality OK in FIG. 36). In contrast, the radio button 167B is selected in a case in which the quality of the determination tomographic image JT is not at the level required for diagnosis (represented by Image Quality NG in FIG. 36).

In the sixth embodiment, a receiving unit 170 is constructed in the CPU of the control device. In a case in which one of the radio buttons 167A and 167B is selected and a command button 168 is selected, the receiving unit 170 receives a command to select whether or not the quality of the determination tomographic image JT is at the level required for diagnosis. The receiving unit 170 outputs the received selection command to a determination unit 171. The determination unit 171 outputs determination result information 76 on the basis of the selection command and determination conditions 172.

In FIG. 37, the content of the determination conditions 172 is that, in a case in which the radio button 167B is selected and the receiving unit 170 receives a selection command indicating that the quality of the determination tomographic image JT is not at the level required for diagnosis, it is determined that the radiation 37 needs to be emitted at the irradiatable positions different from the irradiation positions. In this case, the determination unit 171 outputs the determination result information 76 indicating that the radiation 37 needs to be emitted at the irradiatable positions different from the irradiation positions. In addition, the content of the determination conditions 172 is that, in a case in which the radio button 167A is selected and the receiving unit 170 receives a selection command indicating that the quality of the determination tomographic image JT is at the level required for diagnosis, it is determined that the radiation 37 does not need to be emitted at the irradiatable positions different from the irradiation positions. In this case, the determination unit 171 outputs the determination result information 76 indicating that the radiation 37 does not need to be emitted at the irradiatable positions different from the irradiation positions.

As described above, in the sixth embodiment, the display control unit 69 displays the determination tomographic image JT, the receiving unit 170 receives a command to select whether or not the quality of the determination tomographic image JT is at the level required for diagnosis, and the determination unit 171 performs determination on the basis of the selection command. Therefore, whether or not the radiation 37 needs to be emitted at the irradiatable positions different from the irradiation positions can be left to the decision of the operator. It is not necessary to derive the image quality evaluation value QEV unlike the first to third embodiments or it is not necessary to use the first and second machine learning models 143 and 158 unlike the fourth and fifth embodiments.

The third embodiment may be applied such that the receiving unit 170 individually receives a command to select whether or not the granularity of the determination tomographic image JT is at the level required for diagnosis and a command to select whether or not the depth resolution of the determination tomographic image JT is at the level required for diagnosis.

As in the first embodiment, a plurality of tomographic images in a plurality of tomographic planes among all of the tomographic planes TF1 to TFN may be used as the determination tomographic image JT.

Seventh Embodiment

Figure 38:
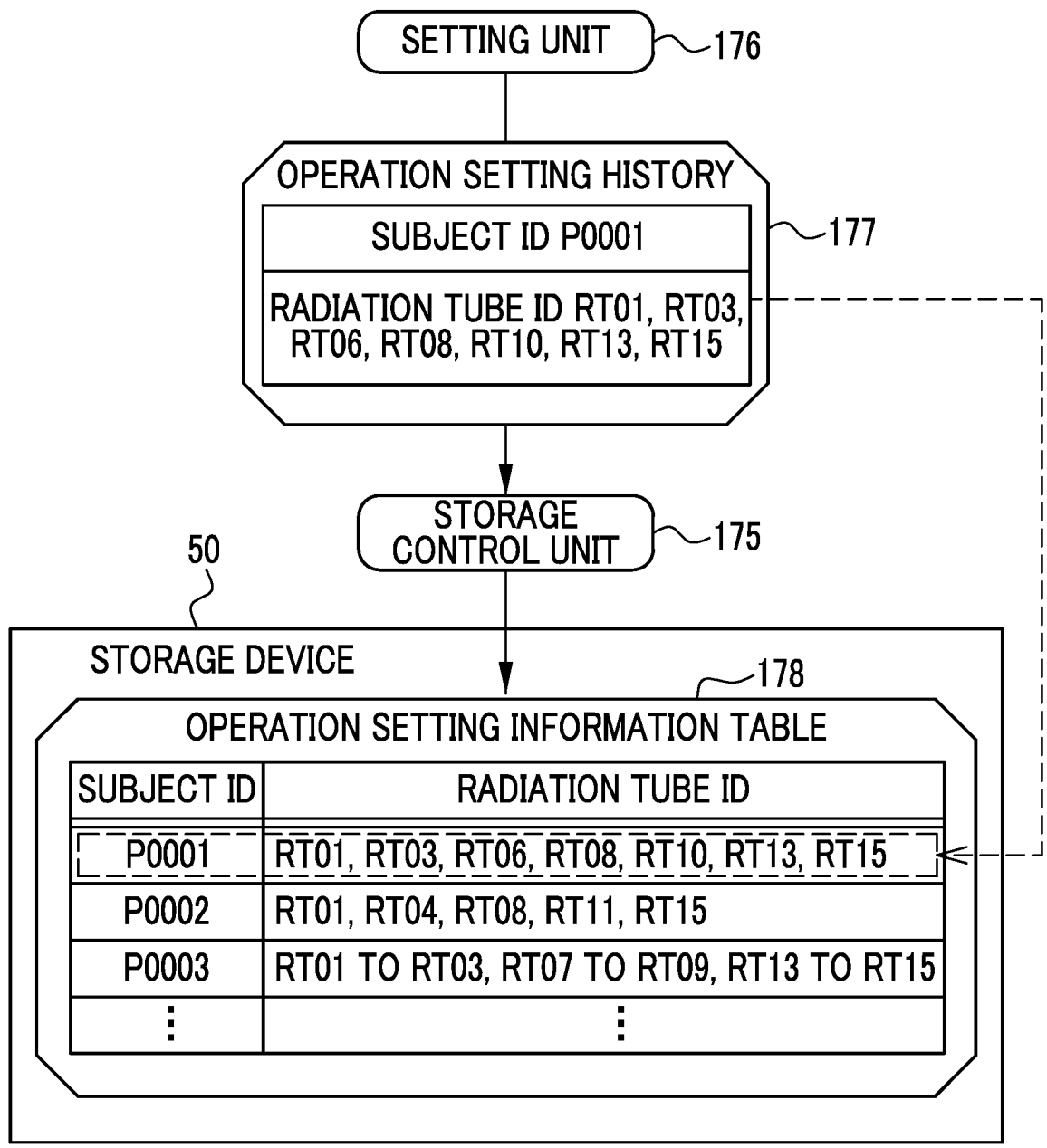
FIG. 38 is a diagram illustrating an aspect in which an operation setting history is registered in an operation setting information table by a storage control unit.
Figure 39:
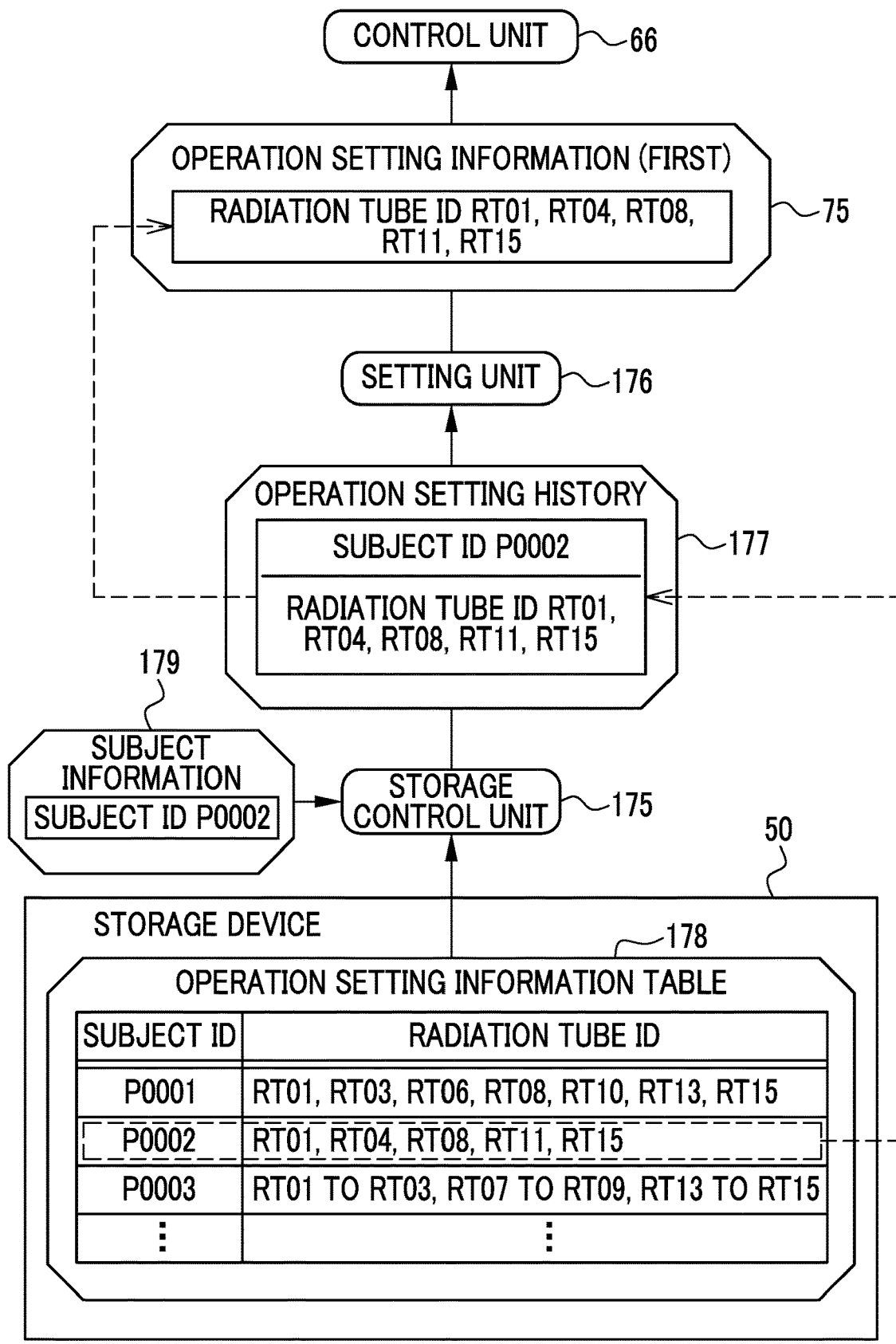
FIG. 39 is a diagram illustrating an aspect in which an initial irradiation position is set on the basis of the operation setting information table.

In a seventh embodiment illustrated in FIGS. 38 and 39, the control unit 66 stores an irradiation position related information table in which information related to the irradiation position where the radiation 37 is emitted is registered for each subject and sets an initial irradiation position on the basis of the irradiation position related information table.

As illustrated in FIG. 38, in the seventh embodiment, a storage control unit 175 is constructed in the CPU of the control device. The storage control unit 175 controls the storage of information in the storage device 50 and the reading of information from the storage device 50.

A setting unit 176 according to the seventh embodiment outputs an operation setting history 177 to the storage control unit 175 after one tomosynthesis imaging operation is ended. In the operation setting history 177, all of the radiation tube IDs set by the setting unit 176 in the tomosynthesis imaging are registered in association with the subject ID for identifying the subject H.

The storage control unit 175 receives the operation setting history 177 from the setting unit 176. The storage control unit 175 registers the received operation setting history 177 in an operation setting information table 178 in the storage device 50. The operation setting information table 178 is information in which the radiation tube ID of the radiation tube 27 emitting the radiation 37 under the control of the control unit 66 in the latest tomosynthesis imaging has been registered for each subject ID. That is, in this case, the operation setting history 177 is an example of "information related to an irradiation position where radiation has been emitted by a control unit" according to the technology of the present disclosure. The operation setting information table 178 is an example of an "irradiation position related information table" according to the technology of the present disclosure. FIG. 38 illustrates an aspect in which the operation setting history 177 of a subject ID "P0001" and radiation tube IDs "RT01, RT03, RT06, RT08, RT10, RT13, and RT15" is registered in the operation setting information table 178.

FIG. 39 illustrates a case in which tomosynthesis imaging is started from now. The storage control unit 175 receives subject information 179 including a subject ID. The subject information 179 is input by the operator through the input device 55. The storage control unit 175 reads an operation setting history 177 corresponding to the subject ID in the subject information 179 from the operation setting information table 178 in the storage device 50. The storage control unit 175 outputs the read operation setting history 177 to the setting unit 176. The setting unit 176 generates the operation setting information 75 of the first imaging set according to the operation setting history 177 and outputs the generated operation setting information 75 to the control unit 66.

FIG. 39 illustrates a case in which tomosynthesis imaging is performed for a subject H with a subject ID "P0002". According to the operation setting history 177 registered in the operation setting information table 178, the radiation tube IDs of the radiation tubes 27 emitting the radiation 37 under the control of the control unit 66 are "RT01, RT04, RT08, RT11, and RT15" in the latest tomosynthesis imaging for the subject H with the subject ID "P0002". Therefore, the setting unit 176 outputs, to the control unit 66, the operation setting information 75 in which RT01, RT04, RT08, RT11, and RT15 have been registered as the radiation tube IDs.

As described above, in the seventh embodiment, the storage control unit 175 stores the operation setting information table 178 that is an irradiation position related information table in which information related to the irradiation position where radiation has been emitted by the control unit is registered for each subject. Then, the initial irradiation position is set on the basis of the operation setting information table 178. The radiation tube IDs registered in the operation setting information table 178 are all of the radiation tube IDs set in a case in which it is determined that the radiation 37 does not need to be additionally emitted at the irradiatable positions different from the irradiation positions in the latest tomosynthesis imaging for each subject H. Therefore, the possibility that it will be determined that the radiation 37 does not need to be additionally emitted at the irradiatable positions different from the irradiation positions after the first imaging set is ended and the tomosynthesis imaging will be ended only by performing the first imaging set increases. As a result, it is possible to contribute to shortening the imaging time.

In practice, for example, the operation setting information table 178 is subdivided for each of the CC imaging and the MLO imaging, each of the left and right breasts M, for each of the irradiation conditions, such as a tube voltage and a tube current-irradiation time product, and each imaging purpose, which is not illustrated in FIGS. 38 and 39. The subject information 179 includes, for example, information indicating one of the CC imaging and the MLO imaging, information indicating one of the left and right breasts M, the irradiation conditions, and the imaging purpose.

Instead of the radiation tube ID, the ID of the irradiation position may be stored as the "information related to the irradiation position where radiation has been emitted by the control unit".

Eighth Embodiment

In an eighth embodiment illustrated in FIGS. 40 to 46, determination is performed using a third machine learning model 183.

Figure 40:
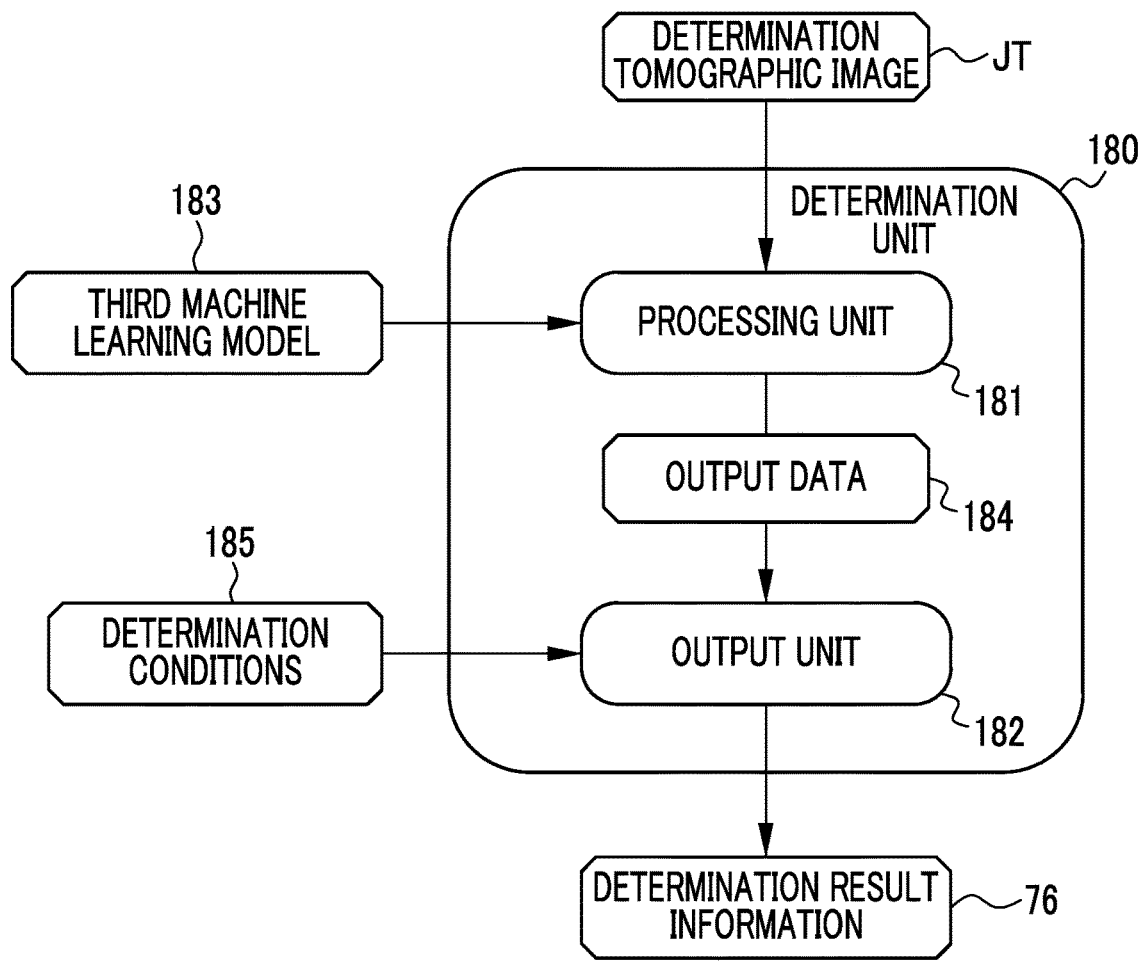
FIG. 40 is a diagram illustrating details of a determination unit according to an eighth embodiment.

In FIG. 40, a determination unit 180 according to the eighth embodiment includes a processing unit 181 and an output unit 182. The processing unit 181 inputs the determination tomographic image JT to the third machine learning model 183 and directs the third machine learning model 183 to output output data 184. The determination tomographic image JT is a tomographic image generated from the projection images P obtained by the emission of the radiation 37 at the irradiation positions in the first imaging set. The processing unit 181 outputs the output data 184 to the output unit 182. The output data 184 indicates the irradiation position (hereinafter, referred to as an irradiation essential position) where the emission of the radiation 37 is essential to generate the tomographic image T with an image quality level required for diagnosis (see FIG. 42). The output unit 182 outputs determination result information 76 on the basis of the output data 184 and determination conditions 185.

Figure 41:
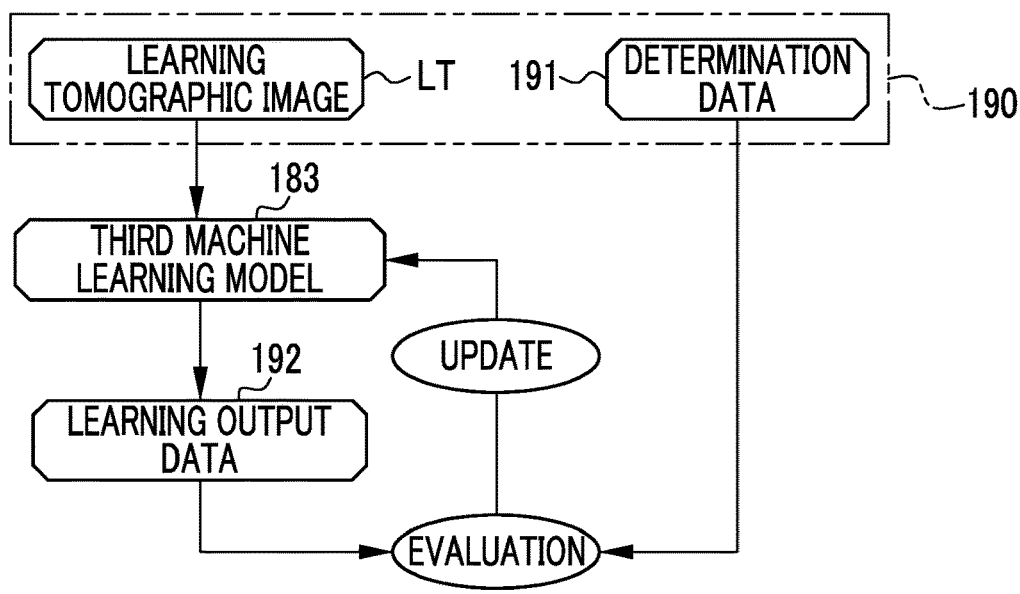
FIG. 41 is a diagram illustrating a process in a learning phase of a third machine learning model.

FIG. 41 illustrates a process in the learning phase of the third machine learning model 183. The third machine learning model 183 is trained using learning data 190. The learning data 190 includes a set of the learning tomographic image LT and determination data 191. The learning tomographic image LT is a tomographic image for training the third machine learning model 183 similarly to the first machine learning model 143 according to the fourth embodiment. The learning tomographic image LT is a tomographic image generated from the projection images P obtained by the emission of the radiation 37 at the irradiation positions in the first imaging set. The determination data 191 is data of all of the irradiation positions set until it is determined that the radiation 37 does not need to be additionally emitted at the irradiatable positions different from the irradiation positions in the tomosynthesis imaging in which the learning tomographic image LT has been generated.

As in the fourth embodiment, in the learning phase, the learning tomographic image LT is input to the third machine learning model 183. Then, the third machine learning model 183 outputs learning output data 192. The learning output data 192 indicates the irradiation essential position, similarly to the output data 184. The determination data 191 and the learning output data 192 are used to evaluate the prediction accuracy of the third machine learning model 183.

As in the fourth embodiment, in a case in which the content of the determination data 191 is matched with the content of the learning output data 192, it is evaluated that the prediction of the third machine learning model 183 is correct. In this case, parameters of the third machine learning model 183 are not updated. On the other hand, in a case in which the content of the determination data 191 is not matched with the content of the learning output data 192, it is evaluated that the prediction of the third machine learning model 183 is wrong. In this case, the parameters of the third machine learning model 183 are updated in order to increase the prediction accuracy.

As in the fourth embodiment, in the learning phase, the input of the learning tomographic image LT to the third machine learning model 183, the output of the learning output data 192 from the third machine learning model 183, the evaluation of the prediction accuracy of the third machine learning model 183 using the determination data 191 and the learning output data 192, and the update of the parameters of the third machine learning model 183 are repeated while the learning data 190 is changed. Therefore, in the learning phase, the prediction accuracy of the third machine learning model 183 is increased. Then, the third machine learning model 183 whose prediction accuracy has reached a preset level or higher is provided to the processing unit 181.

Figure 42:
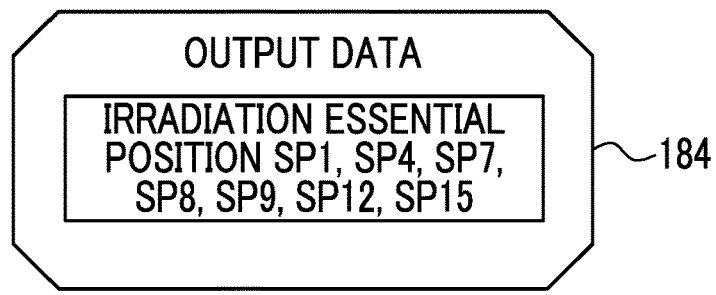
FIG. 42 is a diagram illustrating output data from the third machine learning model.

FIG. 42 illustrates the output data 184 in which the irradiatable positions SP1, SP4, SP7, SP8, SP9, SP12, and SP15 have been registered as the irradiation essential positions.

Figure 43:
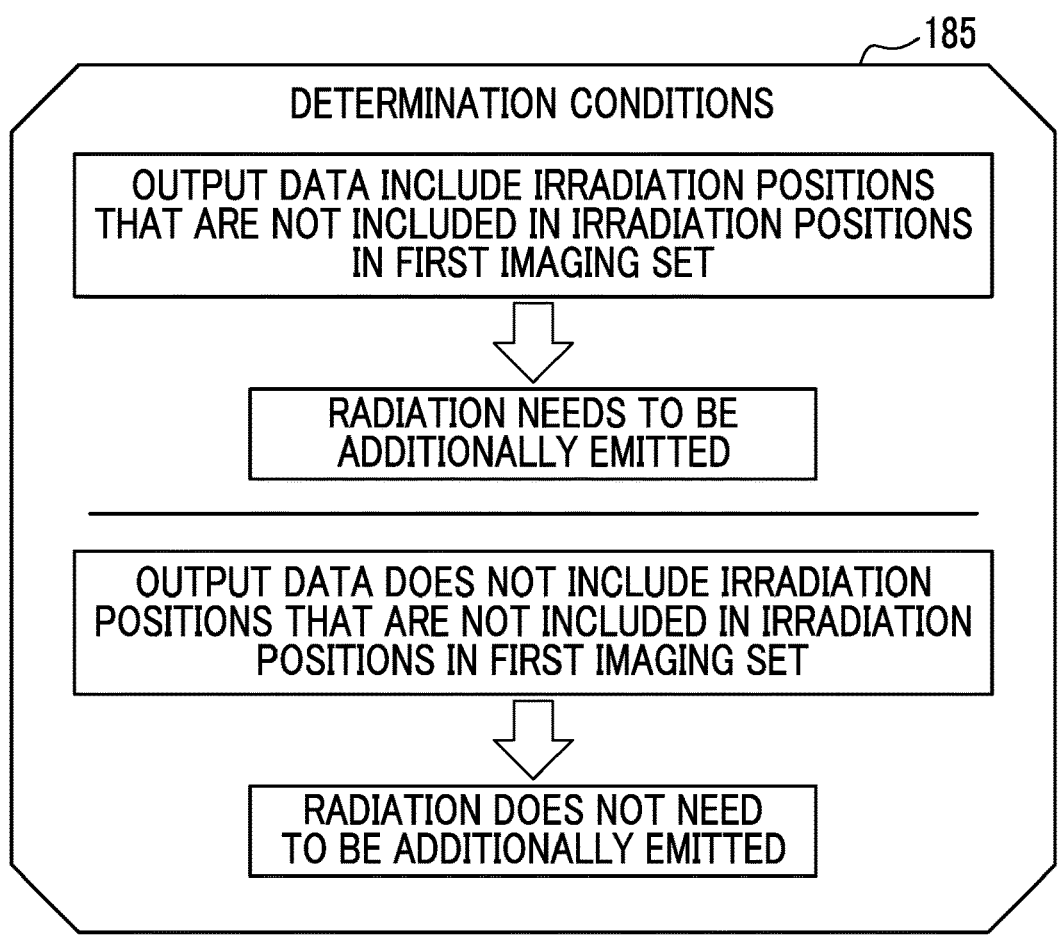
FIG. 43 is a diagram illustrating determination conditions according to the eighth embodiment.

In FIG. 43, the content of the determination condition 185 is that, in a case in which the output data 184 includes the irradiation essential positions which are not included in the irradiation positions corresponding to the radiation tubes 27 in the first imaging set, it is determined that the radiation 37 needs to be emitted at the irradiatable positions different from the irradiation positions. In this case, the output unit 182 outputs the determination result information 76 indicating that the radiation 37 needs to be emitted at the irradiatable positions different from the irradiation positions (see FIG. 45A). In addition, the content of the determination condition 185 is that, in a case in which the output data 184 does not include the irradiation essential position which is not included in the irradiation positions corresponding to the radiation tubes 27 in the first imaging set, it is determined that the radiation 37 does not need to be emitted at the irradiatable positions different from the irradiation positions. In this case, the output unit 182 outputs the determination result information 76 indicating that the radiation 37 does not need to be emitted at the irradiatable positions different from the irradiation positions (see FIG. 45B).

In FIG. 44, only the first imaging set is registered in setting conditions 195 according to the eighth embodiment. That is, RT01, RT08, and RT15 are registered as the radiation tube IDs.

Figure 45B:
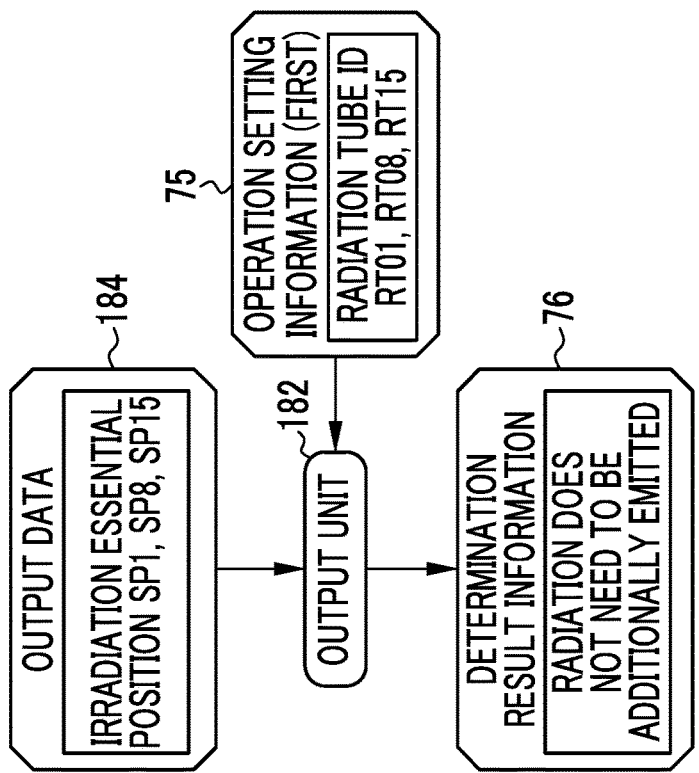
FIGS. 45A and 45B are diagrams illustrating variations in a first imaging set in the eighth embodiment.
Figure 45A:
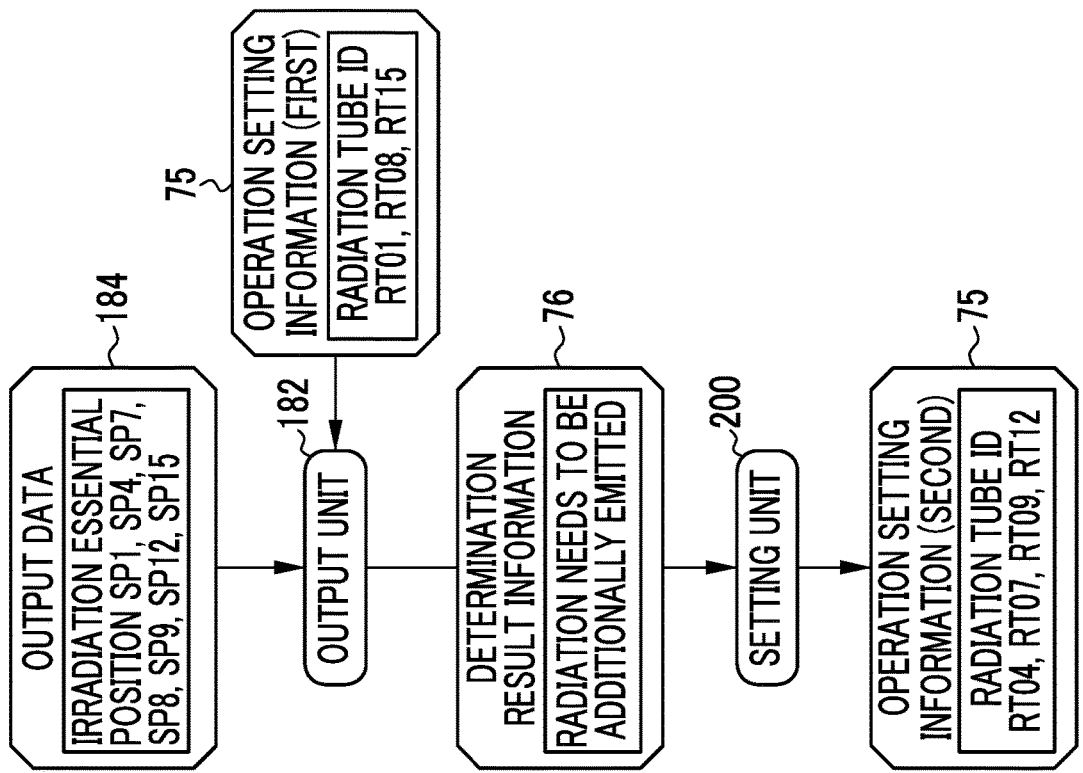

FIGS. 45A and 45B illustrate variations in the first imaging set according to the eighth embodiment. FIG. 45A illustrates a case in which the output data 184 includes the irradiation essential positions which are not included in the irradiation positions corresponding to the radiation tubes 27 in the first imaging set and the output unit 182 outputs the determination result information 76 indicating that the radiation 37 needs to be emitted at the irradiatable positions different from the irradiation positions. In contrast, FIG. 45B illustrates a case in which the output data 184 does not include the irradiation essential position which is not included in the irradiation positions corresponding to the radiation tubes 27 in the first imaging set and the output unit 182 outputs the determination result information 76 indicating that the radiation 37 does not need to be emitted at the irradiatable positions different from the irradiation positions.

FIG. 45A illustrates a case in which the irradiatable positions SP1, SP4, SP7, SP8, SP9, SP12, and SP15 have been registered as the irradiation essential positions in the output data 184, as in the example illustrated in FIG. 42. In this case, the irradiation essential positions which are not the irradiation positions (irradiatable positions SP1, SP8, and SP15) corresponding to the radiation tubes 27 with the radiation tube IDs in the first imaging set are the irradiatable positions SP4, SP7, SP9, and SP12. Therefore, a setting unit 200 according to the eighth embodiment outputs, to the control unit 66, the operation setting information 75 of the second imaging set in which RT04, RT07, RT09, and RT12 that are the radiation tube IDs of the radiation tubes 27 corresponding to the irradiatable positions SP4, SP7, SP9, and SP12 have been registered.

FIG. 45B illustrates a case in which the irradiatable positions SP1, SP8, and SP15 have been registered as the irradiation essential positions in the output data 184. In this case, since the tomosynthesis imaging is ended by the control unit 66, the setting unit 200 does not output the operation setting information 75.

Figure 46:
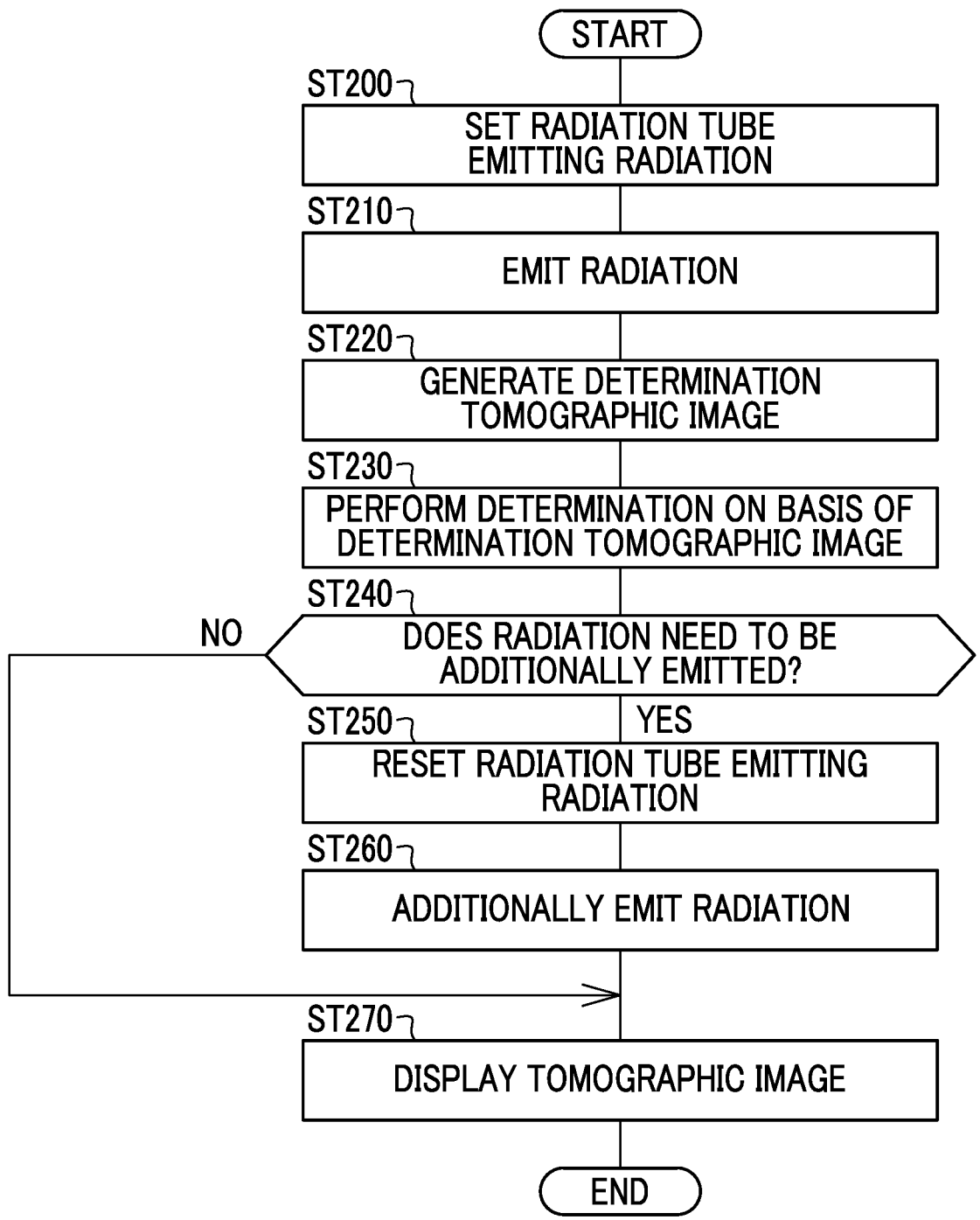
FIG. 46 is a flowchart illustrating a process procedure of a control device according to the eighth embodiment.

In FIG. 46 illustrating the process procedure of the control device according to the eighth embodiment, first, as illustrated in Step ST200, the setting unit 200 sets the radiation tubes 27 emitting the radiation 37 in the first imaging set according to the setting conditions 195 illustrated in FIG. 44.

The control unit 66 operates the radiation tubes 27 with the radiation tube IDs RT01, RT08, and RT15 registered in the operation setting information 75 of the first imaging set to emit the radiation 37 (Step ST210). Then, the projection images P are output from the radiation detector 26 to the generation unit 67. Step ST210 is an example of a "control step" according to the technology of the present disclosure.

The generation unit 67 generates the determination tomographic image JT on the basis of the projection images from the radiation detector 26 (Step ST220). The determination tomographic image JT is output from the generation unit 67 to the determination unit 180.

The determination unit 180 determines whether or not the radiation 37 needs to be additionally emitted at the irradiatable positions different from the irradiation positions in the first imaging set on the basis of the determination tomographic image JT, the third machine learning model 183, and the determination conditions 185 illustrated in FIG. 43 (Step ST230). Specifically, the processing unit 181 inputs the determination tomographic image JT to the third machine learning model 183 and the third machine learning model 183 outputs the output data 184. Then, it is determined whether or not the radiation 37 needs to be additionally emitted on the basis of whether or not the output data 184 includes the irradiation essential positions that are not included in the irradiation positions corresponding to the radiation tubes 27 with the radiation tube IDs in the first imaging set. Step ST230 is an example of a "determination step" according to the technology of the present disclosure.

In a case in which the determination unit 180 determines that the radiation 37 needs to be additionally emitted at the irradiatable positions different from the irradiation positions (YES in Step ST240), the setting unit 200 resets the radiation tubes 27 that additionally emit the radiation (Step ST250). Then, the control unit 66 operates the reset radiation tube 27 to additionally emit the radiation 37 (Step ST260). Then, the generation unit 67 generates the tomographic image T from the projection images P obtained by the emission of the radiation 37 at each irradiation position in the first and second imaging sets and the display control unit 69 displays the tomographic image T on the display 54 (Step ST270).

In a case in which the determination unit 180 determines that the radiation 37 does not need to be additionally emitted at an irradiatable position different from the irradiation position (NO in Step ST240), the control unit 66 ends the tomosynthesis imaging. In this case, the determination tomographic image JT in the first imaging set is output as the tomographic image JT from the generation unit 67 to the display control unit 69 and is displayed on the display 54 by the display control unit 69 (Step ST270).

As described above, in the eighth embodiment, the determination unit 180 performs the determination using the third machine learning model 183. The determination tomographic image JT generated from at least two projection images P obtained by the emission of the radiation 37 at least two initial irradiation positions is input as the determination image to the third machine learning model 183. The third machine learning model 183 outputs the irradiation essential position which is the irradiation position where the emission of the radiation 37 is essential to generate the tomographic image T with an image quality level required for diagnosis. In the first embodiment, in some cases, it is difficult to end the tomosynthesis imaging unless the imaging set is performed up to the eighth imaging set. In contrast, according to the eighth embodiment, the tomosynthesis imaging can be surely ended in the second imaging set at maximum, which can contribute to shortening the imaging time.

Further, as in the fifth embodiment, instead of the determination tomographic image JT, the cut-out image JT_CO of the lesion 115 may be input to the third machine learning model 183 and the third machine learning model 183 may output the irradiation essential position.

Ninth Embodiment

Figure 47:
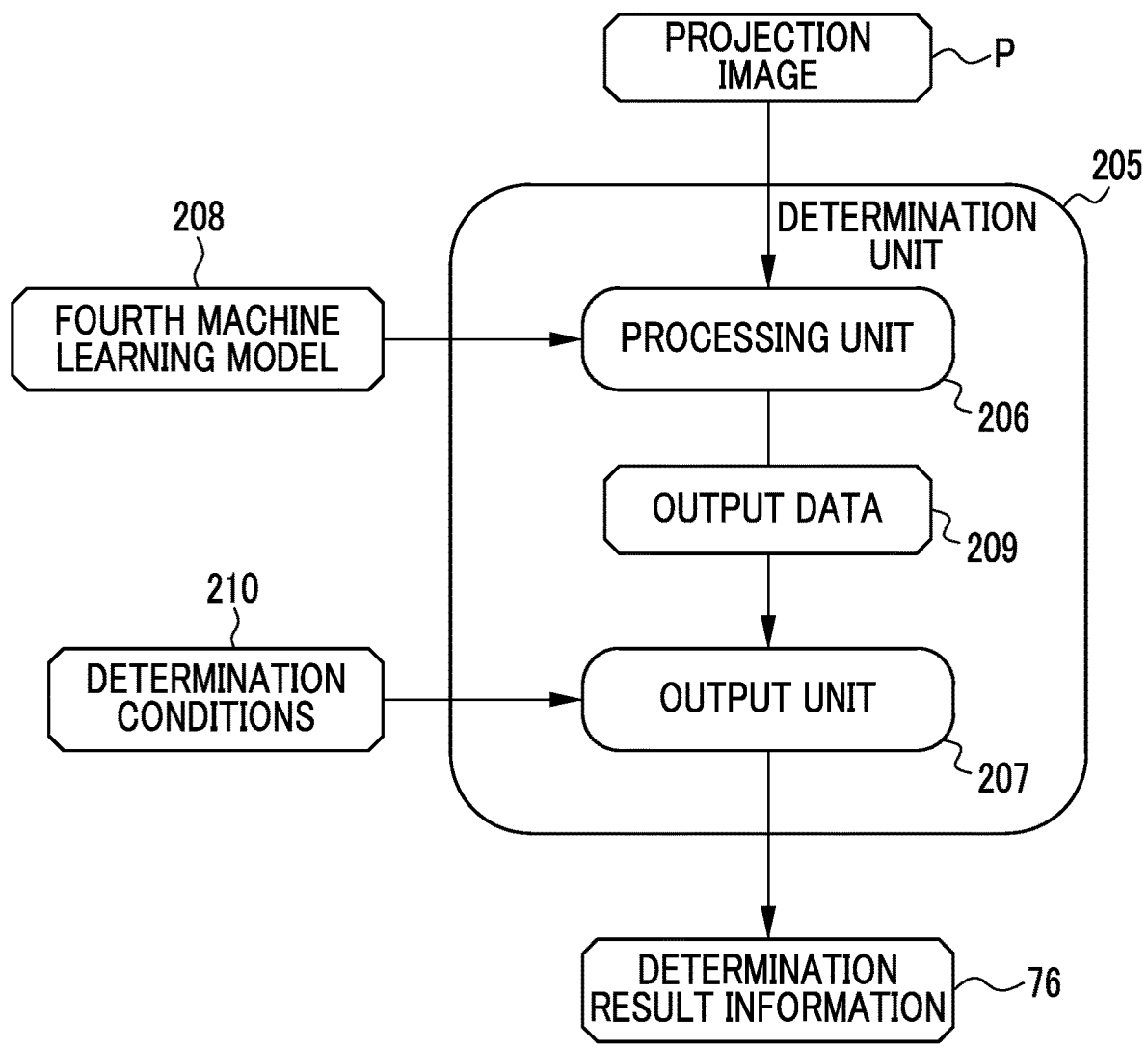
FIG. 47 is a diagram illustrating details of a determination unit according to a ninth embodiment.

In a ninth embodiment illustrated in FIG. 47, the determination is performed using a fourth machine learning model 208.

In FIG. 47, a determination unit 205 according to the ninth embodiment includes a processing unit 206 and an output unit 207. The processing unit 206 inputs the projection image P to the fourth machine learning model 208 and directs the fourth machine learning model 208 to output output data 209. The projection image P is obtained by the emission of the radiation 37 at the irradiation position in the first imaging set. The processing unit 206 outputs the output data 209 to the output unit 207. The output data 209 indicates an irradiation essential position, similarly to the output data 184 according to the eighth embodiment. The output unit 207 outputs determination result information 76 on the basis of the output data 209 and determination conditions 210. The learning phase of the fourth machine learning model 208 is the same as that in the eighth embodiment except that the learning tomographic image LT is changed to a learning projection image and thus the illustration and description thereof will be omitted. Since the determination conditions 210 are the same as the determination conditions 185 according to the eighth embodiment, the illustration and description thereof will be omitted.

As described above, in the ninth embodiment, the determination unit 205 performs the determination using the fourth machine learning model 208. The projection image P obtained by the emission of the radiation 37 at the initial irradiation position is input as the determination image to the fourth machine learning model 208 and the fourth machine learning model 208 outputs the irradiation essential position which is the irradiation position where the emission of the radiation is essential to generate the tomographic image T with an image quality level required for diagnosis. Therefore, it is possible to obtain the effect of reducing the time and effort required to generate the determination tomographic image JT, in addition to the same effects as those in the eighth embodiment.

The projection image P input to the fourth machine learning model 208 may be a projection image P based on one position such as a projection image P obtained by the emission of the radiation 37 at the irradiatable position SP1.

Instead of the projection image P, a cut-out image obtained by cutting out the region of the lesion 115 from the projection image P may be input to the fourth machine learning model 208 and the fourth machine learning model 208 may output the irradiation essential position.

The determination may be performed using a machine learning model obtained by combining the third machine learning model 183 according to the eighth embodiment which receives the determination tomographic image JT and the projection image P and outputs output data indicating the irradiation essential position and the fourth machine learning model 208 according to this embodiment.

Tenth Embodiment

Figure 48:
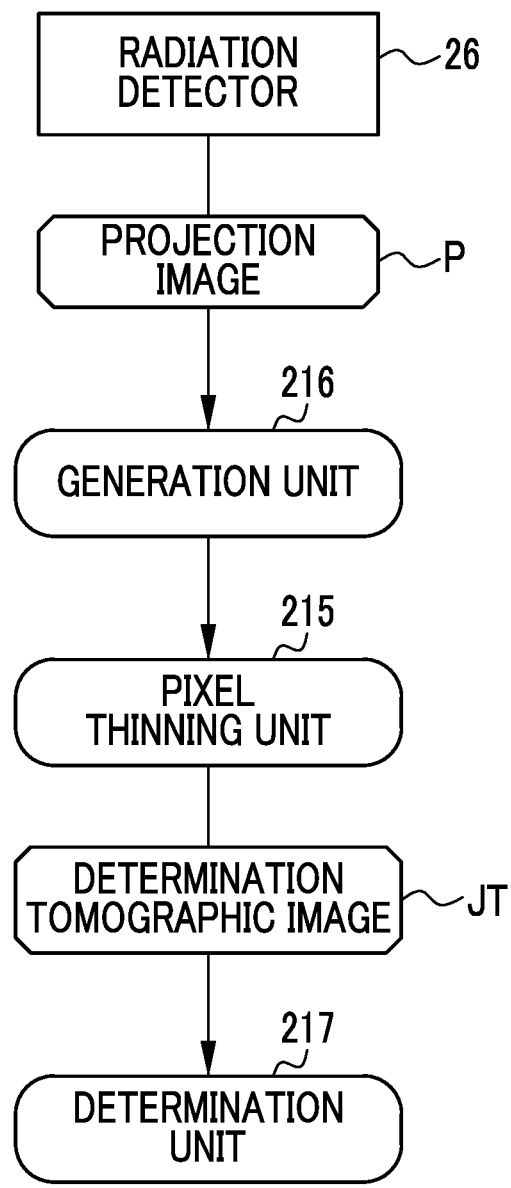
FIG. 48 is a diagram illustrating a processing unit of a CPU of a control device according to a tenth embodiment.

In a tenth embodiment illustrated in FIG. 48, a determination image used for determination by a determination unit is an image in which pixels have been thinned out as compared to the image output from the radiation detector 26.

As illustrated in FIG. 48, in the tenth embodiment, a pixel thinning unit 215 is constructed in the CPU of the control device. The pixel thinning unit 215 is provided between a generation unit 216 and a determination unit 217. The pixel thinning unit 215 receives the tomographic image that is the source of the determination tomographic image JT from the generation unit 216. The pixel thinning unit 215 performs a pixel thinning process for the received tomographic image. The pixel thinning process is, for example, a process of integrating the values of nine adjacent pixels into the value of one pixel to reduce the resolution of an image. The pixel thinning unit 215 outputs the tomographic image subjected to the pixel thinning process as the determination tomographic image JT to the determination unit 217.

As described above, in the tenth embodiment, the pixel thinning unit 215 thins out the pixels of the tomographic image to generate the determination tomographic image JT. Therefore, it is possible to reduce the processing load of the determination unit 217.

In a case in which the cut-out image JT_CO is used as the determination image as in the fifth embodiment, the pixel thinning process is performed for the cut-out image JT_CO. In a case in which the projection image P is used as the determination image as in the ninth embodiment, the pixel thinning process is performed for the radiographic image that is the source of the projection image P output from the radiation detector 26.

Eleventh Embodiment

In each of the above-described embodiments, the case in which the radiation tubes 27 are fixed at each of the irradiatable positions SP1 to SP15 has been described as an example. However, the invention is not limited thereto. In an eleventh embodiment illustrated in FIG. 49, the radiation tubes 27 can be moved.

Figure 49:
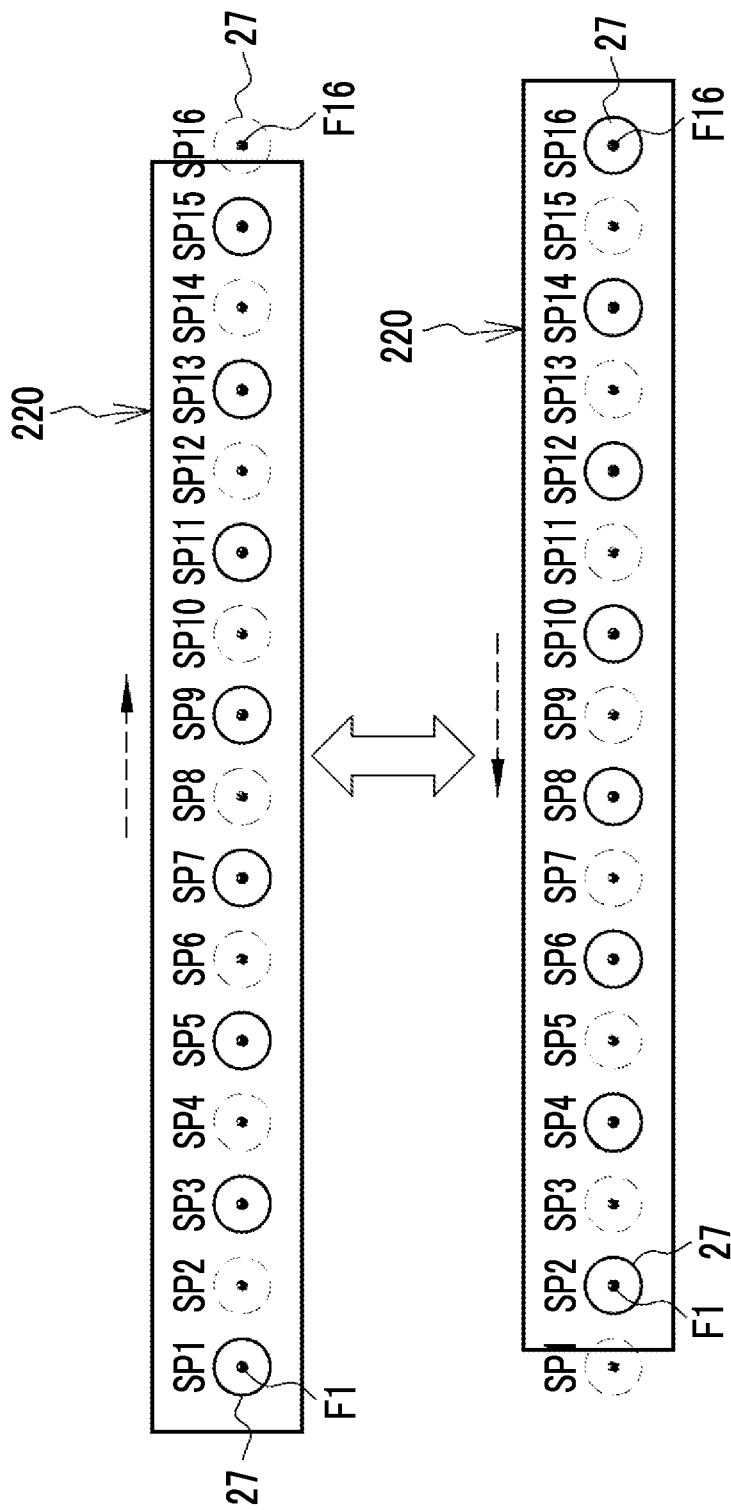
FIG. 49 is a diagram illustrating a radiation source in which a radiation tube is moved.

In FIG. 49, in a radiation source 220 according to the eleventh embodiment, a total of 16 irradiatable positions SP1 to SP16 where the radiation 37 are emitted at different irradiation angles are set. The irradiatable positions SP1 to SP16 correspond to focuses F1 to F16 that are arranged in a straight line at equal intervals.

The radiation tubes 27 are provided at eight positions which are half of the 16 irradiatable positions SP1 to SP16 and are provided at every other position. Then, the radiation source 220 is reciprocated in the X direction as represented by a dashed arrow. With the reciprocation of the radiation source 220 in the X direction, each radiation tube 27 is moved between two adjacent positions. For example, the leftmost radiation tube 27 is moved between the irradiatable position SP1 and the irradiatable position SP2 and the rightmost radiation tube 27 is moved between the irradiatable position SP15 and the irradiatable position SP16. That is, one radiation tube 27 takes charge of the emission of the radiation 37 at two positions.

Thus, in the eleventh embodiment, the radiation tube 27 is moved between two irradiatable positions. Therefore, the number of radiation tubes 27 can be less than that in the case in which the radiation tubes 27 are fixed at each of the irradiatable positions SP1 to SP15 and it is possible to reduce the cost of parts.

Figure 50:
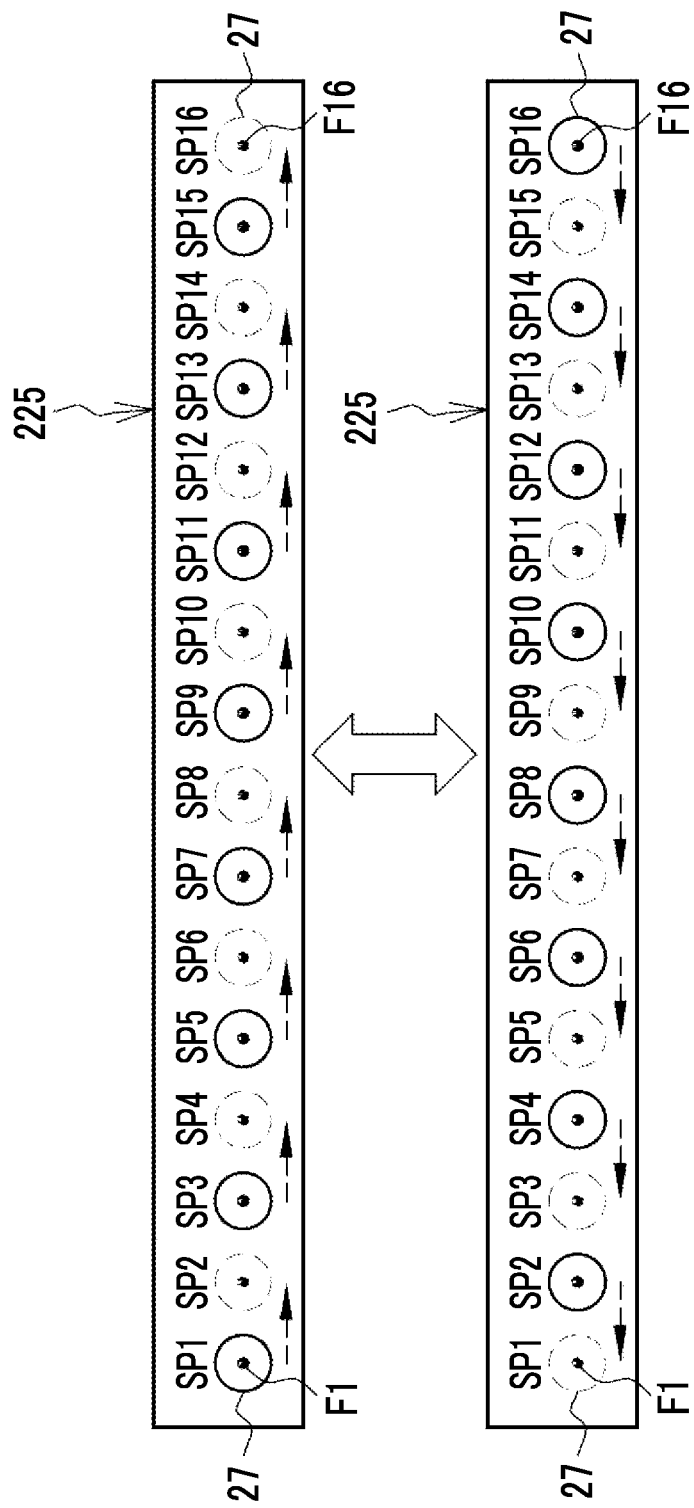
FIG. 50 is a diagram illustrating another example of the radiation source in which the radiation tube is moved.

As illustrated in FIG. 50, a radiation source 225 may not be reciprocated in the X direction and the radiation tubes 27 may be moved in the radiation source 225. As such, the aspect in which the radiation tube 27 is moved between at least two irradiatable positions includes an aspect in which the radiation source including the radiation tubes is moved as illustrated in FIG. 49 and an aspect in which the radiation tubes are moved in the radiation source as illustrated in FIG. 50. In addition, FIG. 50 illustrates an example in which the radiation tubes 27 are provided at eight positions that are half of the 16 irradiatable positions SP1 to SP16 so as to be disposed at every other position and are moved between two adjacent positions, as in FIG. 49.

The number of positions where one radiation tube 27 is moved may be greater than two illustrated in FIGS. 49 and 50. In addition, all of the radiation tubes 27 may not be moved, but some of the radiation tubes 27 may be fixed and the remaining radiation tubes 27 may be moved. Further, the radiation tubes 27 may not be moved one by one, but a unit including a plurality of radiation tubes 27, for example, five radiation tubes 27 may be moved.

The operation setting information 75 according to the eleventh embodiment includes information indicating at which of the irradiatable positions the radiation tubes 27 with the radiation tube IDs emit the radiation 37, in addition to the radiation tube IDs according to each of the above-described embodiments. For example, in FIGS. 49 and 50, in a case in which the irradiation position is the irradiatable position SP4, the operation setting information 75 includes the radiation tube ID of the second radiation tube 27 from the left which takes charge of the irradiatiable position SP4 and the ID or the position coordinates of the irradiatable position SP4.

The determination may be performed using a machine learning model that receives the projection image P and outputs information indicating whether or not the quality of the tomographic image T generated from the input projection image P is at the level required for diagnosis. Further, the determination may be performed using a machine learning model to which a cut-out image obtained by cutting out the region of the lesion 115 from the projection image P is input and which outputs information indicating whether or not the quality of the tomographic image T generated from the projection image P which is the source of the input cut-out image is at the level required for diagnosis.

Figure 51:
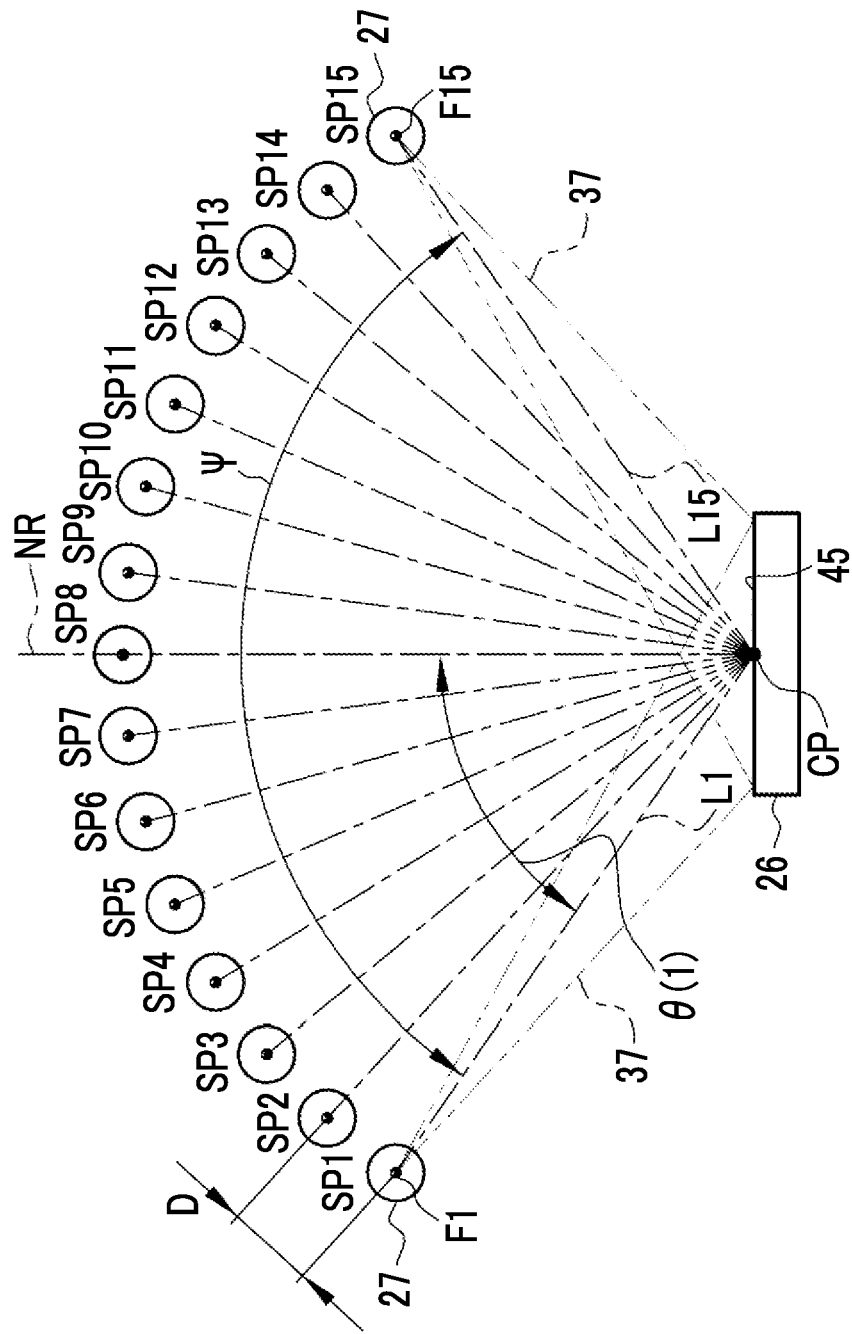
FIG. 51 is a diagram illustrating an example in which radiation tubes are disposed at a plurality of irradiatable positions where the focuses of radiation are set so as to be arranged in an arc shape at equal intervals.

In each of the above-described embodiments, the positions where the focuses F are disposed are arranged in a straight line. However, the invention is not limited thereto. As illustrated in FIG. 51, a plurality of irradiatable positions SP1 to SP15 where the focuses F1 to F15 are disposed may be arranged in an arc shape at equal intervals D. In this case, the radiation tubes 27 may be moved as in the eleventh embodiment.

Instead of the simple imaging in which the CC imaging illustrated in FIG. 5 and the MLO imaging illustrated in FIG. 6 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images P obtained by the tomosynthesis imaging or a plurality of tomographic images T generated by the generation unit.

In each of the above-described embodiments, the mammography apparatus 10 has been exemplified. In the related art, performing tomosynthesis imaging in the mammography apparatus 10 has been found to be useful as a method for easily finding lesions such as microcalcifications of the breast M. Therefore, it is preferable to apply the tomosynthesis imaging control device according to the present disclosure to the mammography apparatus 10.

Figure 52:
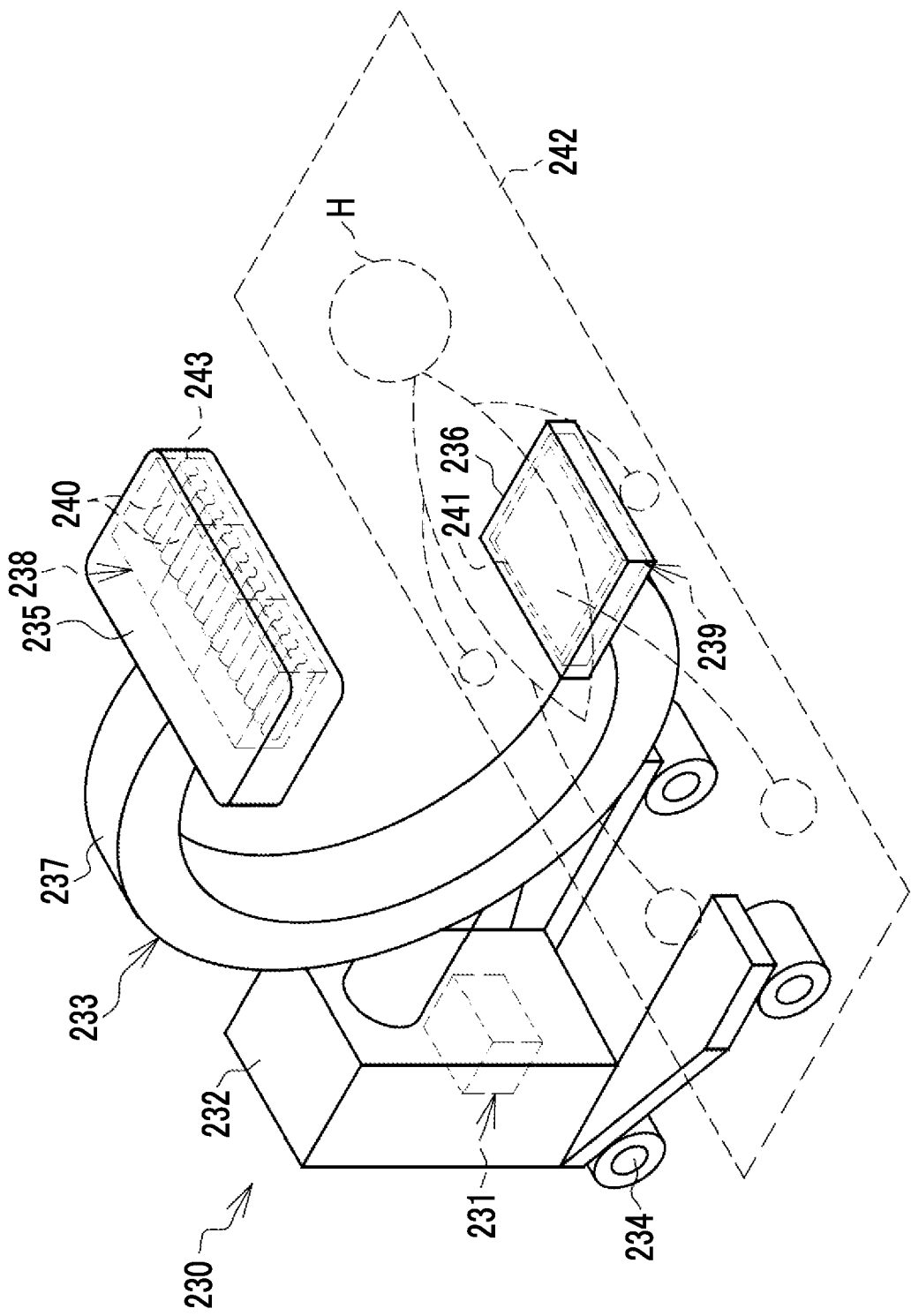
FIG. 52 is a diagram illustrating an imaging apparatus for surgery.

Of course, the tomosynthesis imaging control device according to the present disclosure may be applied to imaging apparatuses other than the mammography apparatus 10. For example, the tomosynthesis imaging control device according to the present disclosure may be applied to an imaging apparatus 230 illustrated in FIG. 52 which captures the image of the subject H during surgery.

The imaging apparatus 230 comprises an apparatus main body 232 having a control device 231 provided therein and an arm 233 having a substantially C-shape in a side view. A carriage 234 is attached to the apparatus main body 232 such that the apparatus main body 232 can be moved. The arm 233 includes a radiation source accommodation portion 235, a detector accommodation portion 236, and a main body portion 237. As in the mammography apparatus 10 illustrated in FIG. 1, the radiation source accommodation portion 235 accommodates a radiation source 238. In addition, the detector accommodation portion 236 accommodates a radiation detector 239. The radiation source accommodation portion 235 and the detector accommodation portion 236 are held by the main body portion 237 at a posture where they face each other.

The radiation source 238 and the radiation detector 239 have the same basic configurations as the radiation source 25 and the radiation detector 26 illustrated in FIG. 1, respectively. However, the imaging apparatus 230 captures an image of an object, such as the entire chest of the subject H, which is larger than the breast M. Therefore, a radiation tube 240 forming the radiation source 238 has a larger diameter than each radiation tube 27 of the mammography apparatus 10. In addition, the radiation detector 239 has an imaging surface 241 whose area is larger than that of the imaging surface 45 of the radiation detector 26. The number of radiation tubes 240 arranged may increase in order to respond to the capture of the image of a large object.

The detector accommodation portion 236 is inserted below a bed 242 on which the subject H lies supine. The bed 242 is made of a material that transmits the radiation 37. The radiation source accommodation portion 235 is provided above the subject H at a position that faces the detector accommodation portion 236 with the subject H interposed therebetween.

In the imaging apparatus 230, similarly to the mammography apparatus 10, the control device 231 performs control to emit the radiation 37 at the irradiation positions whose number is smaller than the total number of irradiatable positions and determines whether or not the radiation 37 needs to be additionally emitted at the irradiatable positions different from the irradiation positions. The imaging apparatus 230 can perform simple imaging using one radiation tube 240, in addition to the tomosynthesis imaging. In addition, instead of the simple imaging, the imaging apparatus may generate a composite radiographic image. Further, the imaging apparatus 230 may capture both still radiographic images and moving radiographic images. Furthermore, reference numeral 243 indicates a housing for the radiation source 238.

The tomosynthesis imaging control device according to the present disclosure may be applied to a general radiography apparatus configured by combining a ceiling-suspended radiation source and an upright imaging table or a decubitus imaging table in which a radiation detector is set, in addition to the imaging apparatus 230 for surgery. Further, the tomosynthesis imaging control device according to the present disclosure may be applied to, for example, a cart-type mobile radiography apparatus which is moved to each hospital room and is used to capture the image of the subject H.

In each of the above-described embodiments, the radiation tube ID (in a case in which the radiation tube 27 is fixed at the irradiatable position), and the radiation tube ID and the ID or position coordinates of the irradiation position (in a case in which the radiation tube 27 can be moved between at least two irradiatable positions) are given as examples of the operation setting information 75. However, the invention is not limited thereto. The ID or position coordinates of the irradiation position may be used as the operation setting information 75. In this case, for example, the control unit 66 replaces the ID or position coordinates of the irradiation position with the radiation tube ID and performs control to emit the radiation 37 at the irradiation position.

The hardware configuration of the computer forming the tomosynthesis imaging control device can be modified in various ways. For example, the tomosynthesis imaging control device may be configured by a plurality of computers that are separated as hardware in order to improve processing capability and reliability. For example, the functions of the setting unit 65, the control unit 66, the generation unit 67, the display control unit 69 and the function of the determination unit 68 are distributed to two server computers. In this case, the two server computers form the tomosynthesis imaging control device.

As described above, the hardware configuration of the computer can be appropriately changed according to the required performance, such as processing capability, safety, and reliability. Further, not only hardware but also an application program, such as the operation program 60, can be duplicated, or distributed and stored in a plurality of storage devices in order to ensure safety and reliability.

In each of the above-described embodiments, for example, the following various processors can be used as the hardware structure of processing units performing various processes, such as the setting units 65, 135, 176, and 200, the control unit 66, the generation units 67 and 216, the determination units 68, 120, 125, 140, 155, 171, 180, 205, and 217, the display control unit 69, the derivation units 85 and 121, the comparison unit 86, the output units 87, 130, 142, 157, 182, and 207, the first derivation unit 126, the second derivation unit 127, the first comparison unit 128, the second comparison unit 129, the processing units 141, 156, 181, and 206, the receiving unit 170, the storage control unit 175, and the pixel thinning unit 215. The various processors include, for example, the CPU 52 which is a general-purpose processor executing software to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to understand the invention described in the following Supplementary Note 1 from the above description.

Supplementary Note 1

There is provided a tomosynthesis imaging control device comprising: a control processor that, in a case in which tomosynthesis imaging that irradiates an object with radiation at a plurality of different irradiation angles in order to generate a tomographic image in any tomographic plane of the object is performed using a plurality of radiation tubes, controls an operation of the radiation tubes such that the radiation is emitted at irradiation positions whose number is smaller than a total number of irradiatable positions preset so as to correspond to the irradiation angles; and a determination processor that determines whether or not the radiation needs to be additionally emitted at the irradiatable positions different from the irradiation positions in order to obtain the tomographic image with an image quality level required for diagnosis, on the basis of a determination image obtained by the emission of the radiation at the irradiation positions.

In the technology according to the present disclosure, the above-described various embodiments and/or various modification examples may be combined with each other. In addition, the present disclosure is not limited to the above-described embodiments and various configurations can be used without departing from the scope and spirit of the present disclosure. Further, the technology of the present disclosure is applied to a storage medium that temporarily stores the program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, the description of, for example, common technical knowledge that does not need to be particularly described to enable the implementation of the technology of the present disclosure are omitted in order to avoid confusion and facilitate the understanding of portions related to the technology of the present disclosure.

In the specification, "A and/or B" is synonymous with "at least one of A and B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A tomosynthesis imaging control device comprising:
a control processor that, in a case in which tomosynthesis imaging that irradiates an object with radiation at a plurality of different irradiation angles to generate a tomographic image in any tomographic plane of the object is performed using a plurality of radiation tubes, controls an operation of the radiation tubes such that the radiation is emitted at irradiation positions whose number is smaller than a total number of irradiatable positions preset so as to correspond to the irradiation angles; and
a determination processor that determines whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

2. The tomosynthesis imaging control device according to claim 1,
wherein the tomographic image is generated from all of the projection images obtained by the emission of the radiation at the irradiation positions.

3. The tomosynthesis imaging control device according to claim 1,
wherein, in a case in which the determination processor determines that the radiation needs to be additionally emitted at the irradiatable positions different from the irradiation positions, the control processor performs control to additionally emit the radiation at an additional irradiation position among the different irradiatable positions, and in a case in which the determination processor determines that the radiation does not need to be additionally emitted at the irradiatable positions different from the irradiation positions, the control processor ends the tomosynthesis imaging.

4. The tomosynthesis imaging control device according to claim 3,
wherein the determination processor performs the determination using a determination tomographic image generated from at least two projection images obtained by the emission of the radiation at at least two irradiation positions as the determination image.

5. The tomosynthesis imaging control device according to claim 4,
wherein the determination processor performs the determination by comparing an image quality evaluation value of the determination tomographic image with a preset image quality evaluation threshold value.

6. The tomosynthesis imaging control device according to claim 5,
wherein the image quality evaluation value is a value of a lesion of the object.

7. The tomosynthesis imaging control device according to claim 4,
wherein the determination processor performs the determination using a first machine learning model to which the determination tomographic image is input as the determination image and which outputs data indicating whether or not a quality of the input determination tomographic image is at the level required for diagnosis.

8. The tomosynthesis imaging control device according to claim 4,
wherein the determination processor performs the determination using a second machine learning model to which a cut-out image obtained by cutting out a region of a lesion of the object from the determination tomographic image is input as the determination image and which outputs data indicating whether or not a quality of the input cut-out image is at a level required for diagnosis.

9. The tomosynthesis imaging control device according to claim 4, further comprising:
a display control processor that performs control to display the determination tomographic image; and
a receiving processor that receives a command to select whether or not a quality of the determination tomographic image is at the level required for diagnosis,
wherein the determination processor performs the determination on the basis of the selection command received by the receiving processor.

10. The tomosynthesis imaging control device according to claim 4,
wherein the image quality includes granularity and depth resolution,
the determination processor individually determines whether or not the granularity of the determination tomographic image is at a level required for diagnosis and whether or not the depth resolution of the determination tomographic image is at a level required for diagnosis, and
the additional irradiation position is changed in a case in which the depth resolution is at the level required for diagnosis and the granularity is not at the level required for diagnosis, in a case in which the granularity is at the level required for diagnosis and the depth resolution is not at the level required for diagnosis, and in a case in which the granularity and the depth resolution are not at the levels required for diagnosis.

11. The tomosynthesis imaging control device according to claim 4, further comprising:
a storage control processor that performs control to store an irradiation position related information table in which information related to the irradiation position where the radiation has been emitted by the control processor is registered for each subject,
wherein an initial irradiation position is set on the basis of the irradiation position related information table.

12. The tomosynthesis imaging control device according to claim 4,
wherein the irradiatable positions having a smaller irradiation angle than previous irradiation positions are set as the additional irradiation positions.

13. The tomosynthesis imaging control device according to claim 1,
wherein the determination processor performs the determination using a third machine learning model to which a determination tomographic image generated from at least two projection images obtained by the emission of the radiation at at least two initial irradiation positions is input as the determination image and which outputs the irradiation position where the emission of the radiation is essential to generate the tomographic image with the image quality level required for diagnosis.

14. The tomosynthesis imaging control device according to claim 1,
wherein the determination processor performs the determination using a fourth machine learning model to which a projection image obtained by the emission of the radiation at an initial irradiation position is input as the determination image and which outputs the irradiation position where the emission of the radiation is essential to generate the tomographic image with the image quality level required for diagnosis.

15. The tomosynthesis imaging control device according to claim 1,
wherein the determination image is an image in which pixels have been thinned out as compared to an image output from a radiation detector.

16. The tomosynthesis imaging control device according to claim 1,
wherein the irradiatable positions that are symmetric with respect to a line and/or the irradiatable positions that are arranged at equal intervals are set as the irradiation positions at a time.

17. The tomosynthesis imaging control device according to claim 1,
wherein the irradiatable positions corresponding to a maximum irradiation angle are set as the initial irradiation positions.

18. The tomosynthesis imaging control device according to claim 1,
wherein the radiation tube is fixed at the irradiatable position.

19. The tomosynthesis imaging control device according to claim 1,
wherein the radiation tube is moved between at least two irradiatable positions.

20. A method for operating a tomosynthesis imaging control device, the method comprising:
a control step of, in a case in which tomosynthesis imaging that irradiates an object with radiation at a plurality of different irradiation angles to generate a tomographic image in any tomographic plane of the object is performed using a plurality of radiation tubes, controlling an operation of the radiation tubes such that the radiation is emitted at irradiation positions whose number is smaller than a total number of irradiatable positions preset so as to correspond to the irradiation angles; and
a determination step of determining whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

21. A non-transitory computer-readable storage medium storing a program for operating a tomosynthesis imaging control device, the program causing a computer to function as:
a control processor that, in a case in which tomosynthesis imaging that irradiates an object with radiation at a plurality of different irradiation angles to generate a tomographic image in any tomographic plane of the object is performed using a plurality of radiation tubes, controls an operation of the radiation tubes such that the radiation is emitted at irradiation positions whose number is smaller than a total number of irradiatable positions preset so as to correspond to the irradiation angles; and
a determination processor that determines whether or not the radiation needs to be additionally emitted at the irradiatable positions different from the irradiation positions to obtain the tomographic image with an image quality level required for diagnosis, on the basis of a determination image obtained by the emission of the radiation at the irradiation positions.

* * * * *